United States Patent [19]

Moser et al.

[11] Patent Number: 4,673,735

[45] Date of Patent: Jun. 16, 1987

[54] AZO COMPOUNDS HAVING AT LEAST ONE 6-HYDROXYPYRID-2-ONE COUPLING COMPONENT RADICAL METAL COMPLEXES THEREOF AND INTERMEDIATES THEREFOR

[75] Inventors: Helmut Moser, Oberwil; Manfred Greve, Dornach; Reinhard Pedrazzi, Allschwil, all of Switzerland; Roland Wald, Huningue, France

[73] Assignee: Sandoz Ltd., Basel, Switzerland

[21] Appl. No.: 598,236

[22] Filed: Apr. 9, 1984

Related U.S. Application Data

[63] Continuation-in-part of Ser. No. 485,212, Apr. 15, 1983, abandoned.

[30] Foreign Application Priority Data

| Apr. 15, 1982 | [DE] | Fed. Rep. of Germany | 3213826 |
| Jan. 29, 1983 | [DE] | Fed. Rep. of Germany | 3302950 |
| May 9, 1983 | [DE] | Fed. Rep. of Germany | 3316915 |
| May 9, 1983 | [DE] | Fed. Rep. of Germany | 3316915 |

[51] Int. Cl.⁴ .................. C09B 44/02; C09B 44/04; C09B 44/06; C09B 44/08
[52] U.S. Cl. .................. 534/606; 534/604; 534/605; 534/613; 534/827; 544/181; 544/198; 546/2; 546/193
[58] Field of Search ............ 260/153, 187; 534/797, 534/603, 604, 605, 613, 606; 544/181, 198; 546/2, 193

[56] References Cited

U.S. PATENT DOCUMENTS

| 3,852,261 | 12/1974 | Steinemann | 260/156 |
| 4,087,244 | 5/1978 | Greve et al. | 8/41 |
| 4,273,707 | 6/1981 | Pedrazzi | 260/187 |
| 4,363,761 | 12/1982 | Pedrazzi | 260/153 |
| 4,367,172 | 1/1983 | Pedrazzi | 260/153 |

FOREIGN PATENT DOCUMENTS

| 2190972 | 2/1974 | France | 260/156 |
| 1296857 | 11/1972 | United Kingdom | 260/156 |
| 1297116 | 11/1972 | United Kingdom | 260/156 |

*Primary Examiner*—Floyd D. Higel
*Attorney, Agent, or Firm*—Gerald D. Sharkin; Richard E. Vila; Melvyn M. Kassenoff

[57] ABSTRACT

A compound of formula I

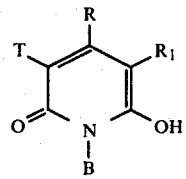

(I)

in metal-free; 1:1 or 1:2 metal complex form and, when an acid group is present, in free acid or acid addition salt form, in which $R_1$ is hydrogen or —N=N—D where D is a diazo component and R, T and B are organic radicals defined in the text.

13 Claims, No Drawings

AZO COMPOUNDS HAVING AT LEAST ONE 6-HYDROXYPYRID-2-ONE COUPLING COMPONENT RADICAL METAL COMPLEXES THEREOF AND INTERMEDIATES THEREFOR

This application is a continuation-in-part of application Ser. No. 06/485,212, filed Apr. 15, 1983 and now abandoned.

The invention relates to compounds suitable for use as dyestuffs and to intermediates for making such dyestuffs.

According to the invention there are provided compounds of formula I

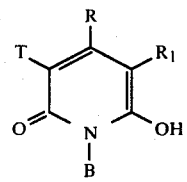  (I)

in metal-free or 1:1 or 1:2 metal complex form, and, in free acid or acid addition salt form,
in which
R is hydrogen; $C_{1-4}$alkyl; $C_{5-6}$cycloalkyl unsubstituted or substituted by one or two $C_{1-4}$alkyl groups; phenyl, benzyl or phenylethyl, the phenyl group of the latter three substituents being unsubstituted or substituted by one or two groups selected from methyl, ethyl, methoxy and ethoxy,
T is hydrogen, —CN,

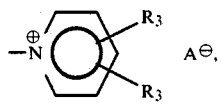

—COOR$_4$; —CON(R$_6$)$_2$, —SO$_2$N(R$_5$)$_2$;

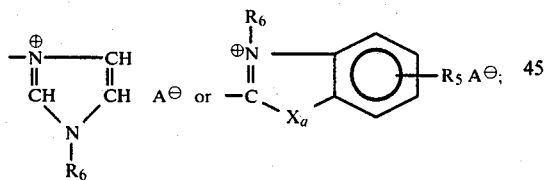

B is —A—NH—R$_2$; hydrogen; $C_{1-4}$alkyl unsubstituted or substituted by $C_{1-4}$alkoxy; $C_{2-4}$alkyl substituted by hydroxy; $C_{5-6}$cycloalkyl unsubstituted or substituted by one to three $C_{1-4}$alkyl groups; phenyl($C_{1-3}$alkyl), the phenyl group of which is unsubstituted or substituted by one to three groups selected from $C_{1-4}$alkyl, $C_{1-4}$alkoxy and halogen; —A$_4'$—N(R$_7$)$_2$; —A$_4$—N$^\oplus$(R$_8$)$_2$R$_9$A$^\ominus$ or —N(R$_7$)$_2$;
R$_1$ is a group α

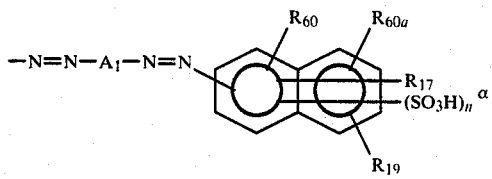

or, when B is —A—NH—R$_2$, hydrogen or —N=N—D;
where
X$_a$ is —O—, —N(R$_5$)— or —S—;
R$_3$ is hydrogen, $C_{1-4}$alkyl, —N(R$_5$)$_2$ or —CON(R$_5$)$_2$;
R$_4$ is $C_{1-6}$alkyl or phenyl($C_{1-3}$alkyl);
R$_5$ is hydrogen or $C_{1-4}$alkyl; or when two R$_5$'s are present attached to a nitrogen atom both R$_5$'s together with the N-atom to which they are attached may form a saturated ring which contains one to three hetero atoms;
R$_6$ is $C_{1-4}$alkyl;
A$_1$ is a residue of a tetrazo component;
R$_{60}$ is OH and R$_{60a}$ is hydrogen or NH$_2$ or R$_{60}$ is NH$_2$ and R$_{60a}$ is OH;
n is 0, 1 or 2;
A$_4$ is $C_{2-8}$alkylene or $C_{2-8}$alkenylene;
A$_4'$ is $C_{1-8}$alkylene or $C_{2-8}$alkenylene;
D is a diazo component;
where
A is $C_{2-8}$alkylene which may be interrupted by up to two hetero atoms; $C_{2-8}$alkenylene which may be interrupted by up to two hetero atoms; phenylene or cyclohexylene;
R$_2$ is

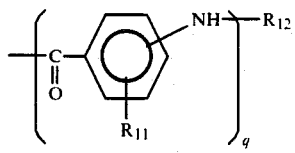

q is 0 or 1;
R$_{11}$ is hydrogen, halogen, nitro $C_{1-4}$alkyl or $C_{1-4}$alkoxy;
R$_{12}$ is

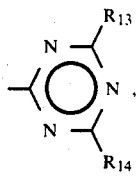

—CO(CH$_2$)$_a$—Z
or hydrogen,
a is an integer 1 to 3.
R$_{14}$ is an aliphatic, cycloaliphatic, aromatic or heterocyclic amine group in which the N-atom is attached to the triazinyl ring;
R$_{13}$ is a significance of R$_{14}$, halogen, —OH, —NH$_2$C$_{1-4}$alkoxy, phenyl or

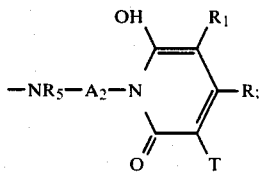

A$_2$ is a linear or branched $C_{2-6}$alkylene or —N*—H—CO—CH$_2$— where the starred N-atom is attached to the —NR$_5$ group;
Z is —N(R$_7$)$_2$ or —N$^\oplus$(R$_8$)$_2$R$_9$A$^\ominus$ each $R_7$, independently, is hydrogen, $C_{1-6}$alkyl, $C_{2-6}$alkyl substituted by an halogen, —OH or —CN group, phenyl($C_{1-3}$alkyl), the phenyl ring of which is unsubstituted or substituted by 1 to 3 groups selected from halogen, $C_{1-4}$alkyl and $C_{1-4}$alkoxy; or $C_{5-6}$cycloalkyl, unsubstituted or substituted by 1 or 3 $C_{1-4}$alkyl groups;

or both $R_7$'s together with the N-atom to which they are attached form a 5- or 6-membered saturated ring which contains one to three hetero atoms (referred to hereafter as the "cyclic significances of $R_7$");

each $R_8$ independently, has one of the non-cyclic significances of $R_7$ except hydrogen and $R_9$ is $C_{1-4}$alkyl unsubstituted or substituted by phenyl or both $R_8$'s, $R_9$ and the N-atom to which they are attached form a pyridinium group (attached by its N-atom) unsubstituted or substituted by one or two $C_{1-4}$alkyl groups; or a 5- or 6-membered saturated ring which contains 1 to 3 hetero atoms;

$R_{17}$ is hydrogen,

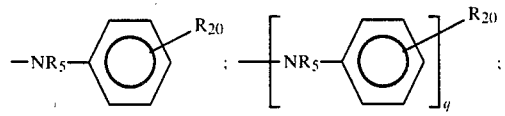

—N=N—K$_1$; —N=N—A$_{10}$—N=N—K$_1$ or

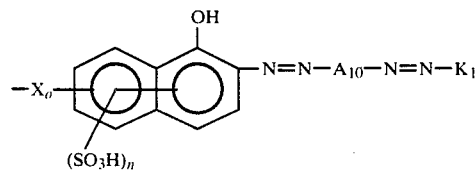

where $X_o$ is a bridging group and $A_{10}$ has a significance of $A_1$ defined above or is a coupling/diazo component $K_1$ is a diazo or coupling component;

$R_{19}$ is hydrogen or when $R_{17}$ is —N=N—K$_1$ or —N=N—A$_{10}$—N=N—K$_1$ additionally —OH, —NH$_2$, $C_{1-4}$alkyl-carbonylamino, benzoylamino or phenylamino, the phenyl group of the latter two substituents being unsubstituted or substituted by 1 or 2 substituents selected from halogen, —NO$_2$, —NH$_2$, $C_{1-4}$alkyl and $C_{1-4}$alkoxy;

$R_{20}$ is $\pm NR_5\rangle_qQ_1$—N(R$_7$)$_2$; $\pm NR_5\rangle_qQ_2$—N$^\ominus$(R$_8$)$_2$R$_9$A$^\ominus$ or

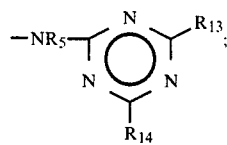

$Q_1$ is —CH$_2\overset{\oplus}{C}O$—, —$\overset{\oplus}{N}$HCOCH$_2$— or $C_{2-6}$alkylene where the starred atom is attached to —NR$_5$ (if present) or the phenyl ring to which $R_{20}$ is attached;

$Q_2$ is —CONHCOCH$_2$— or a significance of $Q_1$;

A$^\ominus$ is a non-chromophoric anion;

with the provisos that:

(i) when the compound of formula I is sulpho-free at least one water-solubilising basic or cationic group is present if the compound of formula I is a monoazo compound; and at least two water-solubilising groups are present if the compound of formula I is other than monoazo;

(ii) when one or more sulpho groups are present in the compound of formula I, the number of cationic and basic groups present is at least the number of sulpho groups+1;

(iii) when
B is —A—NH—R$_2$, where A is $C_{2-8}$alkylene;
R$_1$ on the same pyridone ring is hydrogen and
T on the same pyridone ring is —CN, then R$_2$ on the same pyridone ring is not hydrogen. Preferably in the compounds of formula I when B is —A—NH—R$_2$ then group B is sulpho-free.

Preferably A$_{10}$ has only a significance of A$_1$.

In the specification halogen means fluorine, chlorine, bromine or iodine, preferably chlorine.

For the avoidance of doubt the group D—N=N— includes the group α.

Where any symbol appears more than once in a formula unless indicated to the contrary its significances are independent of one another.

Any alkyl, alkylene or alkenylene present is linear or branched unless indicated otherwise. The alkyl group of any alkoxy group is linear or branched unless indicated to the contrary.

Any sulpho group present may be in free acid or salt form when in salt form the —SO$_3^\ominus$ is balanced by a cation M$^\oplus$ (where M$^\oplus$ is a non-chromophoric cation for example Na$^\oplus$, K$^\oplus$ or NH$_4^\oplus$) or by a protonated basic non-cationic group or by a cationic group in the molecule.

Unless otherwise indicated the preferred significance of a variable applies to that variable regardless of where the variable is set forth in the specification.

Any aliphatic amine group is preferably a mono $C_{1-4}$alkyl- or a di-($C_{1-4}$alkyl)amino group. Each alkyl group independently may be substituted by 1 to 3 substituents independently selected from halogen, phenyl, hydroxy and $C_{5-6}$cycloalkyl, but is preferably unsubstituted or monosubstituted by phenyl or hydroxy, any hydroxy being other than in the α-position.

Any cycloaliphatic amine group present is preferably $C_{5-6}$cycloalkylamine, the cycloalkyl group of which may be substituted by one or two $C_{1-2}$alkyl groups.

Any aromatic amine group present is preferably aniline, the phenyl ring of which is unsubstituted or substituted by one to three substituents selected from $C_{1-4}$alkyl, $C_{1-4}$alkoxy, halogen, hydroxy and phenoxy.

Any heterocyclic amino group present (or 5- or 6-membered heterocyclic ring) is preferably a pyridine, triazine, pyridazine, pyrimidine, or pyrazine group or a group of the formula

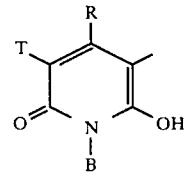

(when unsaturated) or a morpholine, pyrrolidine, piperidine, piperazine group (when saturated). Each group may be substituted by one to three R$_6$ groups, R is preferably R' where R' is methyl, ethyl, unsubstituted phenyl, unsubstituted benzyl or unsubsticyclohexyl. More preferably R is R″ where R″ is methyl or unsubstituted phenyl.

T is preferably T′ where T′ is hydrogen, cyano,

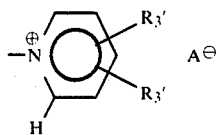

or CON(R$_5$′)$_2$, where R$_3$′ and R$_5$′ are defined below. More preferably T is T″ where T″ is cyano or

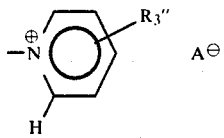

where R$_3$″ is defined below.

B is preferably B′ where B′ is —A′—NH—R$_2$′, hydrogen, —CH$_3$, —C$_2$H$_5$, —C$_2$H$_4$OH, unsubstituted cyclohexyl, benzyl, —(CH$_2$)$_{1-3}$N(R$_7$′)$_2$ or —(CH$_2$)$_{2-3}$N$^⊕$(R$_8$′)$_2$R$_9$′A$^⊖$, where the symbols are defined below. B is more preferably B″ where B″ is —A″—N-H—R$_2$″, hydrogen, —CH$_3$, —C$_2$H$_5$, benzyl, —(CH$_2$)$_b$N(R$_7$″)$_2$ or —(CH$_2$)$_b$—N$^⊕$(R$_8$)$_2$R$_9$A$^⊖$, where the symbols are defined below and b is 2 or 3.

R$_1$ is preferably R$_1$′ where R$_1$′ is

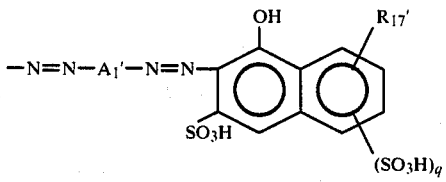

or when B is —A—NH—R$_2$, hydrogen or —N=N—D′; and where the symbols are defined below.

Preferably A is A′ where A′ is C$_{2-8}$alkylene or unsubstituted phenylene. More preferably A is A″ where A″ is 1,2-ethylene, 1,3-propylene or unsubstituted meta or para phenylene.

Preferably R$_2$ is R$_2$′ where R$_2$′ is a group of formula

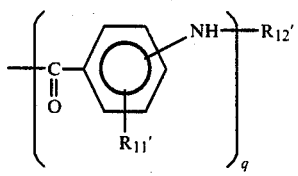

where the symbols R$_{11}$′ and R$_{12}$′ are defined below. More preferably R$_2$ is R$_2$″ where R$_2$″ is

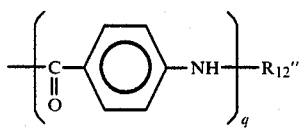

where R$_{12}$″ is defined below.

Preferably R$_3$ is R$_3$′ where R$_3$′ is hydrogen, methyl, ethyl, —NH$_2$ or —N(CH$_3$)$_2$. More preferably R$_3$ is R$_3$″ where R$_3$″ is hydrogen or methyl.

Preferably R$_5$ is R$_5$′ where R$_5$′ is hydrogen, methyl or ethyl. Preferably R$_5$″ is hydrogen or methyl.

Preferably R$_6$ is R$_6$′ where R$_6$′ is methyl or ethyl.

Preferably R$_7$ is R$_7$′ where R$_7$′ is hydrogen, linear or branched C$_{1-6}$alkyl, unbranched hydroxy C$_{2-3}$alkyl, benzyl, 2-cyanoethyl or both R$_7$′'s together with the N-atom to which they are attached form an unsubstituted pyrrolidine, piperidine, morpholine, piperazine or N-methylpiperazine group.

More preferably R$_7$ is R$_7$″ where R$_7$″ is hydrogen, methyl, ethyl, 2-hydroxyethyl or both R$_7$″'s together with the N-atom to which they are attached form an unsubstituted morpholine, piperidine, piperazine or N-methylpiperazine group;

Preferably R$_8$ is R$_8$′ where R$_8$′ is one of the significances of R$_7$′ except hydrogen and R$_9$ is R$_9$′ where R$_9$′ is methyl, ethyl, propyl or benzyl or both R$_8$'s and R$_9$′ together with the N-atom to which they are attached from a pyridinium ring unsubstituted or substituted by one or two methyl groups or a group β

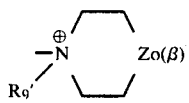

where Z$_o$ is —O—, a direct bond, —CH$_2$—, —NH—,

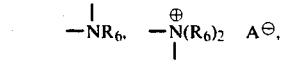

—SO$_2$—, —SO— or —S—. More preferably R$_8$ is R$_8$″ where R$_8$″ is one of the significances of R$_7$″ except hydrogen and R$_9$ is R$_9$″ where R$_9$″ is —CH$_3$, —C$_2$H$_5$ or benzyl or both R$_8$″ and R$_9$″ together with the N-atom to which they are attached form a pyridinium ring, unsubstituted or substituted by one or two methyl groups, or is a group β defined above.

Preferably R$_{11}$ is R$_{11}$′ where R$_{11}$′ is hydrogen, chloro, nitro, methyl or methoxy.

Preferably R$_{12}$ is R$_{12}$′ where R$_{12}$′ is

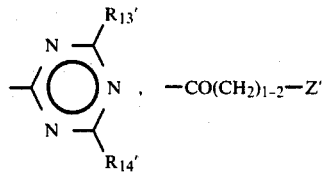

or hydrogen;

More preferably R$_{12}$ is R$_{12}$″ where R$_{12}$″ is —CO—CH$_2$—Z″ or

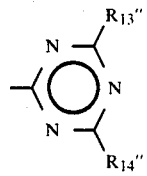

where $R_{13}''$, $R_{14}''$ and $Z''$ are defined below. Preferably $R_{13}$ is $R_{13}'$ where $R_{13}'$ is chloro, —OH, —NH$_2$,

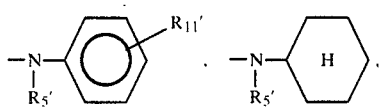

N,N-di-(C$_{2-4}$hydroxyalkyl)amino,

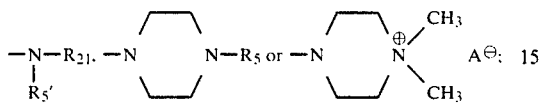

where $R_{21}$ is unsubstituted C$_{1-12}$alkyl; or C$_{2-12}$alkyl substituted by —OH; C$_{3-12}$alkyl interrupted by one to three groups selected from —N(R$_7$)— and

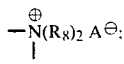

—NHCOCH$_2$—Z; —CH$_2$CONH—Y$_1$—Z, —Y$_1$—Z;

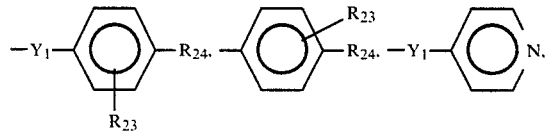

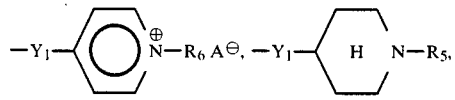

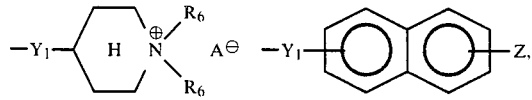

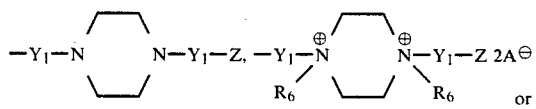

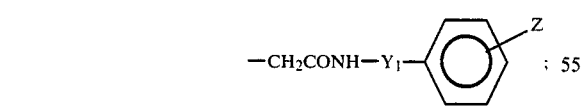

where
Y$_1$ is a C$_{1-8}$alkylene or a C$_{3-8}$alkenylene group;
Z is —N(R$_7$)$_2$ or —N$^⊕$(R$_8$)$_2$R$_9$A$^⊖$;
R$_{23}$ is halogen, —OH, —NO$_2$, C$_{1-4}$alkyl or C$_{1-4}$alkoxy;
R$_{24}$ is, —N(R$_7$)$_2$, —N$^⊕$(R$_8$')$_2$R$_9$'A$^⊖$ or —CO—Y$_2$—Z', —NHCO—Y$_2$—Z', —CONH—Y$_2$—Z', —SO$_2$NH—Y$_2$—Z', —Y$_2$—Z' or —NHNHCOCH$_2$—Z',
where Y$_2$ is C$_{1-8}$alkylene.
More preferably $R_{13}$ is $R_{13}''$, where $R_{13}''$ is

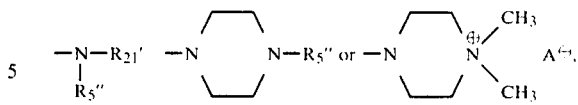

where
$R_{21}'$ is
—(CH$_2$)$_{2-3}$—N(R$_7''$)—(CH$_2$)$_{2-3}$—N(R$_7''$)R$_6'$,
—(CH$_2$)$_{2-3}$—N$^⊕$(R$_8''$)$_2$—(CH$_2$)$_{2-3}$—N$^⊕$(R$_8''$)$_2$R$_6'$-2A$^⊖$,
—(CH$_2$)$_{2-3}$—N(R$_7''$)—C$_2$H$_5$,
—(CH$_2$)$_{2-3}$—N$^⊕$(R$_8''$)$_2$—C$_2$H$_5$A$^⊖$,
—NHCOCH$_2$—Z'',
—CH$_2$—CONH—Y$_2'$—Z'',

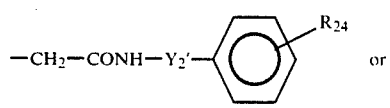

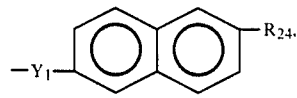

where
R$_6'$ is methyl or ethyl, and
Y$_2'$ is C$_{1-4}$alkylene.
Preferably Z is Z' where Z' is —N(R$_7'$)$_2$ or —N$^⊕$(R$_8'$)$_2$R$_9'$A$^⊖$.
More preferably Z is Z'' where Z'' is N(R$_7'$)$_2$ or —N$^⊕$(R$_8''$)$_2$R$_9''$A$^⊖$.
Preferably $R_{14}$ is $R_{14}'$ where $R_{14}'$ is therefore

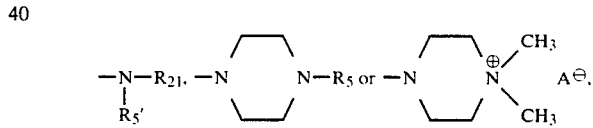

where R$_5$, and R$_{21}$ are defined above. More preferably $R_{14}$ is $R_{14}''$ where $R_{14}''$ is —NR$_5''$R$_{21}'$,

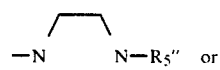

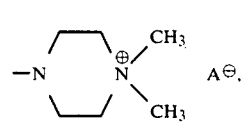

Preferably R$_{19}$ is hydrogen.
Preferably D is D' where D' is

9

-continued

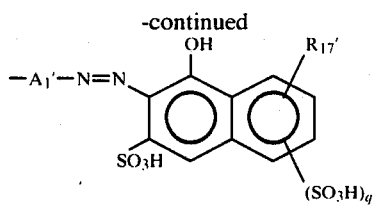

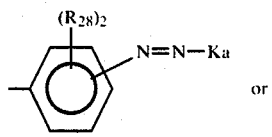

or

10

-continued

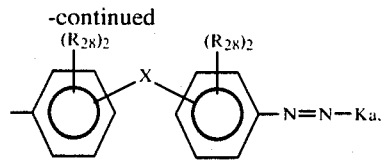

where each $R_{26}$, independently, is hydrogen, halogen, —$NO_2$, —$NH_2$, $C_{1-4}$alkyl, $C_{1-4}$alkoxy, —CN, trifluoromethyl, phenyl, anilino, benzoyl, carbamoyl, phenoxy, halophenoxy, dihalophenoxy, $C_{1-4}$alkylsulphonyl, phenylsulphonyl, $C_{1-4}$alkylsulphonylamino or N,N-di($C_{1-4}$alkyl)-aminosulphonyl;

each $R_{28}$ independently, is hydrogen, halogen, $C_{1-4}$-alkyl or $C_{1-4}$alkoxy and X is any one of $X_1$ to $X_{64}$ and $X_{100}$ to $X_{108}$ below: $X_1$ a direct bond, $X_2$, linear or branched $C_{1-4}$alkylene,

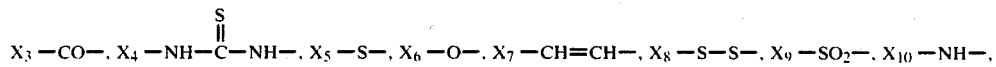

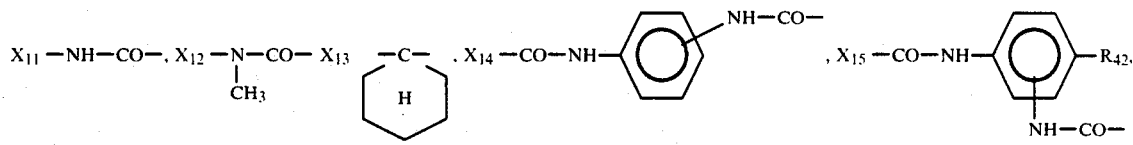

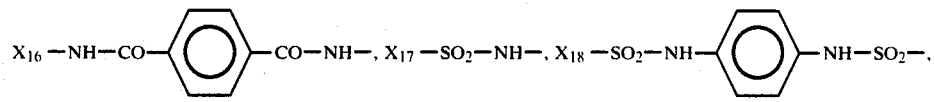

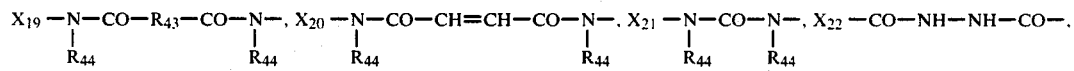

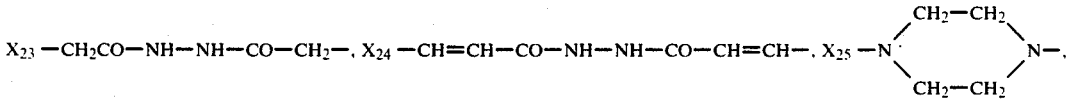

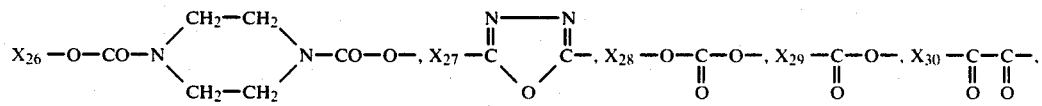

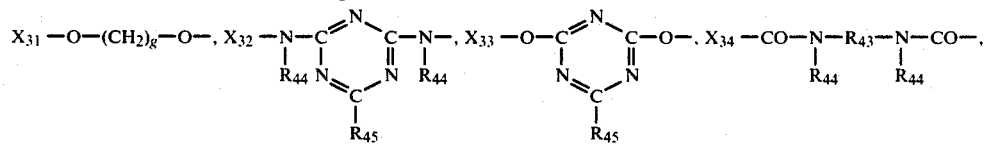

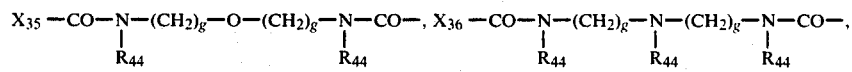

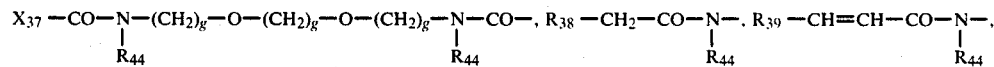

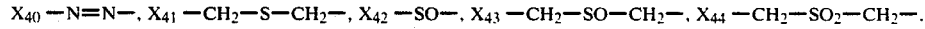

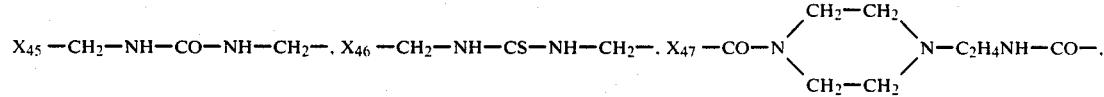

-continued
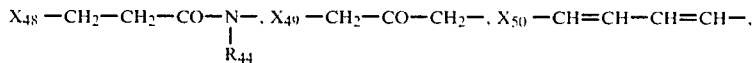
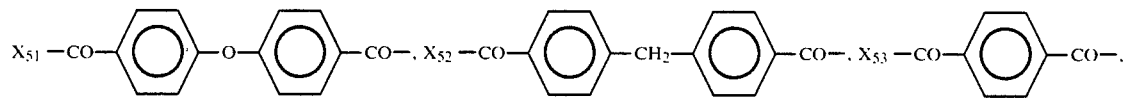
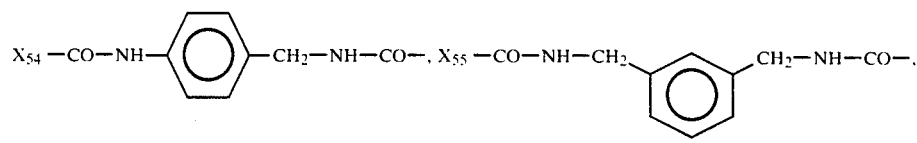
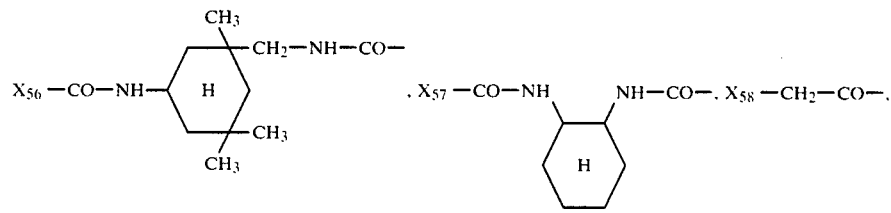
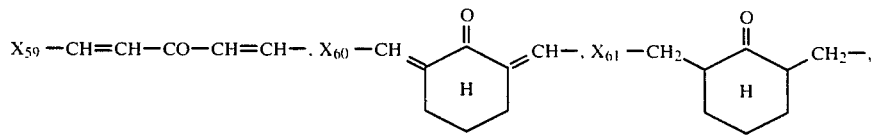
$X_{64}$—CO—NH—$R_{43}$—CO—NH—, Preferably X is X' where X' is $X_{70}$—NH—CO—NH—,
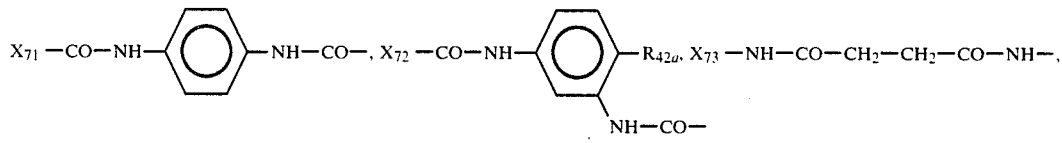
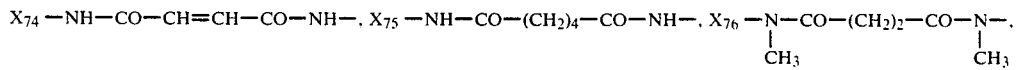
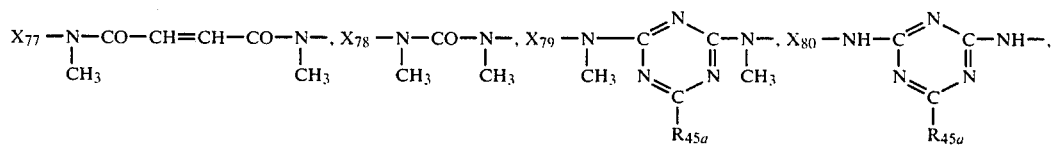
$X_{81}$—$CH_2$—, $X_{82}$—$(CH_2)_2$—, $X_{83}$—$(CH_2)_3$—, $X_{84}$—$(CH_2)_4$—, $X_{85}$—CO—NH—$(CH_2)_2$—NH—CO—,
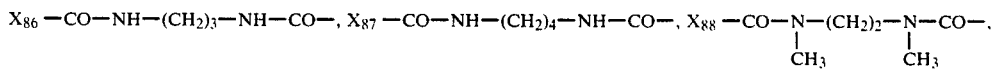
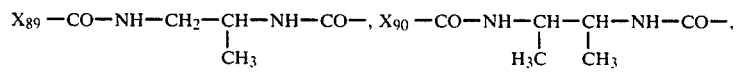
$X_{100}$—CO—NH—$R_{43}$—CO—NH—$R_{43}$—NH—CO—, $X_{101}$—CO—NH—$R_{43}$—NH—CO—$CH_2$—$CH_2$—CO—NH—$R_{43}$—NH—CO—.
$X_{102}$—CO—NH—$R_{43}$—NH—CO—CH=CH—CO—NH—$R_{43}$—NH—CO—,
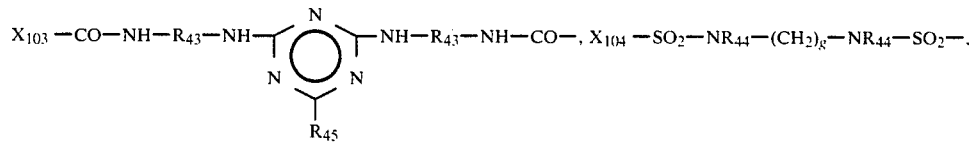

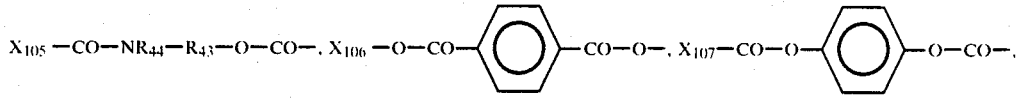

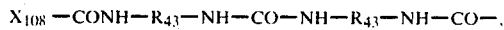

each $R_{42}$ independently is halogen, $C_{1-4}$alkyl or $C_{1-4}$alkoxy, each $R_{43}$ independently is linear or branched $C_{1-4}$alkylene, each $R_{44}$ independently is hydrogen or $C_{1-4}$alkyl group, each $R_{42a}$ independently is hydrogen, Cl, —$CH_3$ or —$OCH_3$, each $R_{45a}$ independently is Cl, —$NH(CH_2)_2OH$, $OCH_3$, —$OC_2H_5$, —OH, —$NH_2$, —$N(CH_2$—$CH_2OH)_2$, $$-\underset{H}{N}-(CH_2)_3N(C_2H_5)_2,$$

each $R_{45}$ independently, is halogen, —NH—$CH_2$—$CH_2$—OH, —$N(CH_2$—$CH_2$—OH$)_2$, —$NH_2$, —OH, —NH—$(CH_2)_{2-3}N(C_2H_5)_2$,

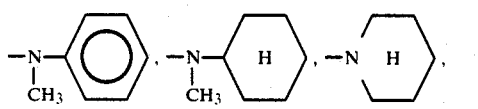

—$OCH_3$ or —$OC_2H_5$ and g is 1, 2, 3 or 4, preferably 2, 3 or 4.

More preferably X, when one of $R_{28}$ is not hydrogen, is a direct bond, $X_2$, $X_{14}$, $X_{21}$, $X_{32}$ or $X_{40}$.

Preferably when any phenyl ring to which X is attached is substituted, the substituent is in an ortho position to the azo radical attached to the said ring.

Ka is a diazo or coupling component of the pyrazolone, 5 series, 5-aminopyrazole series, α- or β-naphthol series, aniline series, phenol series, α- or β-aminonaphthalene series, aminonaphthol series, acetoacetyl alkyl or arylamide series, barbituric acid or dimedone series or diaminopyridine series or is

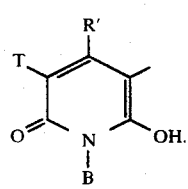

In the various component series mentioned above the component may be substituted by such groups as $R_1$ to $R_{40}$ hereinbefore or hereinafter defined.

Preferably Ka is Ka' where Ka' is a group of any one of the formulae (a) to (l) below

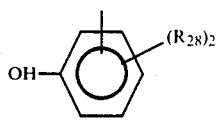 (a)

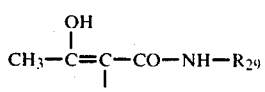 (b)

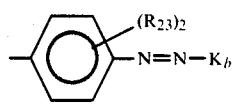 (c)

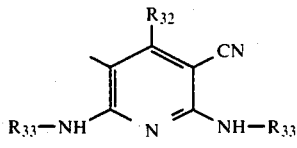 (d)

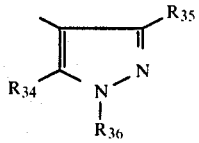 (e)

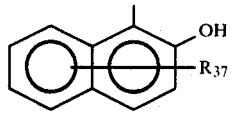 (f)

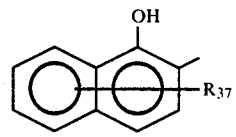 (g)

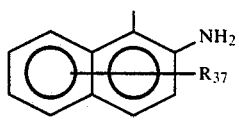 (h)

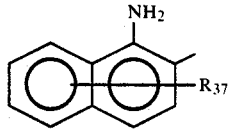 (i)

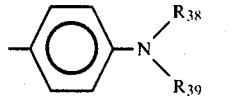 (j)

-continued (R$_{40}$)$_2$ phenyl group pyridone structure with R', T', CH$_3$, OH, O, N-B'

More preferably D is D" where D" is (R$_{26}$)$_2$ phenyl group (R$_{28}$)$_2$ phenyl–N=N–K$_a''$ $-A_1'-N=N-$ naphthalene with OH, R$_{17}'$, SO$_3$H or (R$_{28}$)$_2$ phenyl–X'–phenyl(R$_{28}$)$_2$–N=N–K$_a''$ where each R$_{28}$ independently is hydrogen, halogen, C$_{1-4}$-alkyl or C$_{1-4}$alkoxy, X' is defined above and K$_a''$ is defined below.

K$_a$ is more preferably K$_a''$ where K$_a''$ is a group of one of the formulae a$_1$ to k$_1$ below:

(a$_1$) phenyl–OH (b$_1$) CH$_3$–C(OH)=C–C(=O)–NH–R$_{29}'$ (c$_1$) (R$_{28}$)$_2$ phenyl–N=N–K$_b'$ (d$_1$) pyridone with R', T', CH$_3$, OH, N-B', =O (e$_1$) pyridine with CH$_3$, CH$_3$, CN, R$_{33}'$–NH, NH–R$_{33}'$ (f$_1$) pyrazole with CH$_3$, CH$_3$, R$_{34}$, N, N–R$_{36}'$ (g$_1$) naphthalene with CH$_3$, OH, (R$_{37}'$)$_q$, (R$_{37}'$)$_{1-q}$ (h$_1$) naphthalene with OH, CH$_3$, R$_{37}'$ (i$_1$) naphthalene with CH$_3$, NH$_2$, R$_{37}'$ (j$_1$) phenyl–N(R$_{39}'$)(R$_{38}'$)

(k$_1$) (R$_{40}$)$_2$ phenyl where R$_{29}$ is a group $-(CH_2)_m-Z$, phenyl with R$_{46}$, (R$_{47}$)$_2$ (CH$_3$)$_q$ benzothiazole –C–(phenyl)$_q$ (CH$_3$)$_q$ benzimidazole –C–   (CH$_3$)$_q$ benzoxazole –C–

(CH$_3$)$_q$ phenyl–benzothiazole–benzothiazole–(CH$_3$)$_q$ or

-continued

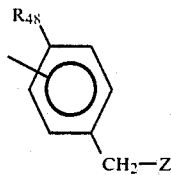

where
R$_{46}$ is hydrogen,

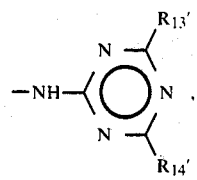

—NHCO(CH$_2$)$_{2-3}$—Z, —SO$_2$NH(CH$_2$)$_{2-3}$—Z or —CO—Y$_1$—Z;

each R$_{47}$ independently is hydrogen, halogen, C$_{1-4}$alkyl, C$_{1-4}$alkoxy, —NO$_2$ or —CN;

R$_{48}$ is C$_{1-4}$alkoxy and each q, independently, is 0 or 1 and R$_{13}'$, R$_{14}'$, Y$_1$ and Z are defined above, R$_{32}$ is C$_{1-4}$alkyl or phenyl;

each R$_{33}$ independently is hydrogen, C$_{1-4}$alkyl, —(CH$_2$)$_{2-3}$OCH$_3$, —(CH$_2$)$_2$OH, —(CH$_2$)$_{2-3}$N(CH$_3$)$_2$ or —(CH$_2$)$_{2-3}$N$^\oplus$(CH$_3$)$_3$A$^\ominus$. R$_{33}$ is preferably R$_{33}'$ where R$_{33}'$ is hydrogen, —(CH$_2$)$_2$OH, —(CH$_2$)$_3$—OCH$_3$, —(CH$_2$)$_{2-3}$—N(CH$_3$)$_2$ or —(CH$_2$)$_{2-3}$N$^\oplus$(CH$_3$)$_3$A$^\ominus$;

R$_{34}$ is —OH or —NH$_2$;

R$_{35}$ is C$_{1-4}$alkyl, —COOR$_6$, —CON(R$_{5a}$)$_2$ or —CONH—Y$_1$—Z, wherein each R$_{5a}$ is independently C$_{1-4}$alkyl or hydrogen, and R$_6$ is C$_{1-4}$alkyl;

R$_{36}$ is hydrogen,

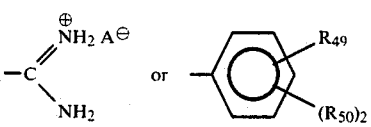

where
R$_{49}$ is hydrogen, —CONH—Y$_1$—Z, —SO$_2$—NH—Y$_1$—Z, —NHCO(CH$_2$)$_{2-3}$—Z or

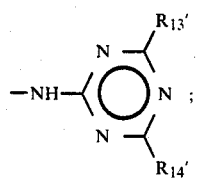

each R$_{50}$ independently is hydrogen, halogen, C$_{1-4}$alkoxy, —NO$_2$; —NH$_2$ or C$_{1-4}$alkyl, R$_{37}$ is

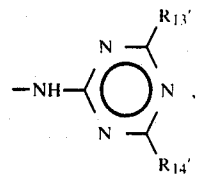

—NHCO(CH$_2$)$_{1-3}$—Z, —SO$_2$NH—Y$_1$—Z, —CONH—Y$_1$—Z, —CONHNH$_2$, —NH—Y$_1$—Z, —CH$_2$—Z,

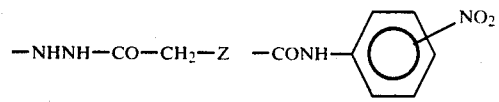

or hydrogen;
R$_{38}$ is C$_{1-4}$alkyl,

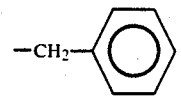

or —(CH$_2$)$_2$CN;

preferably R$_{38}$ is R$_{38}'$ where R$_{38}'$ is —CH$_3$, —C$_2$H$_5$, —(CH$_2$)$_2$CN or benzyl;

R$_{39}$ is C$_{1-4}$alkyl or —(CH$_2$)$_m$—Z; preferably R$_{39}$ is R$_{39}'$ where R$_{39}'$ is —CH$_3$, C$_2$H$_5$, or —(CH$_2$)$_{m'}$—Z, R$_{40}$ is hydrogen, C$_{1-4}$alkyl or C$_{1-4}$alkoxy;

m is an integer 1 to 6 and m is preferably m' where m' is an integer from 2 to 4;

K$_b$ is a component of formula (a), (b) or (d) to (l) of component K$_a'$ and K$_b'$ is a component (a$_1$), (b$_1$) or (d$_1$) to (k$_1$), Preferably R$_{29}$ is R$_{29}'$ where R$_{29}'$ is —(CH$_2$)$_{m'}$—Z',

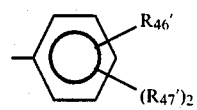

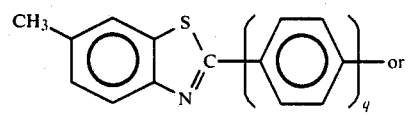

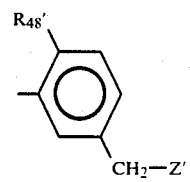

where
R$_{46}'$ is hydrogen,

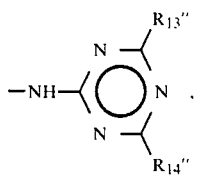

—NHCO(CH$_2$)$_{2-3}$—Z'  or  —SO$_2$—NH—(CH$_2$)$_{2-3}$—Z';

each R$_{47}$' independently is hydrogen, chlorine, bromine, methyl, ethyl, methoxy, ethoxy, —NO$_2$ or —CN;

R$_{48}$' is methoxy or ethoxy; and m' is 2, 3 or 4.

Preferably K$_1$ is K$_1$' where K$_1$' is a group of the formula

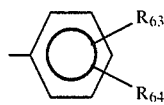

where R$_{63}$ and R$_{64}$ are later defined or has a significance of K$_a$' (independently of K$_a$').

More preferably K$_1$ is K$_1$" where K$_1$" is a group of the formula

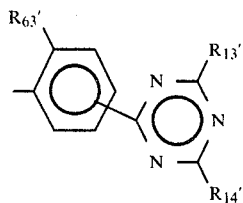

where R$_{63}$' is later defined and R$_{13}$' and R$_{14}$' are defined above or has a significance of K$_a$" (independently of K$_a$").

Most preferably K$_1$ is K$_a$''' where K$_a$''' is a group of the formula

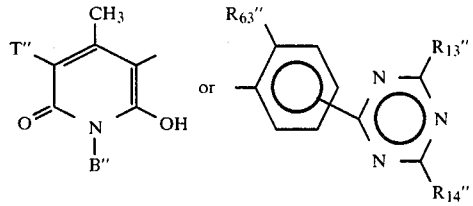

where the symbols are defined above except R$_{63}$" which is defined below.

Preferably A$_1$ or A$_{10}$ is A$_1$' where A$_1$' is

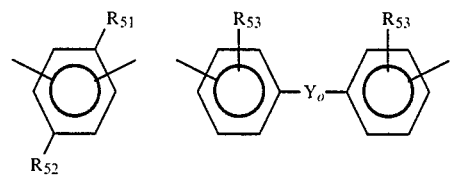

or

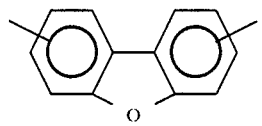

where

R$_{51}$ is hydrogen, halogen, C$_{1-4}$alkyl or C$_{1-4}$alkoxy;

R$_{52}$ is —OH, halogen, —CN, —CONH$_2$, —NHCOC$_{1-4}$alkyl, —NHCONH$_2$, —COOH, —SO$_3$H, hydrogen, C$_{1-4}$alkyl or C$_{1-4}$alkoxy;

each R$_{53}$ independently is hydrogen, halogen, —CN, C$_{1-4}$alkyl, C$_{1-4}$alkoxy, —COOH, —SO$_3$H or —OH;

Yo is a direct bond, (CH$_2$)$_{1-3}$, —O—, —S—, —SO$_2$—, —NH—CO—, —NH—CONH—, —NH—CO—(CH$_2$)$_{2-3}$—, —CONH—, —CONH(CH$_2$)$_{2-3}$NHCO—, —O—(CH$_2$)$_{2-3}$—O—, —N=N— or —CH=CH—CO—CH=CH—.

More preferably A$_1$ or A$_{10}$ is A$_1$" where A$_1$" is

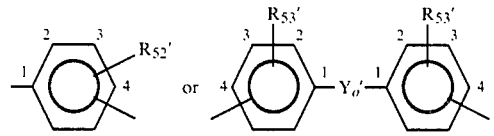

where

R$_{52}$' is hydrogen, chlorine, —OH, methyl or methoxy;

R$_{53}$' is hydrogen, —Cl, —CH$_3$, —OH or —OCH$_3$;

Y'o is a direct bond, —NH—CO— or —NHCONH—.

Preferably in A$_1$" the free bonds shown are in a meta or para position to each other (in the phenyl ring) or to Y$_o$ (in the Y$_o$-containing group).

In the compounds of formula I preferably 0 to 4 sulpho groups are present, more preferably up to 2 sulpho groups are present.

Preferably X$_o$ is X$_o$' where X$_o$' is —NH—, —NHCONH—, —NHCOCH=CHCONH—, —NHCO(CH$_2$)$_{2-3}$CONH—,

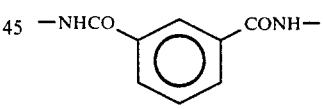

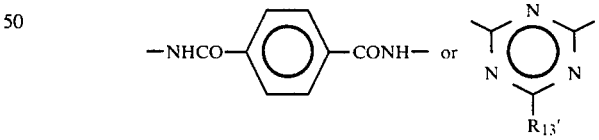

where R$_{13}$' is defined above.

More preferably X$_o$ is X$_o$" where X$_o$" is —NH—, —NHCOCH=CHCONH— or —NHCO(CH$_2$)$_2$CONH—.

Preferably, R$_{17}$ is R$_{17}$', where R$_{17}$' is hydrogen,

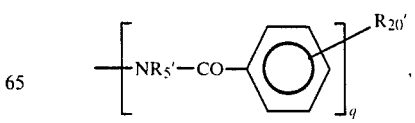

—N=N—K$_1$'; —N=N—A$_1$'—N=N—K$_1$' or

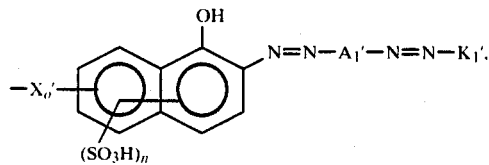

$R_{20}'$ is —NR$_5'$—Q$_1$—N(R$_7'$)$_2$, —NR$_5'$—Q$_2$—N$^\oplus$(R$_8'$)$_2$R$_9'$A$^\ominus$ or

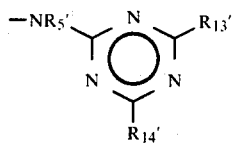

and the other symbols are defined above.

More preferably, R$_{17}$ is R$_{17}''$, where R$_{17}''$ is hydrogen,

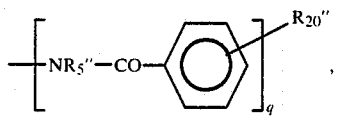

—N=N—K$_1''$, —N=N—A$_1'$—N=N—K$_1''$ or

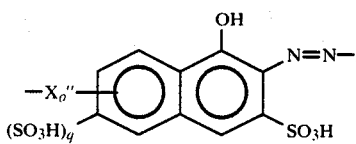

$R_{20}''$ is —NR$_5''$—Q$_1$—N(R$_7''$)$_2$, —NR$_5''$—Q$_2$—N$^\oplus$(R$_8''$)$_2$R$_9''$A$^\ominus$ or

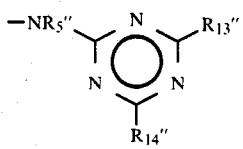

and the other symbols are defined above.

Preferably Q$_1$ is C$_{2\text{-}6}$alkylene, more preferably C$_{2\text{-}3}$alkylene, most preferably C$_3$ alkylene.

Preferably R$_{33}$ is R$_{33}'$ where R$_{33}'$ is hydrogen, —(CH$_2$)$_2$OH, —(CH$_2$)$_3$OCH$_3$, —(CH$_2$)$_{2\text{-}3}$=N(CH$_3$)$_2$ or —(CH$_2$)$_{2\text{-}3}$—N$^\oplus$(CH$_3$)$_3$A$^\ominus$.

Preferably R$_{36}$ is R$_{36}'$ where R$_{36}'$ is hydrogen,

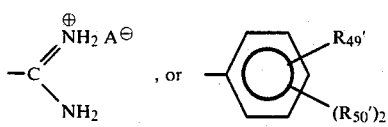

where
R$_{49}'$ is hydrogen, —CO—NH—(CH$_2$)$_m'$—Z'; —NH-CO(CH$_2$)$_{2\text{-}3}$—Z' or

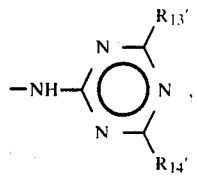

each R$_{50}'$ independently is hydrogen, chlorine, methyl or methoxy.

Preferably R$_{37}$ is R$_{37}'$ where R$_{37}'$ is

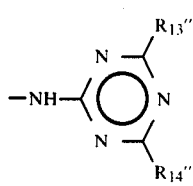

Further according to the invention there are provided azo compounds, in metal-free, 1:1 or 1:2 metal complex form, in free acid or acid addition salt form of formula II

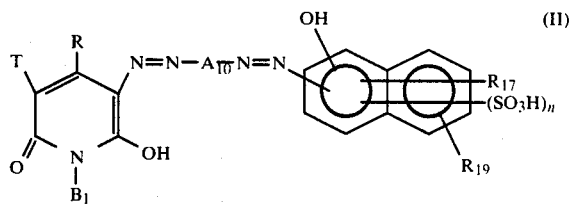

(II)

in which B$_1$ is hydrogen, C$_{1\text{-}4}$alkyl, C$_{2\text{-}4}$alkyl substituted by hydroxy, C$_{5\text{-}6}$cycloalkyl unsubstituted or substituted by 1 or 2 methyl groups, phenyl(C$_{1\text{-}3}$alkyl), —A$_4'$—N(R$_7$)$_2$, —A$_4$—N$^\oplus$(R$_8$)$_2$R$_9$A$^\ominus$ or —N(R$_7$)$_2$, and where the other symbols are defined above.

Preferred compounds of formula II are of formula IIa in metal-free, 1:1 or 1:2 metal complex form

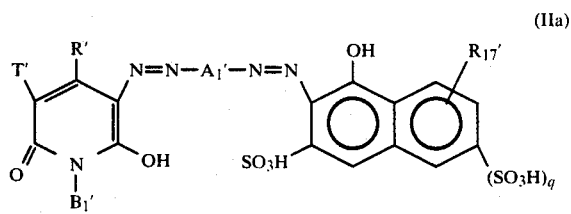

(IIa)

where B$_1'$ is hydrogen, —CH$_3$, —C$_2$H$_5$, —C$_2$H$_4$OH, cyclohexyl, benzyl, —(CH$_2$)$_{2\text{-}3}$—N(R$_7''$)$_2$ or —(CH$_2$)$_{2\text{-}3}$—N$^\oplus$(R$_8''$)$_2$R$_9''$A$^\ominus$, and where the other symbols are defined above.

Preferred compounds of formula IIa are of formula (IIa') in metal-free, 1:1 or 1:2 metal complex form

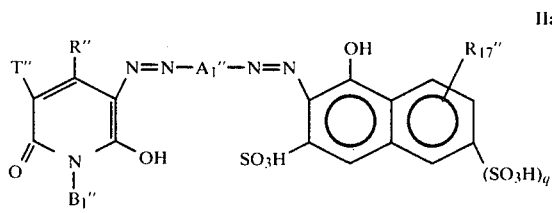

in which $B_1''$ is hydrogen, —CH$_3$, —C$_2$H$_5$, benzyl, —(CH$_2$)$_{2-3}$—N(R$_7''$)$_2$ or —(CH$_2$)$_{2-3}$—N$^\oplus$(R$_8''$)$_2$R$_9''$A$^\ominus$, where the symbols are defined above.

Alternatively, preferred compounds of formula II are of formula IIb in metal-free, 1:1 or 1:2 metal complex form

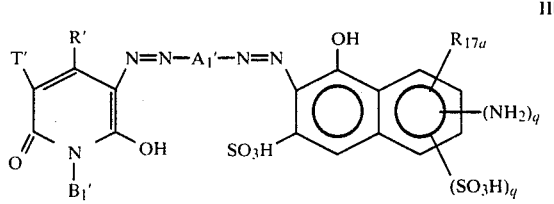

where $R_{17a}$ is —N=N—K$_1'$, —N=N—A$_1'$—N=N—K$_1'$ or

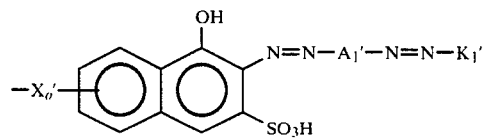

where the symbols are defined above.

Preferred compounds of formula IIb are those in which $R_{17a}$ is $R_{17a}'$ where $R_{17a}'$ is

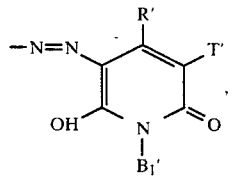

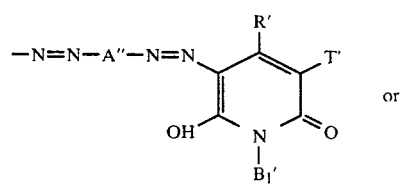

or

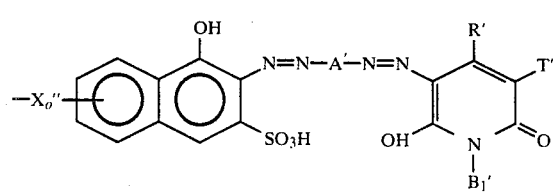

Alternatively, preferred compounds of formula (I) are of formula III in metal-free, 1:1 or 1:2 metal complex form, in free acid or acid addition salt form

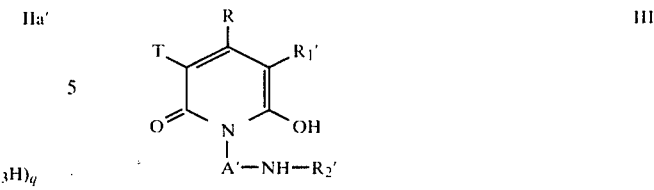

where $R_1'$ is hydrogen or —N=N—D (more preferably —N=N—D) and the other symbols are as defined above.

Preferred compounds of formula III are of formula IIIa

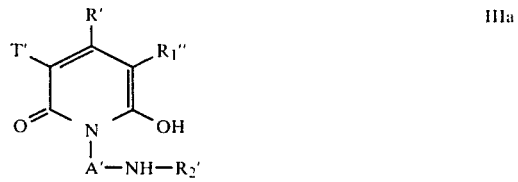

where $R_1''$ is hydrogen or —N=N—D' (more preferably —N=N—D') and the other symbols are defined above. Compounds of formula IIIa are in metal-free, 1:1 or 1:2 metal complex form where $R_1''$ is —N=N—D'.

More preferred compounds of formula III are of formula IIIb

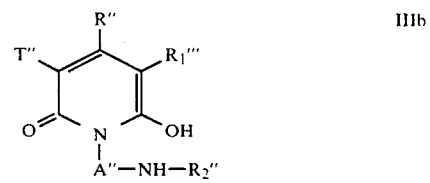

where $R_1'''$ is hydrogen or —N=N—D'' and the other symbols are defined above. Compounds of formula IIIb are in metal-free, 1:1 or 1:2 metal complex form when $R_1'''$ is —N=N—D''.

Preferred compounds of formula IIIb are of formula IIIc

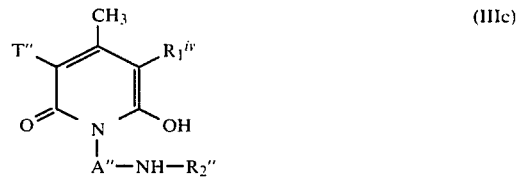

where $R_1^{iv}$ is hydrogen or —N=N—D''' where D''' is

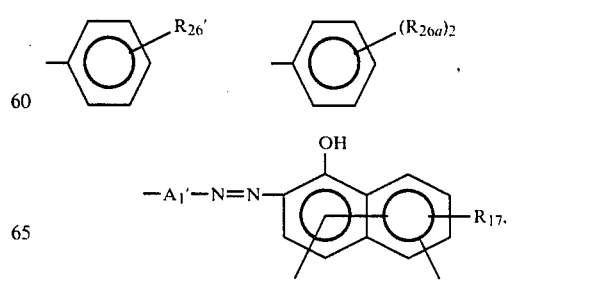

-continued

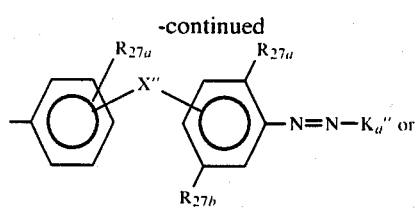 —N=N—K$_a''$ or

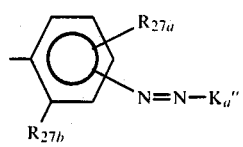

where
R$_{26}'$ is hydrogen, —NO$_2$, chloro, methyl, methoxy or chlorophenoxy;
R$_{27a}$ is hydrogen, chloro, methyl or methoxy;
R$_{27b}$ is hydrogen, methyl or methoxy;
each R$_{26a}$ is independently nitro, chloro, methoxy or methyl;
X″, when both the substituents R$_{27a}$ and R$_{27b}$ are hydrogen, is X$_1$, X$_5$, X$_6$, X$_7$, X$_{10}$, X$_{11}$, X$_{12}$, X$_{16}$, X$_{17}$, X$_{22}$, X$_{25}$, X$_{26}$, X$_{27}$, X$_{30}$, X$_{31}$, X$_{49}$, X$_{50}$, X$_{51}$, X$_{52}$, X$_{53}$, X$_{54}$, X$_{58}$, X$_{59}$, X$_{64}$, X$_{70-90}$, X$_{101}$ where R$_{43}$=—(CH$_2$)$_{1-2}$, X$_{103}$ (where R$_{43}$ is —(CH$_2$)$_{1-2}$ and R$_{45}$ is NH(CH$_2$)$_{2-3}$—N(C$_2$H$_5$)$_2$), X$_{104}$ (where R$_{44}$ is hydrogen or g is 2 or 3) and X$_{108}$ (where R$_{43}$ is —(CH$_2$)$_{1-2}$—) and otherwise is X$_1$, X$_{40}$, X$_{70}$, X$_{71}$, X$_{80}$, X$_{81}$, X$_{82}$ or X$_{85}$. Compounds of formula IIIc are in metal-free, 1:1 or 1:2 metal complex form when R$_1{}^{iv}$ is —N=N—D‴.

Preferably when the phenyl rings to which X is attached are substituted, the substituents selected from chloro, methyl and methoxy are in an ortho position to the azo group attached to said rings.

Alternatively preferred compounds of formula I are of formula XIV in metal-free, 1:1 or 1:2 metal complex form;

one R$_{60}$ is —OH and the other R$_{60}$ is NH$_2$,
R$_{61}$ is hydrogen, C$_{1-4}$alkoxy or —OH
R$_{62}$ is hydrogen, chloro, nitro, C$_{1-4}$alkyl, C$_{1-4}$alkoxy or —OH,
R$_{63}$ has a significance of R$_{62}$ independently of R$_{62}$,
R$_{64}$ is hydrogen,

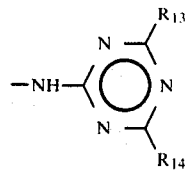

—N(CH$_3$)$_2$, —N$^\oplus$(CH$_3$)$_3$A$^\ominus$, —N(C$_2$H$_5$)$_2$, —N$^\oplus$(C$_2$H$_5$)$_3$A$^\ominus$, —CO—Y$_2$—Z, —CONH—Y$_2$—Z, —Y$_2$—Z, —NH—CO—Y$_2$—Z, —SO$_2$—NH—Y$_2$—Z or —NHNHCOCH$_2$—Z,
M is hydrogen or a non-chromophoric cation,
and the other symbols are defined above,
with the provisos that
(i) the number of cationic and protonatable basic groups exceeds the number of sulpho groups present by at least one;
(ii) R$_{64}$ is in the 3- or 4-position on the phenyl ring to which it is attached (the positions being as indicated).
Preferred compounds of formula XIV are of formula XIV′ in metal-free, 1:1 or 1:2 metal complex form;

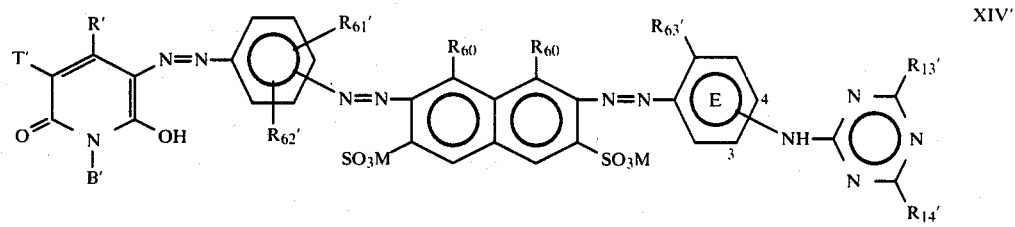

XIV′ in which
R$_{61}'$ is hydrogen, methoxy or —OH,
R$_{62}'$ is hydrogen, chloro or methyl,
R$_{63}'$ is hydrogen, methoxy, —OH, methyl or chloro,
and the other symbols are as defined above,
with the provisos that
(i) the number of cationic and protonable basic groups present exceeds the number of sulpho groups present by at least one;
(ii) the amino group on ring E is in the 3- or 4-position.
More preferred compounds of formula XIV are of

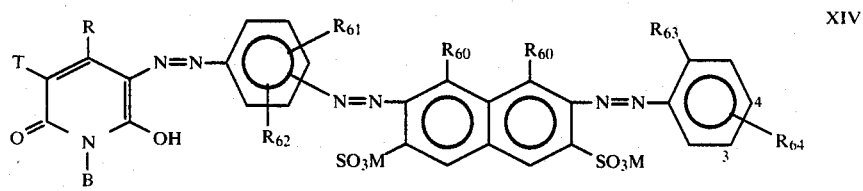

XIV in which formula XIV″ in metal-free, 1:1 or 1:2 metal complex form

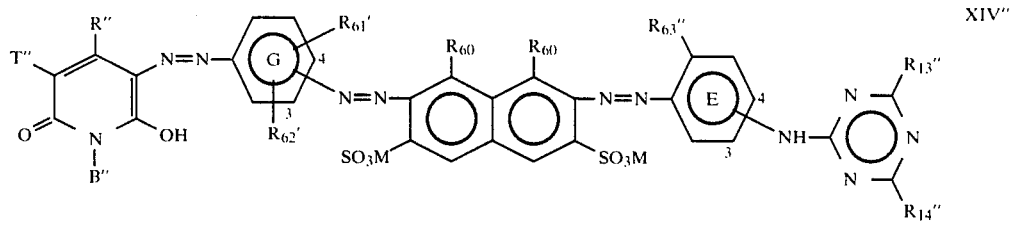 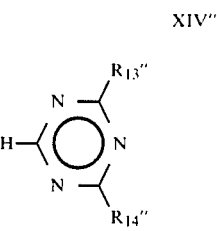

in which $R_{63}''$ is hydrogen, —OH or methoxy, and the other symbols are as defined above with the provisos that (i) the number of cationic and protonable basic groups exceeds the number of sulpho groups present by at least one;
(ii) that the amino group on ring E is in the 3- or 4-position (the positions being as indicated);
(iii) the azo group on ring G is in the 3- or 4-position (the positions being as indicated).

Preferred metallisable groups are —NH$_2$, —OH or —O(C$_{1-4}$alkyl) which are situated ortho to an azo bridge on a benzo or a phenyl group. Metallisation of such groups can be represented as follows:

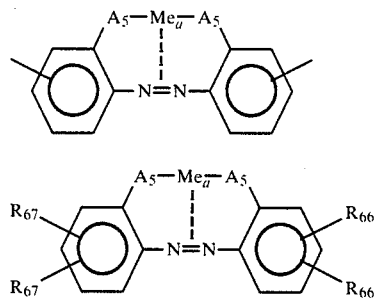

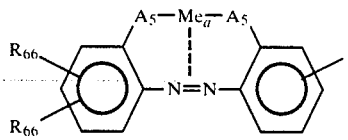

-continued

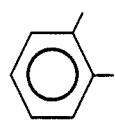

in which
each A$_5$ independently, is —O— or —NH—
Me$_a$ is a 1:1 or 1:2 metal complex forming metal, and both R$_{66}$'s and R$_{67}$'s are ortho to each other and together form an aromatic ring system (for example together with the two carbon atoms to which they are attached form a group).

Preferred compounds of formula I when in metallised form are of formulae IVa to IVi:

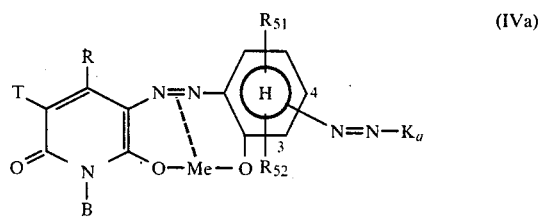 (IVa)

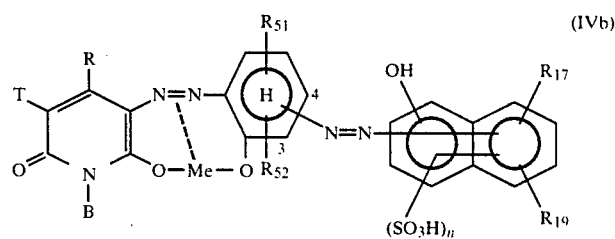 (IVb)

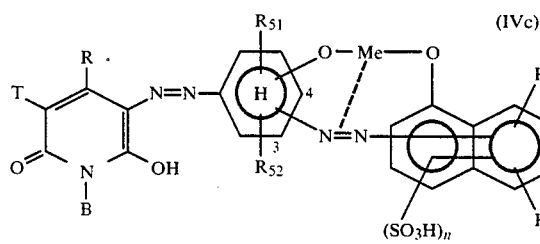 (IVc)

(IVd)

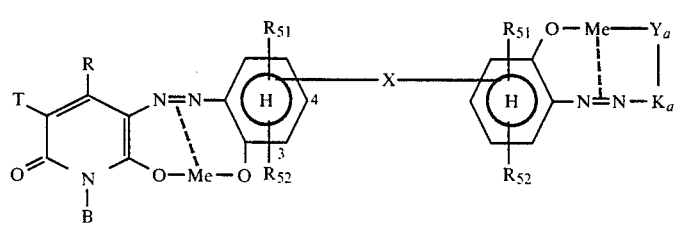 (IVe)

-continued

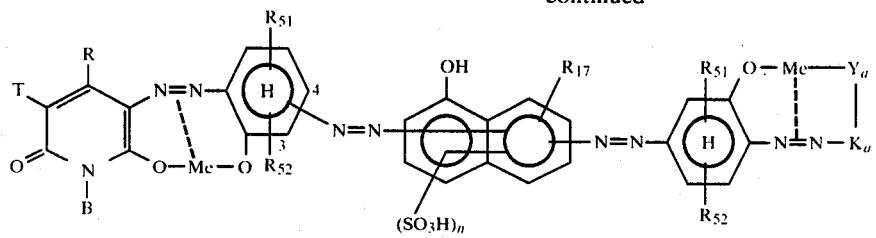 (IVf)

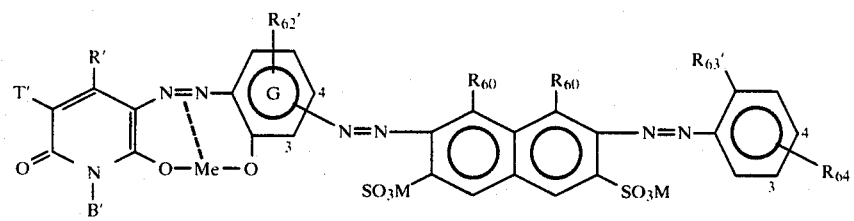 (IVg)

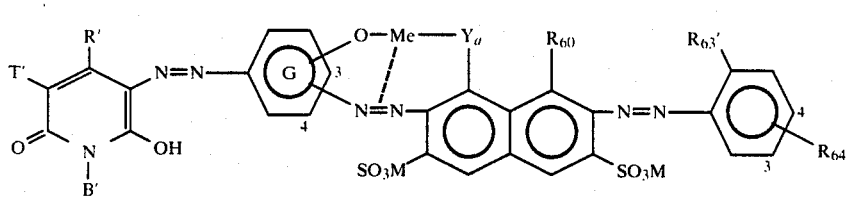 (IVh)

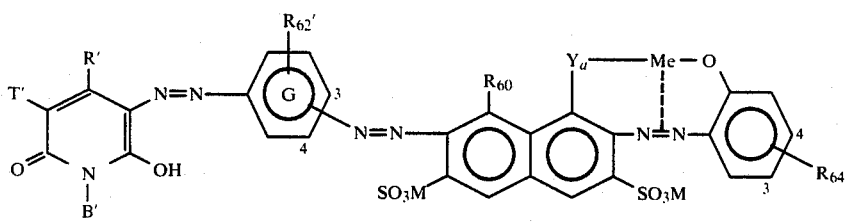 (IVi)

where
$Y_a$ is —O— or —NH—
Me is copper, chromium, cobalt, nickel, iron, manganese or zinc for 1:1 metal complexes (Me is preferably copper in this case) or Me is chromium, cobalt, iron or nickel for 1:2 metal complexes (Me is preferably iron in this case);
with the provisos that
(i) in the compounds of formulae IVg, IVh and IVi $R_{64}$ is in the 3- or 4-position, the naphthyl azo group on ring G is in the 3- or 4-position and the number of cationic and protonable basic groups present exceeds the number of sulpho groups present;
(ii) in the compounds of formula IVh the group —O—Me—O— is ortho to the naphthyl azo group; and
(iii) in the compounds of formulae IVh and IVi when $Y_a$ is —NH— then $R_{60}$ is —OH, and when $Y_a$ is —O— then $R_{60}$ is —NH₂.

The entire specification of parent application Ser. No. 06/485,212, filed Apr. 15, 1982 (including claims) is thereby incorporated by reference in its entirety.

Compounds of formula I where $R_1$ is hydrogen may be prepared by reacting a compound of formula V

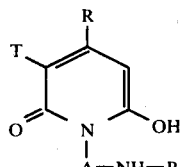 V

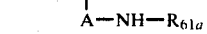

with a compound of formula $V_a$

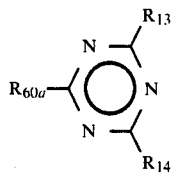 $V_a$ where $R_{60a}$ is halogen and $R_{61a}$ is hydrogen or a group of the formula

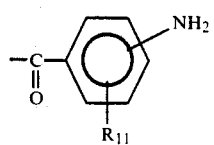

or by reacting a compound of formula V where $R_{61a}$ is

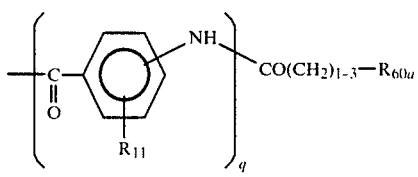

with a compound of formula VI or VII

 (VI)

 (VII)

Compounds of formula V can be prepared by known methods, for example where $R_{61a}$ is

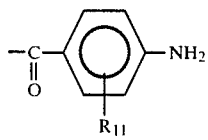

the compound of formula IV can be prepared by reacting a compound of formula VIII

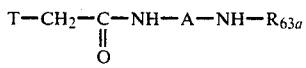 (VIII)

where $R_{63a}$ is

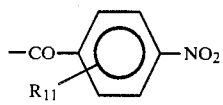

with a compound of formula IX

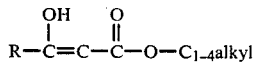 (IX)

to form a compound of formula X

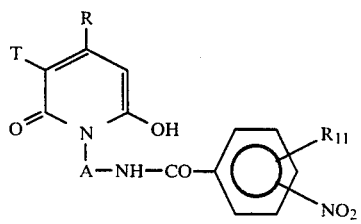 (X)

followed by reduction of the nitro group to an amino group or where $R_{61a}$ is hydrogen by saponification of the compound of formula X.

Compounds of formula I where $R_1$ is

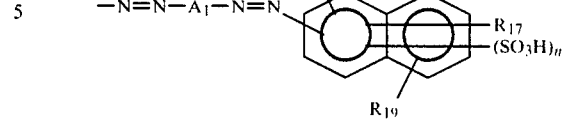

can be prepared by coupling to a diazotised compound of formula XI

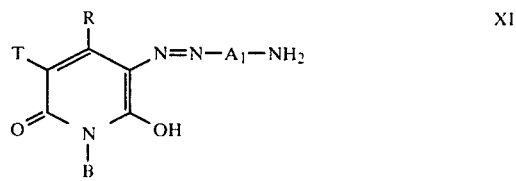 XI a compound of formula XIII

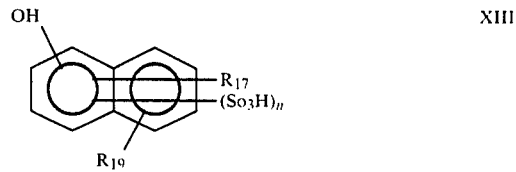 XIII by known methods.

Compounds of formula I where $R_1$ is other than hydrogen can be prepared by reacting a diazotised compound of formula XIa or XIIa

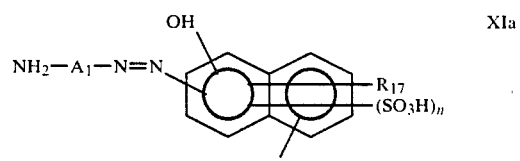 XIa

 XIIa with a compound of formula XIIIa

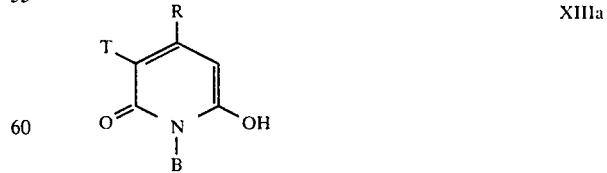 XIIIa according to known methods.

Compounds of formula XIV in metal-free form may be prepared by either reacting a diazotised compound of formula XV

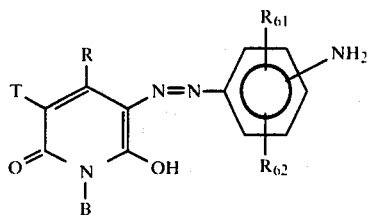

with a compound of the formula XVI

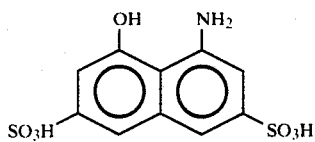

in acid medium to form a compound of formula XVII

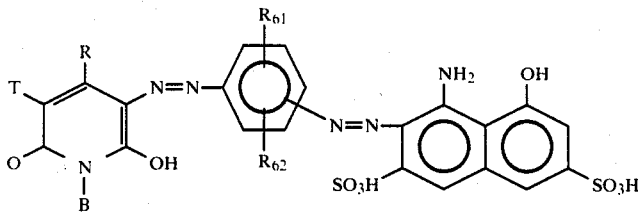

followed by reacting the compound of formula XVII with a diazotised compound of formula XVIII

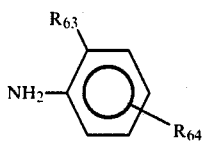

in alkali medium; or by reacting a diazotised compound of formula XVIII with the compound of formula XVI to form a compound of formula XIX

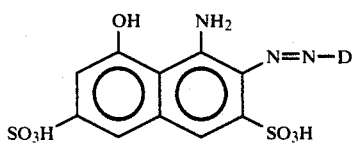

in acid medium followed by reacting the compound of formula XIX with a diazotised compound of formula XV in alkali medium. The $SO_3H$ groups can be converted to the salt form by known methods Coupling to form compounds of formula I where $R_1$ is other than hydrogen can be carried out according to known methods. Advantageously, coupling is carried out in aqueous (acid, neutral or alkali) medium at a temperature from $-10°$ C. to room temperature, if necessary in the presence of a coupling accelerator such as pyridine or urea. Alternatively, coupling may be effected in a mixture of solvents, for example, water and an organic solvent.

Metallisation of the compounds of formula I when $R_1$ is other than hydrogen can be achieved by known methods.

The azo compounds of formula I in 1:1 metal complex form may be prepared by metallising compounds of formula I in metal-free form with a metal selected from copper, cobalt, iron, nickel, manganese, chromium and zinc.

The azo compounds of formula I in 1:2 metal complex form may be prepared by metallising compounds of formula I in metal-free form with a metal selected from chromium, nickel, cobalt and iron.

A further method for the preparation of an azo compound of formula I in 1:2 metal complex form is by reacting an azo compound of formula I in metal-free form with an azo compound 1:1 metal complex when the metal is chromium, nickel, cobalt or iron.

The metallisation process to form a 1:1 metal complex is advantageously carried out by treating 1 mole of azo compound with a metallising agent containing 1 equivalent of metal.

Metallisation is carried out advantageously in aqueous medium or a mixture of water and a water-miscible organic solvent, for example acetone, lower alkyl alcohols, dimethylformamide, formamide, glycols or acetic acid at a pH range from 1.0 to 8.0, preferably pH 2 to 7. The metallisation process may be carried out at a temperature from room temperature to the boiling point of the reaction medium.

Alternatively, metallisation may be effected in a wholly organic medium (for example dimethylformamide). Advantageously, for instance, cobaltisation may be carried out in the presence of an inorganic nitrite such as lithium, sodium, ammonium or potassium nitrite in the ratio of 2 to 6 moles of nitrite per gram atom of cobalt.

Suitable cobalt-yielding compounds are, for example, cobalt (II) and Co (III) sulphate, acetate, formate and chloride.

Copper-yielding compounds are, for example cupric sulphate, cupric formate, cupric acetate and cupric chloride.

The nickel-yielding compounds are Ni (II) and Ni (III) compounds, such as nickel formate, nickel acetate and nickel sulphate.

Preferred manganese-yielding compounds are Mn (II) compounds and iron-yielding compounds are Fe (II) and Fe (III) compounds. Examples of these and zinc-yielding compounds are manganese, iron and zinc formate, acetate and sulphate.

Preferred chromium-yielding compounds are Cr (II) and Cr (III) formate, acetate and sulphate.

In the compounds of formula I the anions $A^\ominus$ can be any non-chromophoric anions such as those conventional in basic dyestuff chemistry. Suitable anions include chloride, bromide, sulphate, bisulphate, methylsulphate, aminosulphonate, perchlorate, benzenesulphonate, oxalate, maleate, acetate, propionate, lactate, succinate, tartrate, malate, methanesulphonate and benzoate, as well as complex anions, for example, zinc chloride double salts and anions of boric acid, citric acid, glycollic acid, diglycollic acid and adipic acid or addition products of orthoboric acid with polyalcohols with at least one cis diol group present. These anions can be exchanged for each other by ion exchange resins or by reaction with acids or salts, for example via the hydroxide or bicarbonate or according to German Offenlegungsschrift No. 2,001,748 or 2,001,816.

The azo compounds of formula I are suitably worked up into solid or liquid preparations, for example by granulation or by dissolving in a suitable solvent. The compounds of formula I are suitable for dyeing, padding or printing on fibres, threads or textile materials particularly natural or regenerated cellulose materials for example cotton, or synthetic polyamides or synthetic polyesters in which the acid groups have been modified. Such a polyamide is described in Belgian Pat. No. 706,104 and such a synthetic polyester is described in U.S. Pat. No. 3,379,723.

The azo compounds of formula I may also be applied to bast fibres such as hemp, flax, sisal, jute, coir or straw.

The azo compounds of formula I are also used for dyeing, padding or printing fibres, threads or textiles produced therefrom which consist of or contain homo- or mixed polymers of acrylonitrile or of 1,1-dicyanoethylene.

The textile material is dyed, printed or pad-dyed in accordance with known methods. Acid modified-polyamide is dyed particularly advantageously in an aqueous, neutral or acid medium, at temperatures of 60° C. to boiling point or at temperatures above 100° C. under pressure.

The textile material may also be dyed by the compounds of formula I in organic solvents, e.g. in accordance with the directions given in German Offenlegungschrift No. 2,437,549.

Cellulose material is mainly dyed by the exhaust process i.e. from a long or short bath, at room temperature to boiling temperature, optionally under pressure, whereby the ratio of the bath is from 1:1 to 1:100 and preferably from 1:20 to 1:50. If dyeing is effected from a short bath, then the liquor ratio is 1:5 to 1:15. The pH of the dyebath varies between 3 and 10 (for short and long dyebaths). Dyeing preferably takes place in the presence of electrolytes.

Printing may be effected by impregnation with a printing paste produced by known methods.

The dyes of formula I are also suitable for dyeing or printing paper, e.g. for the production of bulk-dyed, sized and unsized paper. The dyestuffs may similarly be used for dyeing paper by the dipping process. The dyeing of paper is effected by known methods.

The dyes of formula I are also suitable for dyeing or printing leather by known methods.

Dyeings with good fastness are obtained on both paper and leather.

Dyeings made with the dyes of formula I on leather have good light fastness properties, good diffusion properties with PVC, good water-, wash and sweat-fastness properties, good fastness to dry cleaning, good fastness to drops of water and good fastness to hard water.

Dyeings prepared with dyes of formula I (where $R_1$ is other than hydrogen) on paper produce a substantially clear spent liquor which is important for environmental reasons. The dyes of formula I have good build-up properties, do not run once applied to paper and are not pH sensitive. Dyeings produced with dyes of formula I have good light fastness and the nuance on exposure for a long time to light fades tone in tone. The dyes of formula I have good wet-fastness properties not only for water but also for milk, soap, water, sodium chloride solution, fruit juice, and sweetened mineral water. Further dyeings made with dyes of formula I are fast for alcoholic beverages due to a good alcohol fastness. Further the dyes of formula I have good nuance stability.

The dyes of formula I may be converted into dyeing preparations. Processing into stable liquid or solid dyeing preparations may take place in a generally known manner, advantageously by grinding or granulating or by dissolving in suitable solvents, optionally adding an assistant, e.g. a stabiliser or dissolving intermediary such as urea. Such preparations may be obtained, for example, as described in French Patent Specification Nos. 1,572,030 and 1,581,900 or in accordance with German DOS Nos. 2,001,748 and 2,001,816.

Liquid preparations of the compounds of formula I preferably comprise 10 to 30% by weight of a compound of formula I and to 30% of a solubilising agent such as urea, lactic acid or acetic acid, the rest of the composition being water. Solid preparations preferably comprise 20 to 80% dyestuff, 20 to 80% solubilising agent such as urea or $Na_2SO_4$ and 2 to 5% water.

In the following Examples all parts and percentages given are by weight and the temperatures given are in degree Centigrade, unless indicated to the contrary.

EXAMPLE 1

390 Parts (2 moles) of para-nitrobenzoic acid ethyl ester are warmed in 3200 parts of ethanol and 360 parts (6 moles) of ethylene diamine at 60°–65°. After stirring for several hours a fine crystalline product results which after filtration produces 360 parts of a compound of formula (1a)

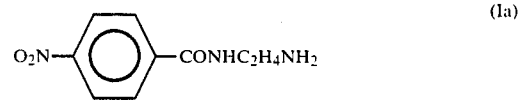

having a melting point (of the unpurified product) of 132°–134°.

A compound of formula (1b)

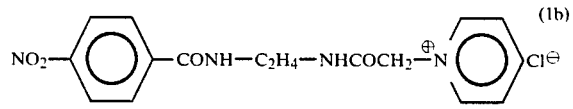

is formed by reacting the compound of formula (1a) with the product of slight excess pyridine and 1 mole of chloroacetic acid methyl ester, in ethanol at 55° C.

Without isolating the compound (1b) 1 mole of acetoacetic acid methyl ester is added to the reaction mixture and this is treated at 25° C. in the presence of base by known methods to produce a compound of formula (1c)

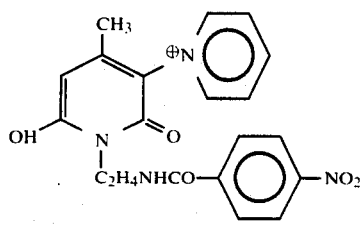
(1c)

which can be reduced by the Béchamps method to the corresponding amine.

After adding water to the reaction mixture, the compound of formula (1c) precipitates out.

The compound of formula (1c) is saponified in 5–7% hydrochloric acid according to known methods to form an amine of formula (1d)

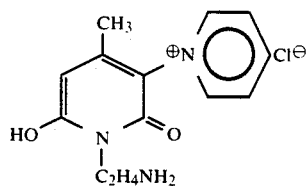
(1d)

The compound of formula (1d) is reacted according to known methods in water at about 90° and a pH of 9 with a compound of formula (1e)

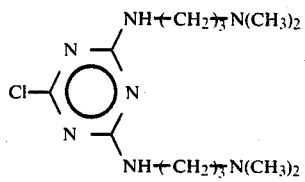
(1e)

to form a compound of formula (1f)

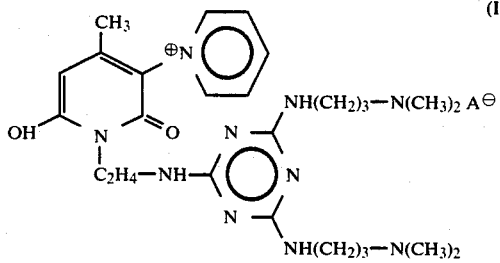
(1f)

The compound of formula (1f) is very water soluble, particularly in acid medium and can be used as a coupling component in the preparation of azo dyestuffs.

EXAMPLE 2

In a similar manner to the method of Example 1, a compound of the formula

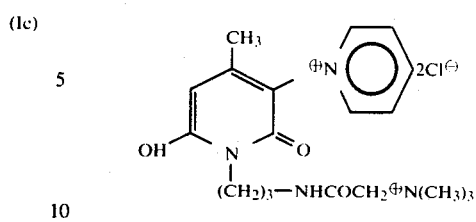

is formed using 1,3-diaminopropane instead of ethylene diamine and chloroacetyl chloride and trimethylamine instead of the compound of formula (1e).

EXAMPLE 3

225 Parts (1.5 moles) of m-aminoacetanilide in the form of the acid addition salt are placed in a mixture of equivoluminar glacial acetic acid and water together with sodium acetate. On cooling to 0°–5° C., 254 parts of chloroacetyl chloride (2.25 moles) are added over 2 hours. A product of formula 3a

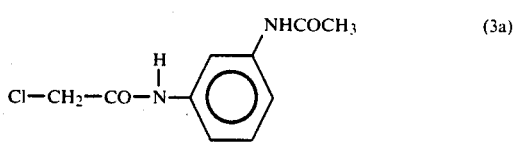
(3a)

is formed. 1 mole of the compound of formula 3a is reacted according to known methods with 1 mole of pyridine to form a compound of formula 3b

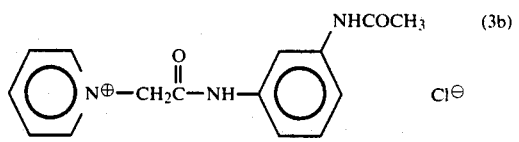
(3b)

Without the need to isolate the compound of formula 3b 1 mole of acetoacetic acid methyl ester is added to the reaction mixture and according to known methods at room temperature in the presence of base a compound of formula 3c

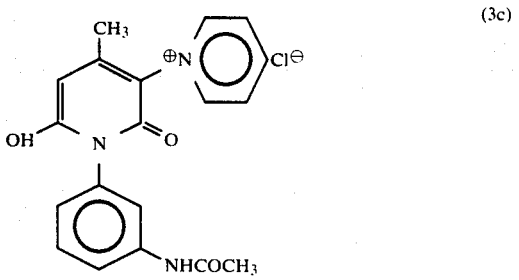
(3c)

is formed.

At 95°–98° C. the compound of formula 3c is saponified with about 5% hydrochloric acid to form a compound of formula 3d

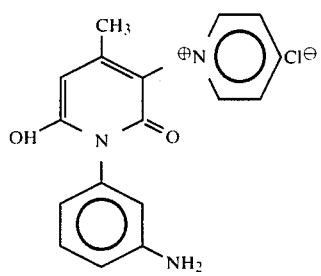

The compound of formula 3d is converted into that of formula 3e

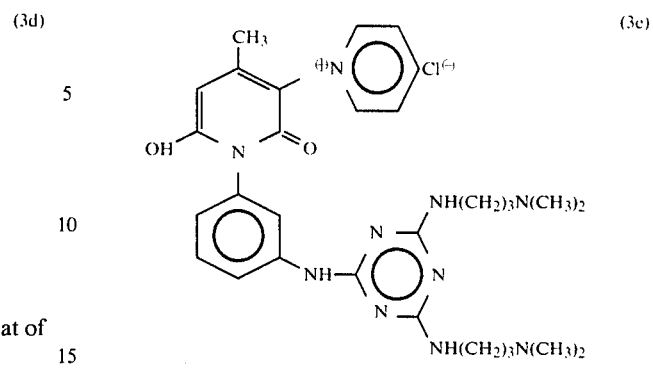

in a similar way to that described in Example 1.

EXAMPLES 4 TO 12

Compounds of the formula

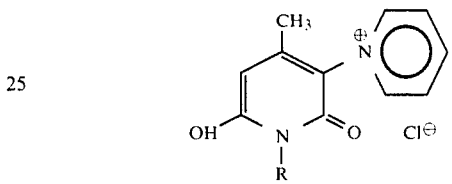

where R is defined in Table 1 below, may be prepared by a method analogous to that of Example 1.

TABLE 1

| Example No. | R |
|---|---|
| 4 | —(CH$_2$)$_2$—NHCO—C$_6$H$_4$—NH—[triazine with NH(CH$_2$)$_3$N(CH$_3$)$_2$ and NH(CH$_2$)$_3$N(CH$_3$)$_2$] |
| 5 | —(CH$_2$)$_2$—NHCO—C$_6$H$_4$—NH—[triazine with NH(CH$_2$)$_3$N$^{\oplus}$(CH$_3$)$_3$ and NH(CH$_2$)$_3$N$^{\oplus}$(CH$_3$)$_3$]  2Cl$^{\ominus}$ |
| 6 | —(CH$_2$)$_2$—NH—[triazine with NH(CH$_2$)$_3$N$^{\oplus}$(CH$_3$)$_3$ and NH(CH$_2$)$_3$N$^{\oplus}$(CH$_3$)$_3$]  2Cl$^{\ominus}$ |
| 7 | 3-(NHCOCH$_2$Cl)—C$_6$H$_4$— |

TABLE 1-continued
| Example No. | R |
|---|---|
| 8 |  |
| 9 | 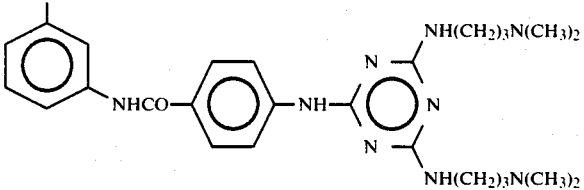 |
| 10 | 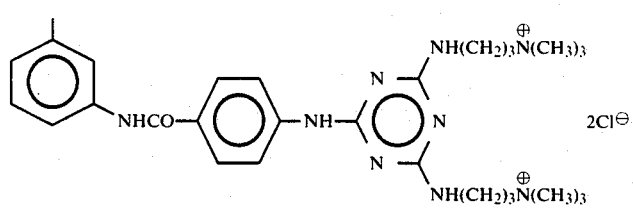 |
| 11 | 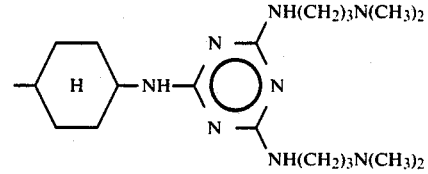 |
| 12 | 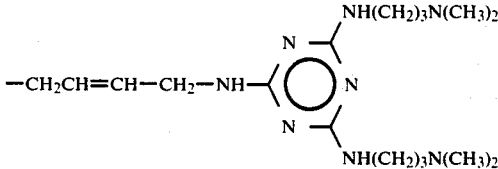 |
EXAMPLES 13 TO 44
In the following Examples compounds of the formula
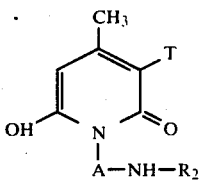
where T, A and $R_2$ are given in Table 2 below, may be prepared by a method analogous to Example 1. In Table 2, $T_2$ to $T_7$ and $A_2$ to $A_{32}$ are as given below and $A^\ominus$ is $CH_3COO^\ominus$;
$T_2$ represents —CN
$T_3$ represents —CONH$_2$
$T_4$ represents 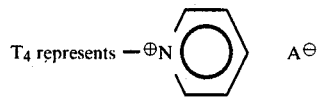
$T_5$ represents 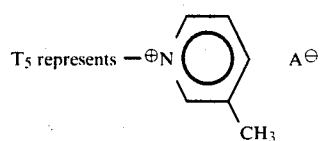

-continued
$T_6$ represents 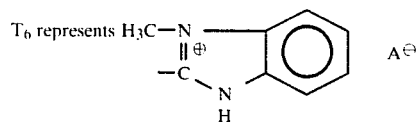 $A^{\ominus}$
$T_7$ represents 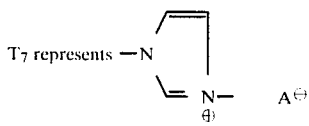 $A^{\ominus}$
$A_2$ represents 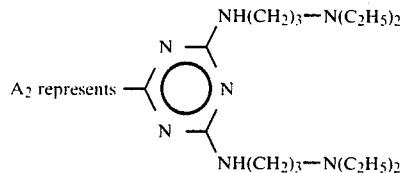
$A_3$ represents 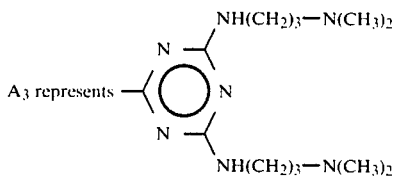
$A_4$ represents $-COCH_2-\overset{\oplus}{N}(CH_3)_3$  $A^{\ominus}$
$A_5$ represents 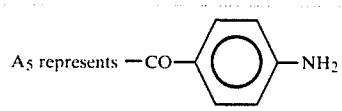
$A_6$ represents 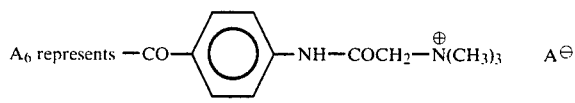 $A^{\ominus}$
$A_7$ represents 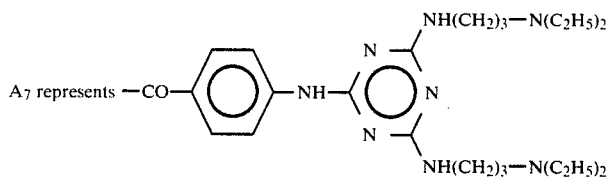
$A_8$ represents 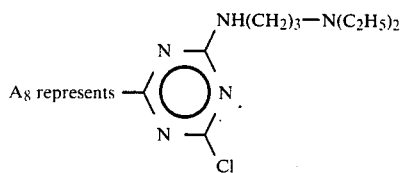
$A_9$ represents 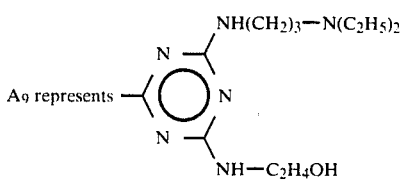
$A_{10}$ represents 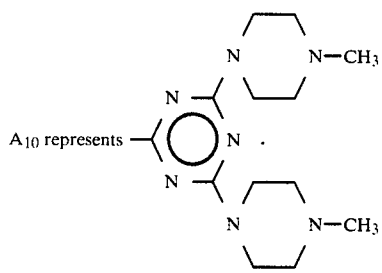
$A_{11}$ represents 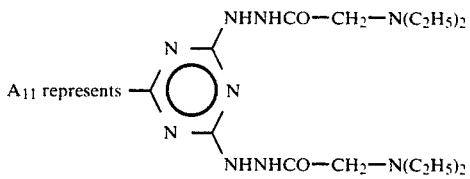
$A_{12}$ represents 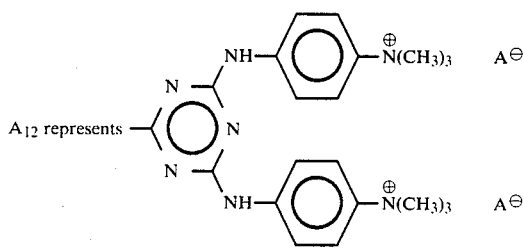 $A^{\ominus}$ $A^{\ominus}$ -continued
$A_{13}$ represents 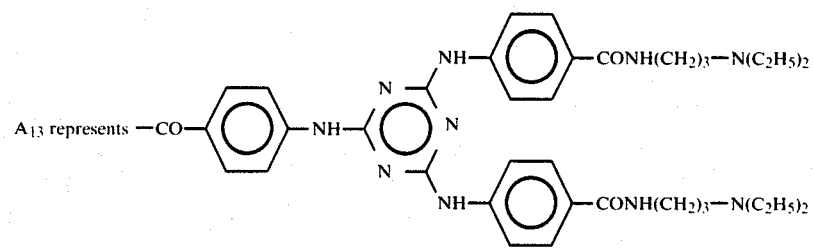
$A_{14}$ represents 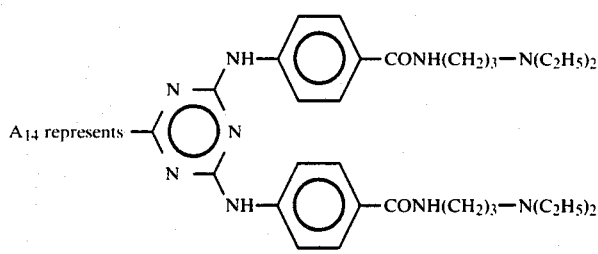
$A_{15}$ represents 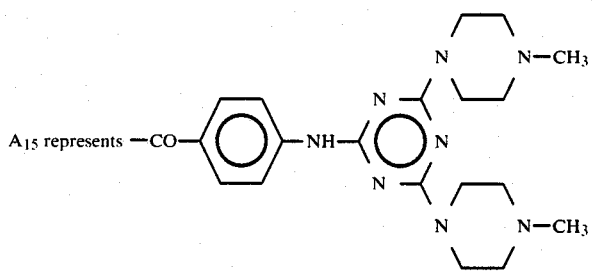
$A_{16}$ represents 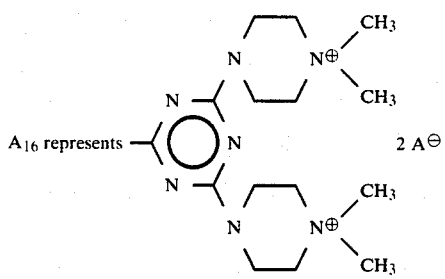   $2 A^\ominus$
$A_{17}$ represents 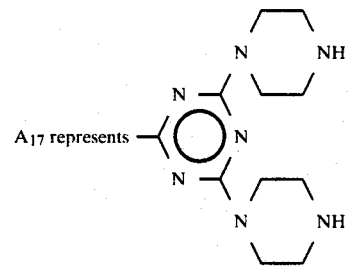
$A_{18}$ represents 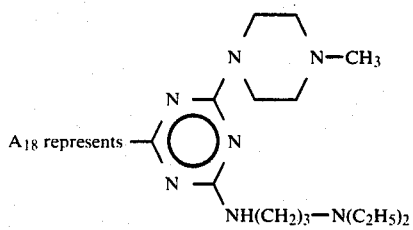
$A_{19}$ represents 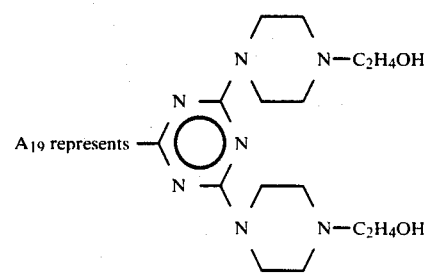

$A_{20}$ represents 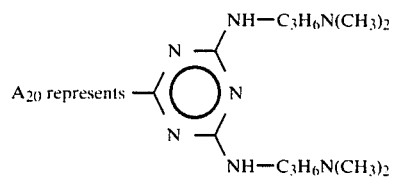
$A_{21}$ represents 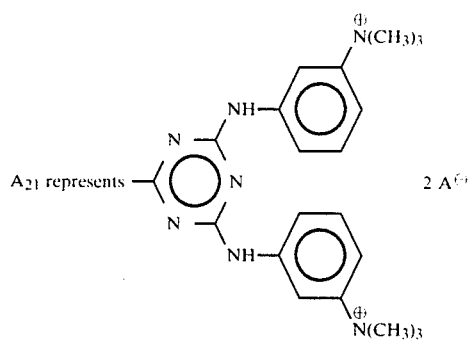 $2\ A^{\ominus}$
$A_{22}$ represents 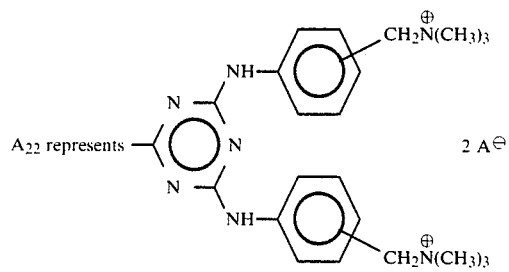 $2\ A^{\ominus}$
$A_{23}$ represents 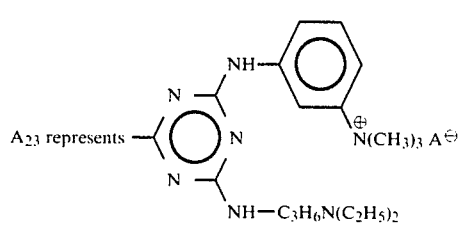
$A_{24}$ represents 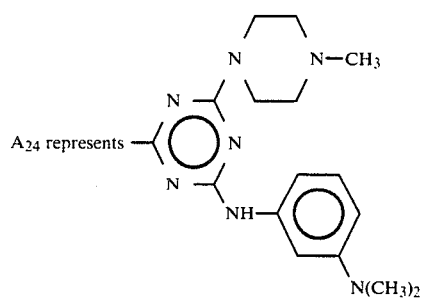
$A_{25}$ represents 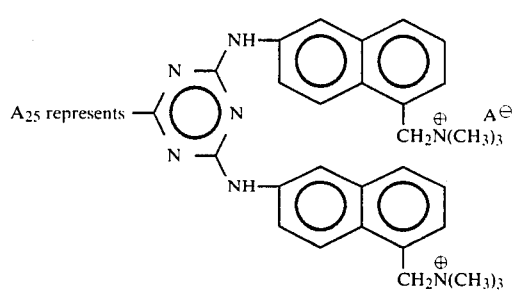
$A_{26}$ represents 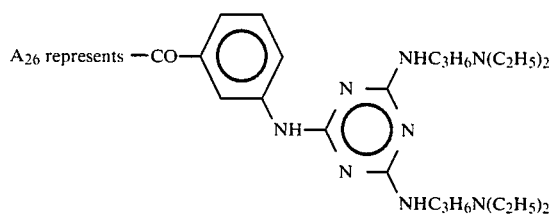
$A_{27}$ represents 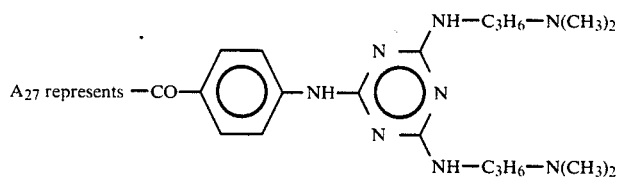
$A_{28}$ represents 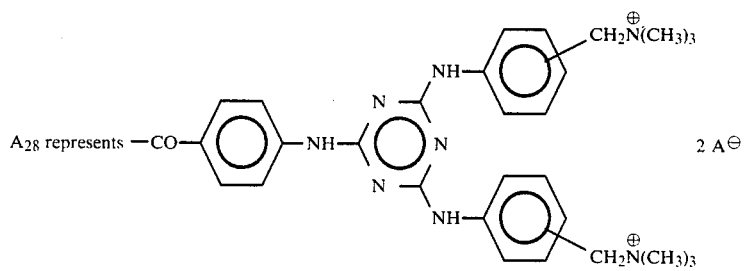 $2\ A^{\ominus}$ $A_{29}$ represents — 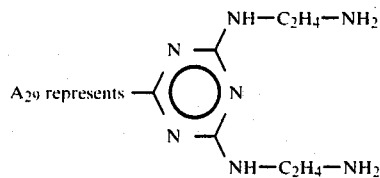

$A_{30}$ represents — 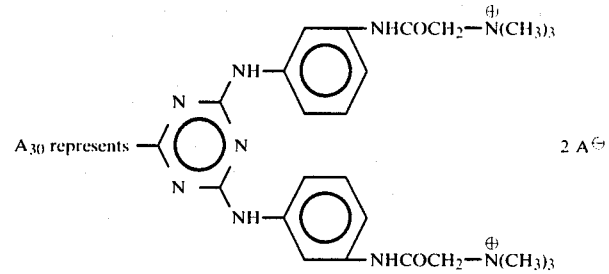 2 A⊖

$A_{31}$ represents — 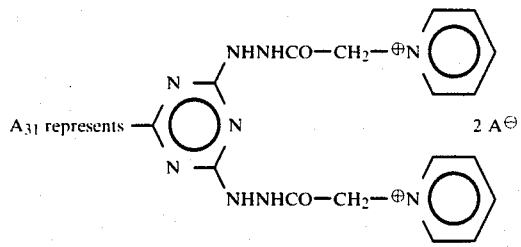 2 A⊖

$A_{32}$ represents — 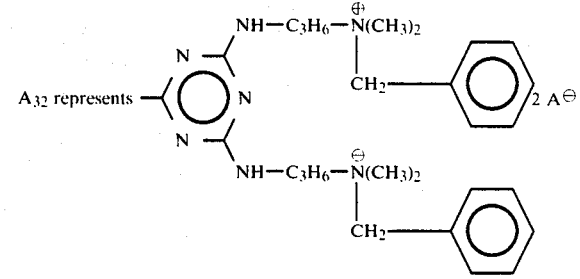 2 A⊖

TABLE 2

| Example No. | T | A | $R_2$ |
|---|---|---|---|
| 13 | H | $-C_2H_4-$ | H |
| 14 | $T_2$ | " | $A_2$ |
| 15 | $T_3$ | " | $A_3$ |
| 16 | $T_4$ | " | $A_4$ |
| 17 | $T_6$ | " | $A_5$ |
| 18 | $T_7$ | " | $A_6$ |
| 19 | $T_4$ | 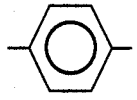 | $A_7$ |
| 20 | " | " | $A_8$ |
| 21 | $T_5$ | " | $A_9$ |
| 22 | $T_4$ | 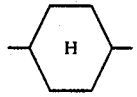 | $A_{10}$ |
| 23 | " | $-CH_2-CH=CH-CH_2-$ | $A_{11}$ |
| 24 | $T_2$ | " | $A_{12}$ |
| 25 | $T_4$ | $-C_2H_4-$ | $A_{13}$ |
| 26 | " | " | $A_{14}$ |
| 27 | " | " | $A_{15}$ |
| 28 | " | " | $A_{16}$ |
| 29 | " | " | $A_{17}$ |
| 30 | " | " | $A_{18}$ |
| 31 | " | " | $A_{19}$ |
| 32 | " | " | $A_{20}$ |
| 33 | " | " | $A_{21}$ |
| 34 | " | " | $A_{22}$ |
| 35 | " | " | $A_{23}$ |
| 36 | " | " | $A_{24}$ |
| 37 | " | " | $A_{25}$ |
| 38 | " | " | $A_{26}$ |
| 39 | " | " | $A_{27}$ |
| 40 | " | " | $A_{28}$ |
| 41 | " | " | $A_{29}$ |
| 42 | " | " | $A_{30}$ |
| 43 | " | " | $A_{31}$ |
| 44 | " | " | $A_{32}$ |

EXAMPLE 45

A compound of the formula 45a is prepared by diazotising 1 mole of 4-aminoacetanilide and coupling with 1 mole of the compound 1f of Example 1.

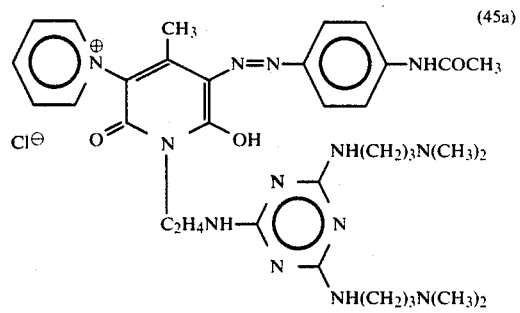
(45a)

By the additions of 30% hydrochloric acid to the aqueous solution of compound 45a, a 7% hydrochloric acid containing solution is produced and this is refluxed for 10 hours. A compound of the formula 45b results

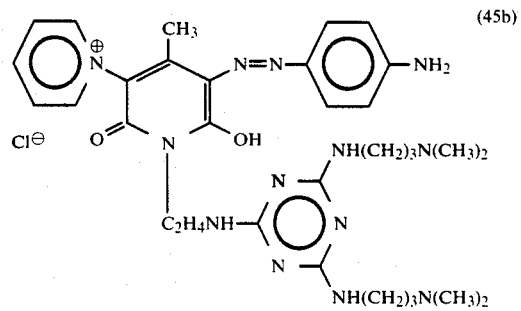
(45b)

1 mole of the compound 45b is then diazotised and then is coupled to 1 mole of a compound of the formula 45c

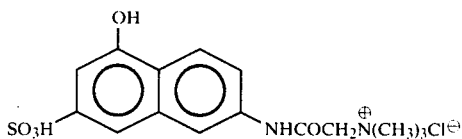

to form a compound of formula 45d

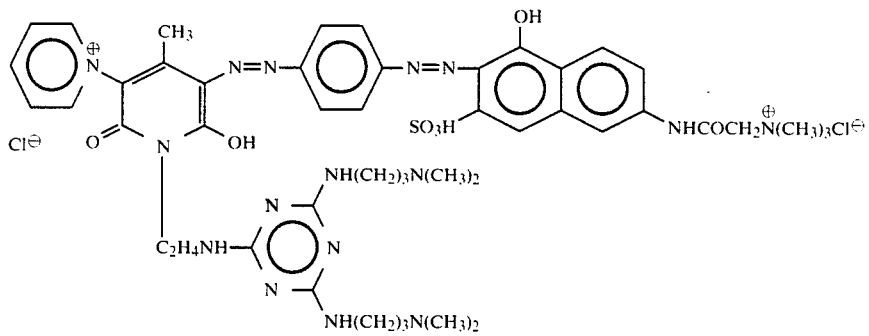

and this compound dyes paper a blue violet tone.

A similar product can be obtained by using 1 mole of a compound of formula 45e

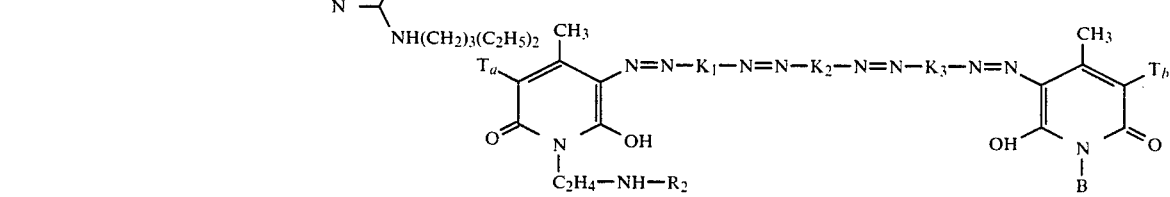

instead of the compound of formula 45c

EXAMPLE 46

6.9 Parts of 1-amino-4-nitrobenzene (1/20 mole) is diazotised in hydrochloric acid solution at −0° to 5° C. with 3.5 parts (1/20 mole) sodium nitrite. Then 1/40 mole of the diazonium solution is coupled to 8 parts of 1-amino-8-hydroxynaphthalene-3,6-disulphonic acid (1/40 mole) pH at 1. The remaining 1/40 mole diazonium solution is coupled at pH 9 to the monoazo dyestuff so formed to form a compound of formula 46a

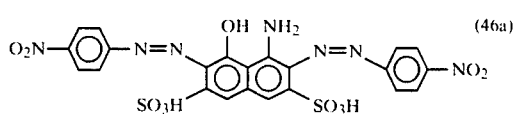

The nitro groups of the compound 45a are reduced according to known methods, then both —$NH_2$ groups so formed are diazotised and then 1 mole of the diazotised compound is coupled to 2 moles the compound Ie of Example 1 to form a compound of formula 46b.

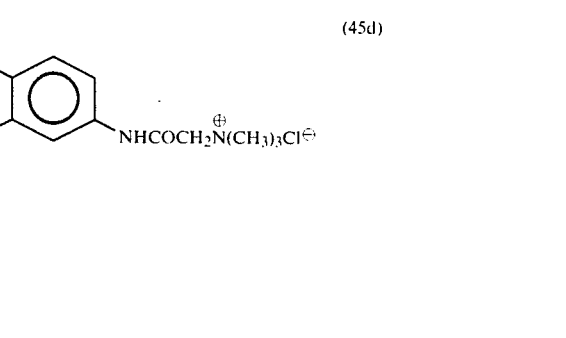

The compound 46b dyes paper a black tone.

EXAMPLES 47 TO 64

Compounds of the formula in which the symbols are defined in Table 3 below (where symbols $T_{4-7}$ and $A_{2-4}$ are defined under Examples 13 to 44 and the symbols $B_2-B_{11}$ are defined below) can be made in an analogous manner to the method of Example 46.

$B_2$ represents —$C_2H_5$
$B_3$ represents —$C_2H_4OH$
$B_4$ represents —$(CH_2)_3N(CH_3)_2$ -continued B$_5$ represents —(CH$_2$)$_3\overset{\oplus}{\text{N}}$(CH$_3$)$_3$CH$_3$SO$_4^\ominus$ B$_6$ represents —(CH$_2$)$_2$—NH$_2$ B$_7$ represents —(CH$_2$)$_3$—NH$_2$ B$_8$ represents —(CH$_2$)$_2$—NH— (triazine with NH(CH$_2$)$_3$—N(C$_2$H$_5$)$_2$ substituents)

B$_9$ represents —(CH$_2$)$_2$—NHCOCH$_2$—$\overset{\oplus}{\text{N}}$(CH$_3$)$_3$Cl$^\ominus$ -continued B$_{10}$ represents 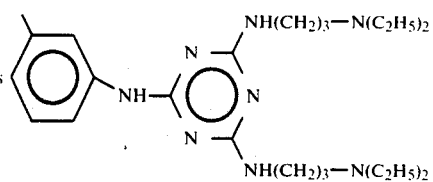

B$_{11}$ represents —C$_2$H$_4$NHCO—(phenyl)—NH—(triazine with NH(CH$_2$)$_3$—N(C$_2$H$_5$)$_2$ substituents)

TABLE 3

| EX. No. | T$_a$ | R$_2$ | T$_b$ | B | K$_1$ | K$_3$ | K$_2$ |
|---|---|---|---|---|---|---|---|
| 47 | T$_5$ | A$_2$ | T$_5$ | B$_8$ | phenyl | phenyl | 4-amino-5-hydroxy-naphthalene-2,7-disulfonic acid (NH$_2$, OH, SO$_3$H, SO$_3$H) |
| 48 | T$_4$ | A$_2$ | T$_4$ | B$_4$ | " | " | " |
| 49 | T$_4$ | H | T$_5$ | B$_4$ | " | HO-phenyl | " |
| 50 | T$_4$ | A$_2$ | T$_5$ | B$_4$ | methylphenyl | phenyl | " |
| 51 | T$_5$ | A$_2$ | T$_5$ | B$_8$ | phenyl | methylphenyl | " |
| 52 | T$_4$ | A$_2$ | T$_4$ | B$_4$ | " | OH-phenyl | " |
| 53 | T$_5$ | A$_2$ | T$_5$ | B$_8$ | " | " | " |
| 54 | T$_5$ | A$_2$ | T$_6$ | B$_8$ | " | phenyl | 4-amino-5-hydroxy-naphthalene-2,7-disulfonic acid isomer (NH$_2$, OH, HO$_3$S, SO$_3$H) |
| 55 | T$_4$ | A$_2$ | T$_4$ | B$_4$ | " | " | " |
| 56 | T$_7$ | A$_4$ | T$_5$ | B$_8$ | " | methylphenyl | " |

TABLE 3-continued

| EX. No. | $T_a$ | $R_2$ | $T_b$ | B | $K_1$ | $K_3$ | $K_2$ |
|---|---|---|---|---|---|---|---|
| 57 | $T_4$ | $A_2$ | $T_4$ | $B_4$ | 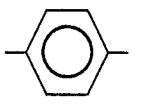 | 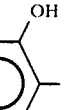 | |
| 58 | $T_4$ | $A_2$ | $T_4$ | $B_8$ | " | " | " |
| 59 | $T_4$ | $A_2$ | $T_4$ | $B_4$ | 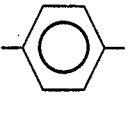 | 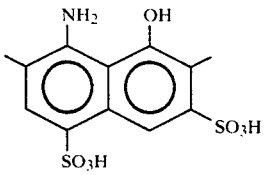 | |
| 60 | $T_5$ | $A_2$ | $T_5$ | $B_8$ | " | " | " |
| 61 | $T_4$ | $A_2$ | $T_7$ | $B_2$ | " | 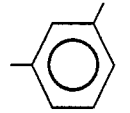 | " |
| 62 | $T_5$ | $A_2$ | $T_4$ | H | " | " | " |
| 63 | $T_4$ | $A_2$ | $T_4$ | $B_4$ | " | 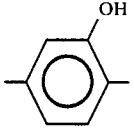 | " |
| 64 | $T_5$ | $A_2$ | $T_5$ | $B_8$ | " | " | " |

The compounds of Examples 47 to 64 dye paper a black tone.

EXAMPLE 65

1/20 mol of para nitroaniline is diazotised and coupled to 1/20 mol of 1-amino-8-hydroxynaphthalene-3,6-disulphonic acid. To the resulting monoazo dyestuff, 1/20 mol of diazotised 1-amino-2-hydroxy-4-nitrobenzene is coupled to give a compound of formula 65a

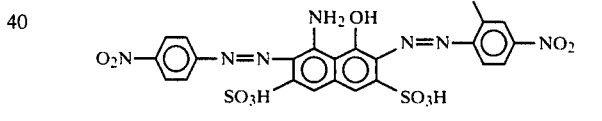

(65a)

The nitro groups of the compound 65a are reduced with sodium sulphide at pH 11-12. The diamino diazo compound so formed is tetrazotised as in Example 46 and coupled to 1/10 mol of the compound of Ie of Example 1 to form a compound of formula 65b

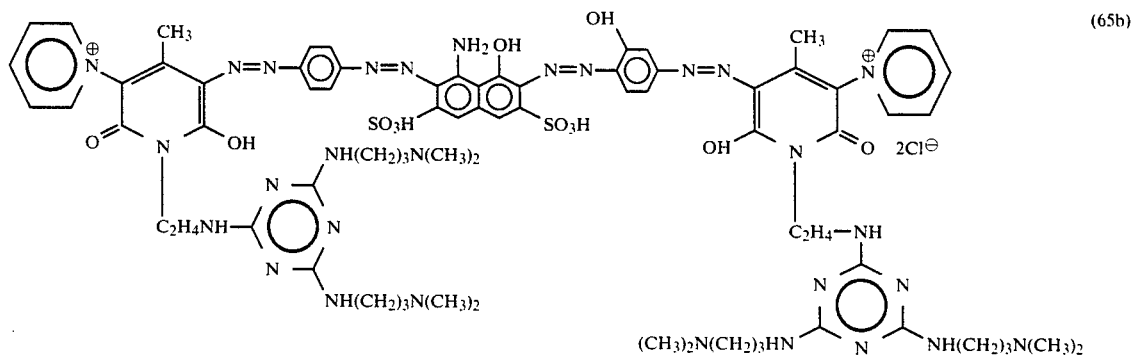

(65b)

This dyestuff dyes paper a black shade.
This compound may also be metallised with copper, iron, chromium or cobalt to form a 1:1 metal complex or with chromium, cobalt or iron to form a 1:2 metal complex according to known methods.

EXAMPLES 66 TO 68

The following compounds can be made by a method analogous to that of Example 65 (or by other known methods) from the corresponding starting compounds.

EXAMPLE 66

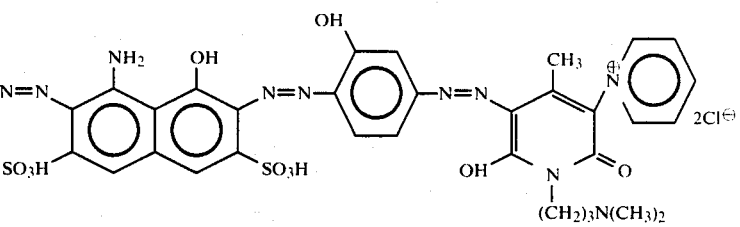

EXAMPLES 67 AND 68

In these Examples the group $R_a$ is of the formula

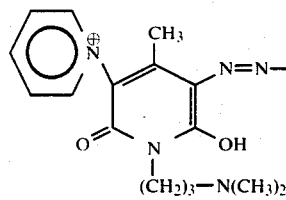

A compound of the formula

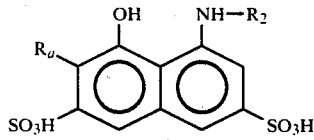   (Example 67)

where $R_2$ is $A_2$ (defined under Examples 13 to 44) may be prepared by an analogous method to that of Example 46 or by any other known method.

A compound of the formula

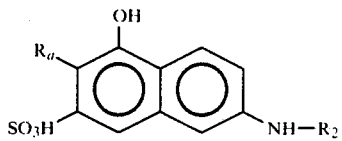   (Example 68)

where $R_2$ is $A_2$ (defined under Examples 13 to 44) may be prepared by an analogous method to that of Example 46 (or by any other known method).

In Examples 67 and 68 $R_2$ may be replaced by hydrogen or any of the groups $A_3$ to $A_{32}$ defined under Examples 13 to 46.

These dyestuffs dye paper a blue tone.

EXAMPLES 69 AND 70

In these Examples $R_b$ is a group of the formula

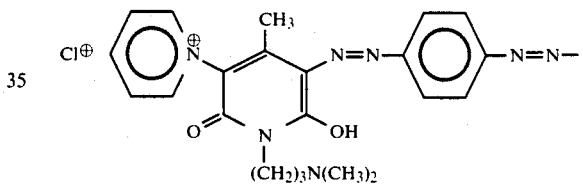

A compound of the formula of Example 67 in which $R_a$ is replaced by $R_b$ (Example 69) can be prepared by an analogous method to that of Example 67.

A compound of the formula of Example 68 in which $R_a$ is replaced by $R_b$ (Example 70) may be prepared by an analogous method to that of Example 68.

In Examples 69 and 70, $R_2$ may be replaced by hydrogen or any other group $A_3$–$A_{32}$ defined under Examples 13 to 44. The dyeings produced from compounds of Examples 69 and 70 are of a blue tone.

EXAMPLE 71

From the corresponding starting compounds, a compound of the formula 71a

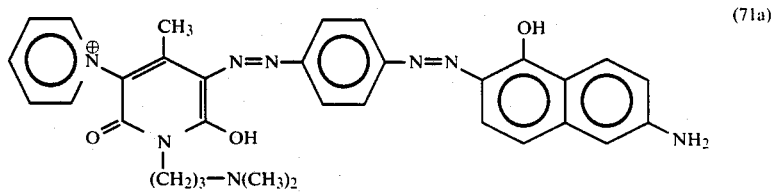   (71a)

can be prepared by a method analogous to that of Example 45 and from corresponding starting products a compound of formula 71b

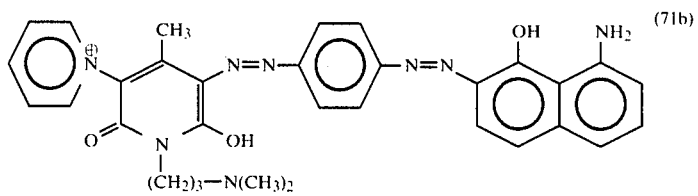

can be prepared by a method analogous to that of Example 45. The compounds of formula 71a and 71b dye paper a blue tone.

EXAMPLES 73 TO 106

By an analogous method to that of Example 65 (or by any other known method) compounds of the formula

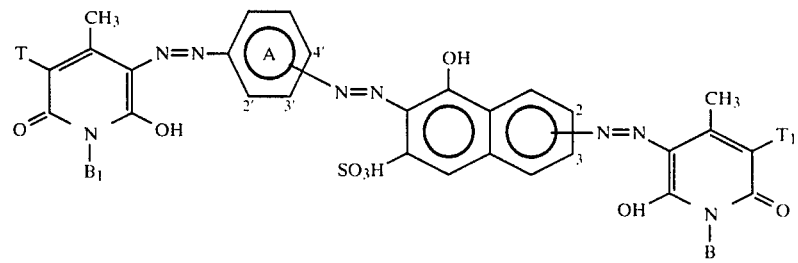

EXAMPLE 72

From suitable starting compounds a compound of formula 72a are produced in which the symbols are defined in the Table 4 below and $T_{2-4}$ are defined under Examples 13 to 44 and $B_{4-8}$ are defined under Examples 47 to 64 and

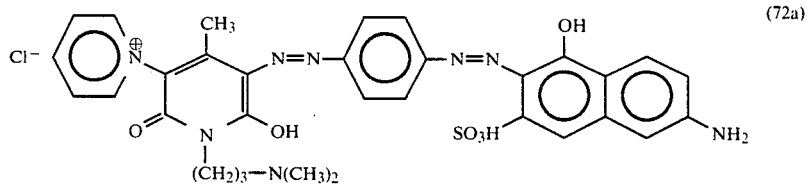

$B_{12}$ is be prepared by a method analogous to that of Example 45.

A compound of formula 72b

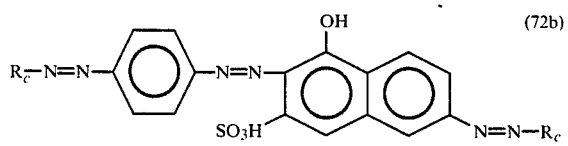

where $R_c$ is

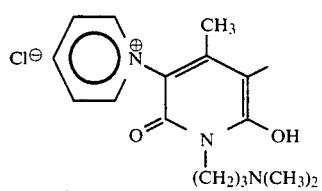

may be formed by diazotising the compound of formula 72a and coupling with a compound of the formula H—$R_c$ The compound of formula 72a is violet in colour and the compound of formula 72b dyes paper a black tone.

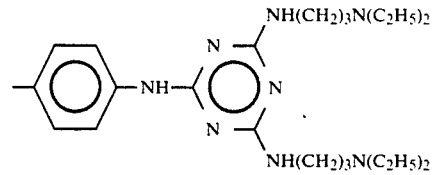

TABLE 4

| EX. No. | T | $T_1$ | position of floating group in ring A | position of floating gp. in naphthalene ring | $B_1$ | B |
|---|---|---|---|---|---|---|
| 73 | $T_4$ | $T_4$ | 4' | 3 | —$(CH_2)_3$—$N(CH_3)_2$ | $B_4$ |
| 74 | $T_4$ | $T_4$ | 3' | 2 | " | $B_4$ |
| 75 | $T_4$ | $T_4$ | 3' | 3 | " | $B_4$ |
| 76 | $T_4$ | $T_4$ | 4' | 3 | " | H |
| 77 | $T_4$ | $T_2$ | 4' | 3 | " | $B_4$ |
| 78 | $T_4$ | $T_2$ | 4' | 2 | " | $B_4$ |
| 79 | $T_4$ | $T_2$ | 4' | 2 | " | $B_4$ |
| 80 | $T_4$ | $T_2$ | 3' | 2 | " | $B_4$ |
| 81 | $T_4$ | $T_4$ | 4' | 2 | $B_8$ | $B_8$ |
| 82 | $T_4$ | $T_4$ | 3' | 2 | $B_8$ | $B_8$ |
| 83 | $T_4$ | $T_4$ | 3' | 3 | $B_8$ | $B_8$ |
| 84 | $T_4$ | $T_4$ | 4' | 3 | $B_8$ | $B_8$ |
| 85 | $T_4$ | $T_4$ | 4' | 3 | $B_8$ | H |
| 86 | $T_4$ | $T_4$ | 4' | 2 | $B_8$ | H |
| 87 | $T_4$ | $T_4$ | 3' | 3 | $B_8$ | H |
| 88 | $T_4$ | $T_4$ | 3' | 2 | $B_8$ | H |

TABLE 4-continued

| EX. No. | T | T₁ | position of floating group in ring A | position of floating gp. in naphthalene ring | B₁ | B |
|---|---|---|---|---|---|---|
| 89 | T₄ | T₄ | 4' | 3 | B₈ | B₄ |
| 90 | T₄ | T₄ | 4' | 2 | B₈ | B₄ |
| 91 | T₄ | T₄ | 3' | 3 | B₈ | B₄ |
| 92 | T₄ | T₄ | 3' | 2 | B₈ | B₄ |
| 93 | T₄ | T₂ | 4' | 3 | B₈ | B₄ |
| 94 | T₄ | T₂ | 4' | 2 | B₈ | B₄ |
| 95 | T₄ | T₂ | 3' | 3 | B₈ | B₄ |
| 96 | T₄ | T₂ | 3' | 2 | B₈ | B₄ |
| 97 | T₂ | T₄ | 4' | 3 | B₄ | B₄ |
| 98 | T₂ | T₄ | 4' | 2 | B₄ | B₈ |
| 99 | T₄ | T₄ | 4' | 2 | B₄ | B₈ |
| 100 | T₄ | T₄ | 4' | 3 | H | B₈ |
| 101 | T₄ | T₄ | 4' | 2 | H | B₈ |
| 102 | T₄ | T₄ | 4' | 2 | B₁₂ | B₈ |
| 103 | T₄ | T₄ | 4' | 3 | " | H |
| 104 | T₄ | T₄ | 4' | 2 | " | B₄ |
| 105 | T₄ | T₄ | 4' | 3 | " | B₁₂ |
| 106 | T₄ | T₄ | 4' | 2 | B₈ | B₁₂ |

The compounds of Examples 73 to 106 may also contain OH groups in positions 2', 3' or 4'. In these cases these compounds can be metallised to form 1:1 metal complexes with copper, chromium, cobalt or iron or 1:2 metal complexes with chromium, cobalt or iron.

Compounds of Examples 73–106 may also contain $OCH_3$ groups in positions 2', 3' or 4'. In these cases these compounds may be metallised to form 1:1 metal complexes, preferably with copper.

The compounds so formed are of the formula

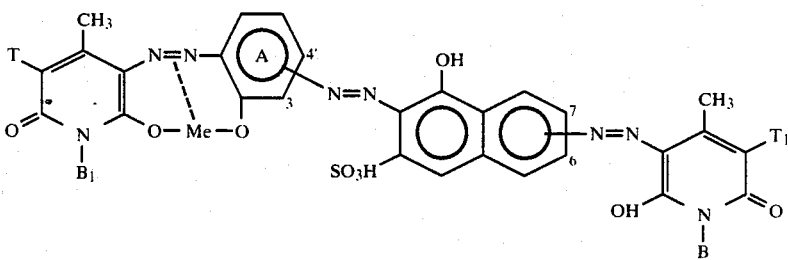

or of the formula

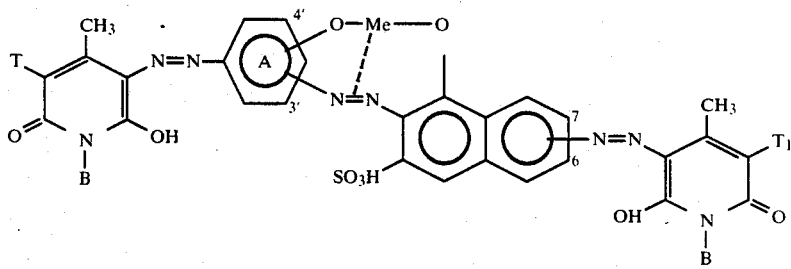

where Me is copper, chromium, cobalt or iron (to form 1:1 metal complexes) or chromium, cobalt or iron (to form 1:2 metal complexes).

EXAMPLE 107

12.3 Parts of ortho anisidine (0.1 mole) are diazotised and then coupled to a compound of formula (107a)

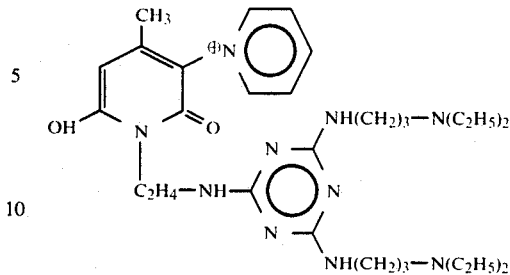

to form a compound of the formula 107b

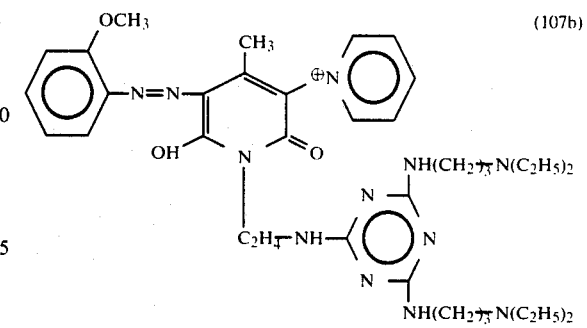

This dyestuff dyes paper a yellow shade. The dyestuff (107b) can be used for dyeing polyacrylonitrile in the mass.

EXAMPLES 108 TO 131

Compounds of the formula

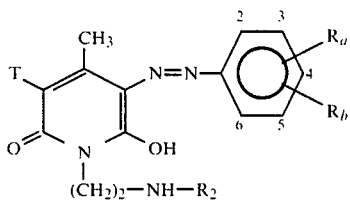

in which T, $R_2$, $R_a$ and $R_b$ are defined in Table 5 below and significances $T_{2-7}$ and $A_{2-4}$ are defined under Examples 13 to 44, can be prepared by a method analogous to that of Example 107.

| Ex. No. | T | $R_2$ | Significance of $R_a$ and position in phenyl ring | Significance of $R_b$ and position in phenyl ring |
|---|---|---|---|---|
| 108 | H | $A_2$ | H | H |
| 109 | $T_2$ | $A_3$ | 3-Cl | H |
| 110 | $T_3$ | $A_2$ | 4-Cl | H |
| 111 | $T_4$ | H | H | H |
| 112 | $T_4$ | H | 2-$NO_2$ | H |
| 113 | $T_4$ | H | 2-$NO_2$ | 4-Cl |
| 114 | $T_4$ | $A_2$ | H | H |
| 115 | $T_4$ | $A_2$ | 2-$NO_2$ | —H |
| 116 | $T_4$ | $A_2$ | 2-Cl | 4-$NO_2$ |
| 117 | $T_4$ | $A_2$ | 4-O—⟨phenyl⟩-Cl | H |
| 118 | $T_4$ | $A_3$ | H | H |
| 119 | $T_4$ | $A_4$ | 2-$NO_2$ | 4-Cl |
| 120 | $T_4$ | $A_4$ | 4-$OCH_3$ | —H |
| 121 | $T_5$ | H | H | H |
| 122 | $T_5$ | $A_2$ | 4-$NO_2$ | —H |
| 123 | $T_5$ | $A_2$ | 2-Cl | 4-$NO_2$ |
| 124 | $T_5$ | $A_4$ | 4-O—⟨phenyl⟩-Cl | —H |
| 125 | $T_6$ | H | —H | H |
| 126 | $T_6$ | $A_2$ | 4-$NO_2$ | H |
| 127 | $T_6$ | $A_4$ | 2-Cl | 4-$NO_2$ |
| 128 | $T_7$ | $A_2$ | 2-$NO_2$ | 4-Cl |
| 129 | $T_7$ | $A_4$ | 4-O—⟨phenyl⟩-Cl | H |
| 130 | $T_4$ | $A_2$ | 2-$OCH_3$ | 5-$CH_3$ |
| 131 | $T_5$ | $A_4$ | 2-$OCH_3$ | 5-$OCH_3$ |
| 132 | $T_4$ | $A_4$ | 2-$CH_3$ | 3-$CH_3$ |

The dyestuffs of Examples 108 to 132 produce dyeings of a yellow tone. These dyestuffs are also useful for dyeing polyacrylonitrile in the mass.

EXAMPLE 133

Using suitable starting compounds, a compound of formula 133a

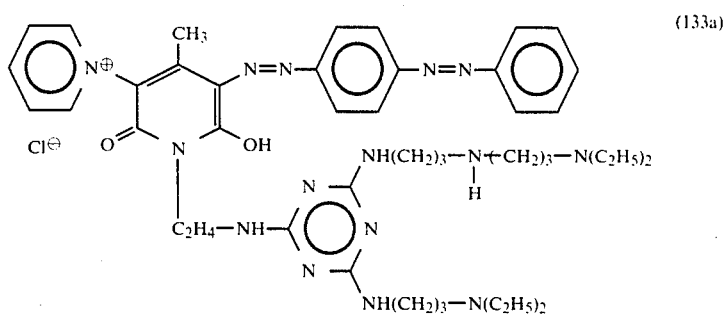

(133a)

may be prepared using an analogous method to Example 107.

Dyeings so produced are of a gold-yellow tone.

EXAMPLES 134 TO 139

Compounds of the formula

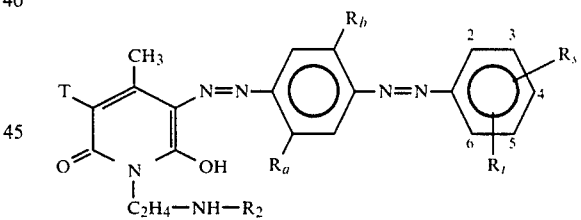

in which the symbols are given in Table 6 below may be prepared by known methods from suitable starting compounds.

TABLE 6

| EX. No. | T | $R_2$ | $R_a$ | $R_b$ | $R_s$ | $R_t$ |
|---|---|---|---|---|---|---|
| 134 | $T_5$ | $A_2$ | —$OCH_3$ | —$CH_3$ | 4-$CH_3$ | H |
| 135 | $T_7$ | $A_2$ | " | —$OCH_3$ | 2-$OCH_3$ | H |
| 136 | $T_4$ | $A_4$ | " | " | 2-$CH_3$ | 5-$CH_3$ |
| 137 | $T_6$ | $A_2$ | " | —$CH_3$ | 4-$C_4H_9$ | H |
| 138 | $T_5$ | $A_4$ | " | —$OCH_3$ | 2-$OCH_3$ | 5-$CH_3$ |
| 139 | $T_4$ | $A_2$ | —$CH_3$ | —$OCH_3$ | 2-$OCH_3$ | H |

The compounds of Examples 134 to 139 produce dyeings of gold-yellow to orange tones and have good fastness properties.

EXAMPLES 140 TO 162

Compounds of the formula

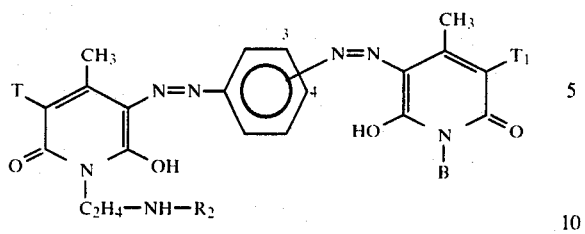

in which the symbols are defined in Table 7 below (symbols $T_{2-7}$ and $A_{2-4}$ are defined under Examples 13 to 44 and symbols $B_{2-11}$ are defined under Examples 47 to 64) may be made by analogous methods to that of Example 107 from suitable starting compounds.

TABLE 7

| EX. No. | T | $R_2$ | position of floating azo group | $T_1$ | B |
|---|---|---|---|---|---|
| 140 | $T_4$ | $A_2$ | 4 | $T_4$ | $B_6$ |
| 141 | H | $A_2$ | 4 | H | H |
| 142 | $T_2$ | $A_2$ | 4 | $T_3$ | $B_2$ |
| 143 | $T_3$ | $A_4$ | 4 | $T_4$ | $B_3$ |
| 144 | $T_4$ | H | 4 | H | $B_4$ |
| 145 | $T_5$ | H | 4 | H | $B_5$ |
| 146 | H | $A_2$ | 4 | $T_4$ | $B_6$ |
| 147 | $T_6$ | $A_2$ | 4 | $T_2$ | $B_7$ |
| 148 | $T_7$ | $A_2$ | 4 | H | $B_8$ |
| 149 | H | H | 4 | $T_4$ | $B_9$ |
| 150 | H | $A_2$ | 4 | H | $B_8$ |
| 151 | H | $A_4$ | 4 | H | $B_9$ |
| 152 | $T_4$ | H | 3 | $T_4$ | $B_6$ |
| 153 | $T_5$ | H | 3 | $T_5$ | $B_6$ |
| 154 | $T_4$ | H | 4 | $T_4$ | $B_6$ |
| 155 | $T_5$ | H | 3 | $T_5$ | $B_6$ |
| 156 | $T_4$ | $A_2$ | 3 | $T_5$ | H |
| 157 | $T_5$ | $A_4$ | 3 | $T_6$ | H |
| 158 | $T_3$ | $A_2$ | 3 | $T_5$ | $B_2$ |
| 159 | $T_4$ | H | 4 | $T_4$ | $B_{10}$ |
| 160 | $T_5$ | $A_2$ | 3 | $T_4$ | $B_{10}$ |
| 161 | $T_5$ | $A_2$ | 4 | $T_4$ | $B_{11}$ |
| 162 | $T_4$ | H | 3 | $T_4$ | $B_{11}$ |

Compounds of Examples 140, to 151, 154, 159 and 162 produce dyeings of dyeings of a violet tone whereas the compounds of Examples 152, 153, 155 to 158, 160 and 161 produce dyeings of a reddish yellow to orange tone.

EXAMPLES 163 TO 186

Compounds of the formula

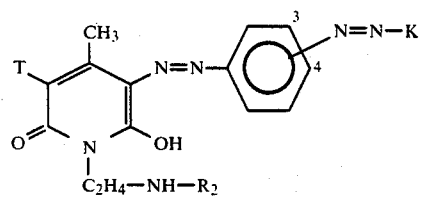

in which the symbols are defined in Table 8 below, may be prepared by an analogous method to that of Example 107. Symbols $T_{2-4}$ and $A_{2-4}$ are defined under Examples 13 to 44 and symbols $K_{1-17}$ are given below.

Compounds of Examples 163 to 168, 179 and 185 produce dyeings of a red shade, of Examples 169 to 175, 183 and 184 a yellow tone, of Examples 176 to 178 a blue tone and of Examples 180 to 182 and 186 an orange tone.

$K_1$ represents

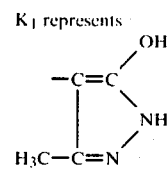

$K_2$ represents

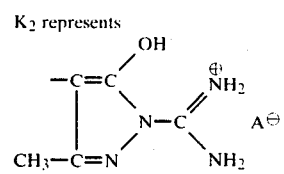

$K_3$ represents

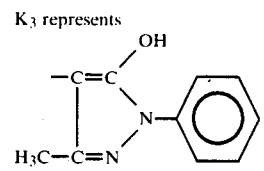

$K_4$ represents

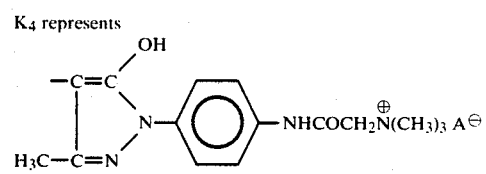

$K_5$ represents

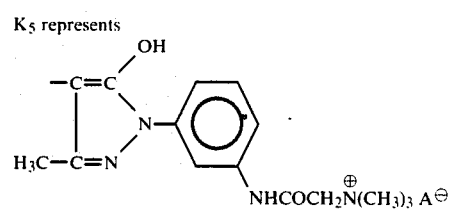

$K_6$ represents

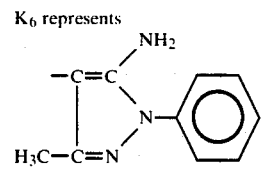

$K_7$ represents

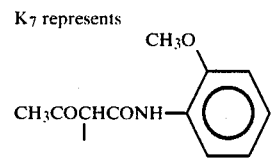

$K_8$ represents

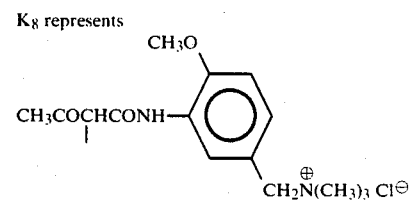

K₉ represents

CH₃COCHCO—NH—⟨phenyl⟩—NH—⟨triazine with NH(CH₂)₃N(C₂H₅)₂ groups⟩

K₁₀ represents

CH₃COCHCONH—⟨phenyl⟩—NH—⟨triazine with NH(CH₂)₃N(C₂H₅)₂ groups⟩

K₁₁ represents

CH₃COCHCONH—⟨phenyl⟩—NHCOCH₂N⁺(CH₃)₃ Cl⁻

K₁₂ represents

CH₃COCHCONH—⟨phenyl⟩ with NHCOCH₂N⁺(CH₃)₃ Cl⁻

K₁₃ represents

CH₃COCHCONH—⟨phenyl⟩—SO₂NH(CH₂)₃N(CH₃)₂

K₁₄ represents

⟨naphthyl with OH and CONH(CH₂)₃N(CH₃)₂⟩

K₁₅ represents

⟨phenyl⟩—N(C₂H₄CN)(C₂H₅)

K₁₆ represents

⟨phenyl⟩—N(C₂H₄—N⁺pyridinium Cl⁻)(C₂H₅)

K₁₇ represents

⟨pyridine with CN, NH—(CH₂)₃N(CH₃)₂, H₃C, CH₃, NH—(CH₂)₃N(CH₃)₂⟩

K₁₈ represents

⟨phenyl⟩—OH

TABLE 8

| EX. No. | T | R₂ | Position of floating azo group | K |
|---|---|---|---|---|
| 163 | T₄ | A₂ | 4- | K₁ |
| 164 | T₅ | A₂ | 4- | K₂ |
| 165 | T₆ | A₂ | 4- | K₃ |
| 166 | T₄ | A₄ | 4- | K₄ |
| 167 | T₅ | A₄ | 4- | K₅ |
| 168 | T₂ | A₂ | 4- | K₆ |
| 169 | H | A₂ | 4- | K₇ |
| 170 | T₄ | A₄ | 4- | K₈ |
| 171 | H | A₄ | 4- | K₉ |
| 172 | T₅ | H | 4- | K₁₀ |
| 173 | T₅ | A₄ | 4- | K₁₁ |
| 174 | T₆ | A₄ | 4- | K₁₂ |
| 175 | T₇ | A₂ | 4- | K₁₃ |
| 176 | T₄ | A₂ | 4- | K₁₄ |
| 177 | T₄ | A₂ | 4- | K₁₅ |
| 178 | T₅ | A₄ | 4- | K₁₆ |
| 179 | T₆ | A₂ | 4- | K₁₇ |
| 180 | T₅ | A₂ | 4- | K₁₈ |
| 181 | T₄ | A₂ | 3- | K₁ |
| 182 | T₆ | H | 3- | K₅ |
| 183 | T₇ | H | 3- | K₈ |
| 184 | T₃ | A₄ | 3- | K₁₂ |
| 185 | T₄ | A₂ | 3- | K₁₄ |
| 186 | T₅ | H | 3- | K₁₇ |

EXAMPLES 187 TO 243

According to a method analogous to that of Example 107 compounds of formula

⟨bis-azo structure: two pyridone units linked via azo—phenyl—X—phenyl—azo, each pyridone bearing CH₃, OH, =O, N—(CH₂)₂—NH—R₂⟩ in which the symbols are defined in Table 9 below (where the symbols $A_{2-4}$ and $R_{2-7}$ are defined under Examples 13 to 44 and those symbols of $X_{1-108}$ used in Table 9 are defined below) can be prepared.

The symbols $X_1$ to $X_{108}$ used in Table 9 are as follows:

$X_1$ is a direct bond $X_5$ —S—, $X_6$ —O—, $X_7$ —CH=CH—, $X_{10}$ —NH—, $X_{11}$ —NH—CO—, $X_{12}$

—N—CO—,
 |
 CH₃

$X_{16}$ 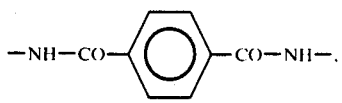

$X_{17}$ —SO$_2$—NH—, $X_{22}$ —CO—NH—NH—CO—,

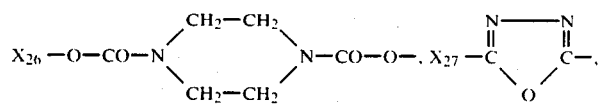

$X_{30}$ —C—C—,  $X_{45}$ —CH$_2$—NH—CO—NH—CH$_2$—,  $X_{49}$ —CH$_2$—CO—CH$_2$—,
       ‖ ‖
       O O $X_{50}$ —CH=CH—CH=CH—, 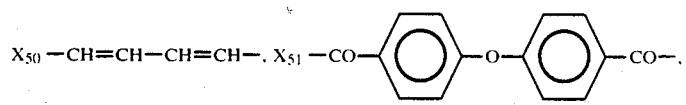

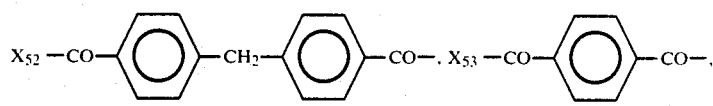

$X_{54}$ 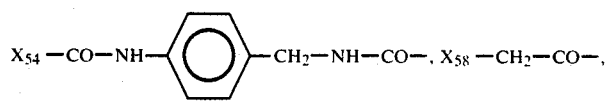 $X_{58}$ —CH$_2$—CO—, $X_{59}$ —CH=CH—CO—CH=CH—, $X_{60}$ 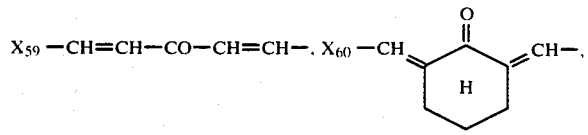

$X_{61}$ 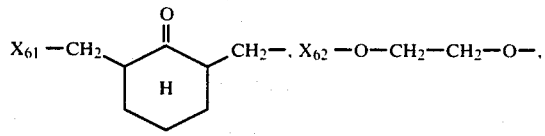 $X_{62}$ —O—CH$_2$—CH$_2$—O—, $X_{64}$ —CO—NH—R$_{43}$—CO—NH—, $X_{70}$ —NH—CO—NH—, $X_{71}$ 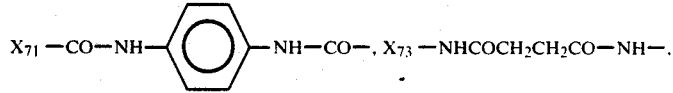 $X_{73}$ —NHCOCH$_2$CH$_2$CO—NH—, $X_{74}$ —NH—CO—CH=CH—CO—NH— $X_{75}$ —NH—CO(CH$_2$)$_4$—CO—NH—,

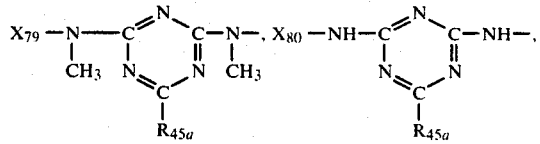

$X_{81}$ —CH$_2$—, $X_{82}$ —(CH$_2$)$_2$—, $X_{85}$ —CO—NH—(CH$_2$)$_2$—NH—CO—, $X_{86}$ —CO—NH—(CH$_2$)$_3$—NH—CO—, $X_{87}$ —CO—NH—(CH$_2$)$_4$—NH—CO—, $X_{88}$ —CO—N—(CH$_2$)$_2$—N—CO—, $X_{89}$ —CO—NH—CH$_2$—CH—NH—CO—,
         |           |                              |
         CH$_3$      CH$_3$                         CH$_3$ $X_{90}$ —CO—NH—CH—CH—NH—CO—,
              |    |
              H$_3$C  CH$_3$ $X_{100}$ —CO—NH—R$_{43}$—CO—NH—R$_{43}$—NH—CO—.

-continued $X_{101}$ —CO—NH—$R_{43}$—NH—CO—$CH_2$—$CH_2$—CO—NH—$R_{43}$—NH—CO—, $X_{102}$ —CO—NH—$R_{43}$—NH—CO—CH=CH—CO—NH—$R_{43}$—NH—CO—,

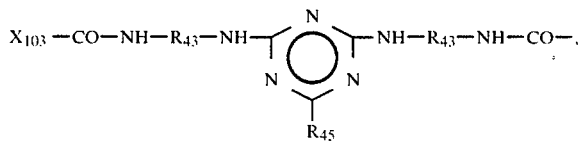

$X_{103}$ —CO—NH—$R_{43}$—NH—[triazine with $R_{45}$]—NH—$R_{43}$—NH—CO—, $X_{104}$ —$SO_2$—$NR_{44}$—$(CH_2)_q$—$NR_{44}$—$SO_2$—, $X_{105}$ —CO—$NR_{44}$—$R_{43}$—O—CO—,

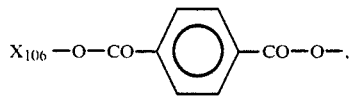

$X_{106}$ —O—CO—[phenylene]—CO—O—,

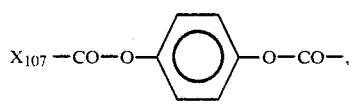

$X_{107}$ —CO—O—[phenylene]—O—CO—, $X_{108}$ —CONH—$R_{43}$—NH—CO—NH—$R_{43}$—NH—CO—,

TABLE 9

| EX. No. | T | $R_2$ | X |
|---|---|---|---|
| 187 | H | $A_2$ | $X_1$ |
| 188 | $T_2$ | $A_2$ | $X_5$ |
| 189 | $T_3$ | $A_2$ | $X_6$ |
| 190 | $T_4$ | $A_4$ | $X_7$ |
| 191 | $T_5$ | $A_4$ | $X_{10}$ |
| 192 | $T_6$ | $A_2$ | $X_{11}$ |
| 193 | $T_7$ | $A_2$ | $X_{12}$ |
| 194 | $T_4$ | $A_2$ | $X_{16}$ |
| 195 | H | $A_2$ | $X_{17}$ |
| 196 | $T_4$ | $A_4$ | $X_{22}$ |
| 197 | H | $A_2$ | $X_{26}$ |
| 198 | $T_4$ | $A_4$ | $X_{27}$ |
| 199 | $T_5$ | H | $X_{30}$ |
| 200 | $T_6$ | $A_2$ | $X_{45}$ |
| 201 | $T_7$ | $A_2$ | $X_{49}$ |
| 202 | $T_4$ | $A_4$ | $X_{50}$ |
| 203 | $T_5$ | $A_2$ | $X_{51}$ |
| 204 | $T_6$ | $A_2$ | $X_{52}$ |
| 205 | $T_7$ | $A_2$ | $X_{53}$ |
| 206 | H | $A_2$ | $X_{54}$ |
| 207 | $T_2$ | $A_2$ | $X_{58}$ |
| 208 | $T_4$ | $A_4$ | $X_{59}$ |
| 209 | $T_5$ | H | $X_{60}$ |
| 210 | $T_6$ | $A_2$ | $X_{61}$ |
| 211 | $T_7$ | $A_4$ | $X_{62}$ |
| 212 | $T_4$ | $A_2$ | $X_{70}$ |
| 213 | H | $A_2$ | $X_{71}$ |
| 214 | $T_2$ | $A_2$ | $X_{73}$ |
| 215 | $T_4$ | $A_2$ | $X_{74}$ |
| 216 | $T_5$ | $A_4$ | $X_{75}$ |
| 217 | $T_6$ | $A_2$ | $X_{79}$ |
| 218 | $T_4$ | $A_2$ | $X_{80}$ |
| 219 | $T_5$ | $A_2$ | $X_{81}$ |
| 220 | $T_4$ | $A_2$ | $X_{82}$ |
| 221 | $T_4$ | $A_2$ | $X_{85}$ |
| 222 | $T_5$ | $A_2$ | $X_{86}$ |
| 223 | $T_6$ | H | $X_{87}$ |
| 224 | $T_7$ | $A_3$ | $X_{88}$ |
| 225 | $T_2$ | $A_2$ | $X_{89}$ |
| 226 | $T_3$ | $A_4$ | $X_{90}$ |
| 227 | $T_4$ | $A_2$ | $X_{103}$ ($R_{43}$ = $C_2H_4$—, $R_{45}$ = NH—$(CH_2)_{2-3}$—$N(C_2H_5)_2$) |
| 228 | $T_5$ | $A_2$ | $X_{107}$ |
| 229 | H | $A_2$ | —CONH$(CH_2)_2$CONH$(CH_2)_2$NHCO— |
| 230 | $T_2$ | $A_2$ | —CONH$(CH_2)_2$CONH$(CH_2)_2$NHCO— |
| 231 | $T_3$ | $A_2$ | —CONH$C_2H_4$NHCOCH=CHCONH$C_2H_4$NHCO— |
| 232 | $T_4$ | $A_3$ | —CONH$C_2H_4$NHCO$C_2H_4$CONH$C_2H_4$NHCO— |
| 233 | $T_5$ | $A_4$ | $X_{107}$ |
| 234 | $T_5$ | $A_2$ | —CONH—$C_2H_4$NH—[triazine with NH$C_2H_4$NHCO— and NH$C_2H_4$OH]— |
| 235 | $T_4$ | $A_2$ | —CONH$C_2H_4$NH—[triazine with NH$C_2H_4$NHCO— and $H_3C$—N—phenyl]— |
| 236 | $T_4$ | H | $X_{11}$ |
| 237 | $T_4$ | H | $X_{85}$ |
| 238 | $T_4$ | H | $X_{82}$ |
| 239 | $T_4$ | H | $X_{71}$ |
| 240 | $T_4$ | $A_2$ | $X_{11}$ |
| 241 | $T_4$ | $A_2$ | $X_{85}$ |
| 242 | $T_4$ | $A_2$ | $X_{82}$ |
| 243 | $T_4$ | $A_2$ | $X_{71}$ |

Compounds of Examples 187 and 212 dye paper a red tone; Compounds of Examples 188 to 190, 194 to 197, 199 to 201, 203 to 211, 214 to 216 to 235, 237, 238, 240 to 243 dye paper a yellow tone; the compound of Example 191 dyes paper a blue tone and compounds of Examples 192, 193, 198, 202, 213, 217 to 218 and 236 to 239 dye paper an orange tone.

EXAMPLE 244

Using suitable starting compounds and a method analogous to that of Example 107, a compound of the formula

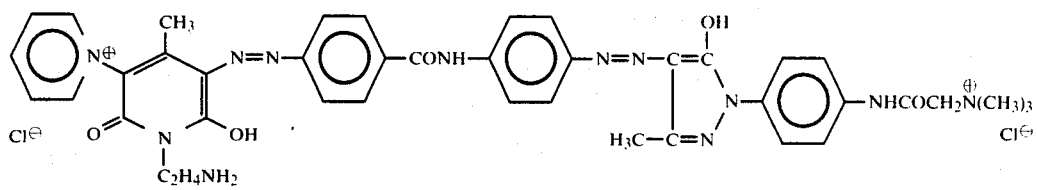

may be prepared. This compound dyes paper a red-yellow tone.

EXAMPLES 245 TO 258

Compounds of formula

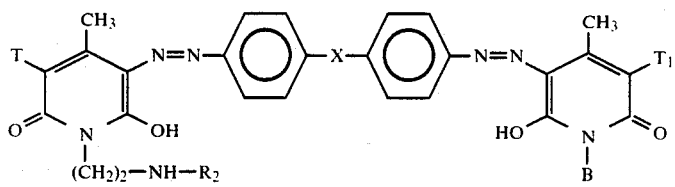

in which the symbols are given in Table 10 below and symbols $A_{2-4}$ and $T_{2-7}$ are given under Examples 13 to 44, $B_{2-11}$ are defined under Examples 47 to 64; $K_{1-17}$ are defined under Examples 163 to 186 and the symbols $X_{1-108}$ used in Table 10 are defined under Examples 187 to 243.

Compounds of Examples 245, 252 and 258 dye paper a red tone, compounds of Examples 246, 248, and 257 dye paper an orange tone, the compound of Example 247 dyes paper a blue tone and the compounds of Examples 249 to 251 and 253 to 256 dye paper a yellow tone.

TABLE 10

| EX. No. | T | $R_2$ | $T_1$ | B | X |
|---|---|---|---|---|---|
| 245 | H | $A_2$ | $T_4$ | H | $X_1$ |
| 246 | $T_2$ | $A_2$ | $T_5$ | $B_2$ | $X_2$ |
| 247 | $T_3$ | $A_3$ | $T_6$ | $B_3$ | $X_{10}$ |
| 248 | $T_4$ | H | H | $B_4$ | $X_{11}$ |
| 249 | $T_5$ | $A_2$ | $T_4$ | $B_6$ | $X_{51}$ |
| 250 | $T_6$ | $A_2$ | $T_5$ | $B_7$ | $X_{53}$ |
| 251 | $T_7$ | $A_2$ | H | $B_9$ | $X_{59}$ |
| 252 | $T_4$ | $A_4$ | $T_5$ | H | $X_{70}$ |
| 253 | $T_5$ | $A_2$ | H | H | $X_{81}$ |
| 254 | $T_4$ | $A_4$ | $T_2$ | $B_4$ | $X_{82}$ |
| 255 | $T_5$ | $A_2$ | $T_4$ | H | $X_{25}$ |
| 256 | $T_4$ | $A_4$ | $T_4$ | H | $X_{86}$ |
| 257 | $T_4$ | $A_2$ | $T_4$ | $B_{10}$ | $X_{11}$ |
| 258 | $T_4$ | $A_2$ | $T_4$ | $B_{11}$ | $X_{70}$ |

EXAMPLES 259 TO 268

Compounds of the formula

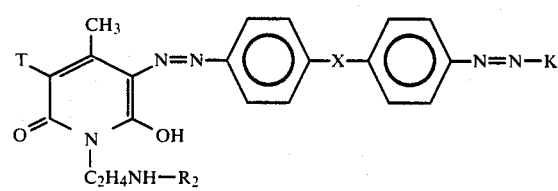

in which the symbols are given in Table 11 below, may be prepared in a manner analogous to that of Example 107

TABLE 11

| EX. No. | T | $R_2$ | X | K |
|---|---|---|---|---|
| 259 | $T_4$ | $A_2$ | $X_1$ | $K_1$ |
| 260 | $T_5$ | $A_2$ | $X_6$ | $K_4$ |
| 261 | H | $A_4$ | $X_{11}$ | $K_5$ |
| 262 | $T_4$ | H | $X_{18}$ | $K_7$ |
| 263 | $T_5$ | $A_4$ | $X_{55}$ | $K_8$ |
| 264 | $T_4$ | $A_2$ | $X_{59}$ | $K_{10}$ |
| 265 | $T_6$ | $A_4$ | $X_{70}$ | $K_{11}$ |
| 266 | $T_7$ | $A_2$ | $X_{82}$ | $K_{16}$ |
| 267 | $T_4$ | $A_2$ | $X_{85}$ | $K_{17}$ |
| 268 | $T_5$ | $A_2$ | $X_{11}$ | $K_{14}$ |

The compound of Example 262 dyes paper a red tone, compounds of Examples 259 to 261 dye paper an orange tone and compounds of Examples 262 to 268 dye paper a yellow tone.

EXAMPLE 269

Starting with a monoazo compound of formula (269a)

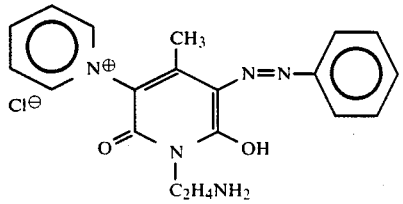

(269a)

and reacting with a cyanuric chloride derivative a compound of formula (269b)

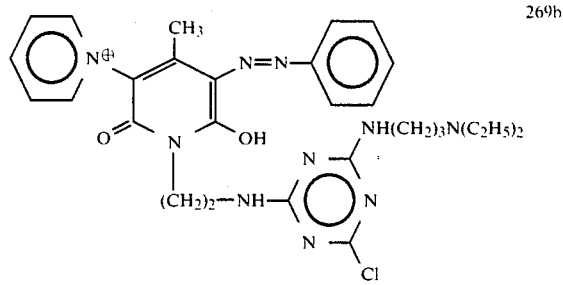

may be formed.

By reacting the compound of formula (269b) with the compound of formula (269c)

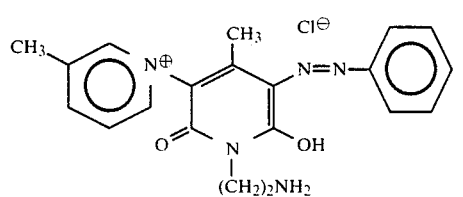

in water at 90° C. and at pH 9, a compound of formula 269d

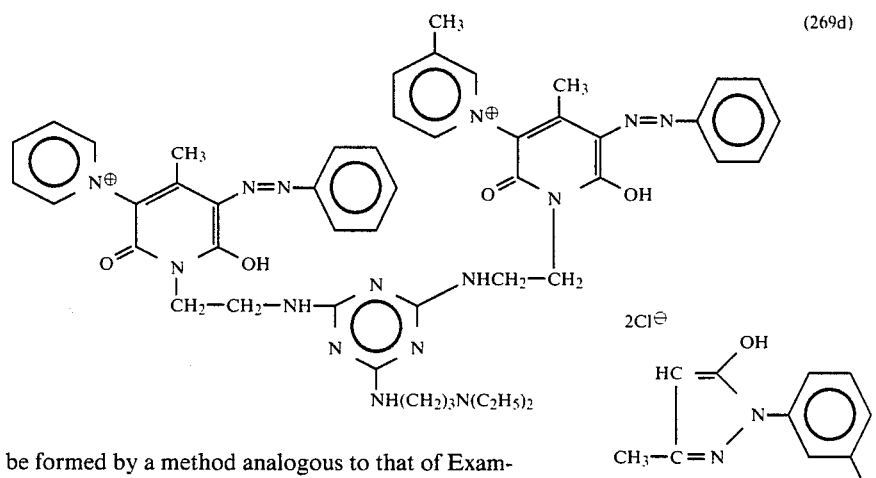

may be formed by a method analogous to that of Example 1. The compound of Example 269d dyes paper a yellow tone.

EXAMPLE 270

A compound of formula 270a

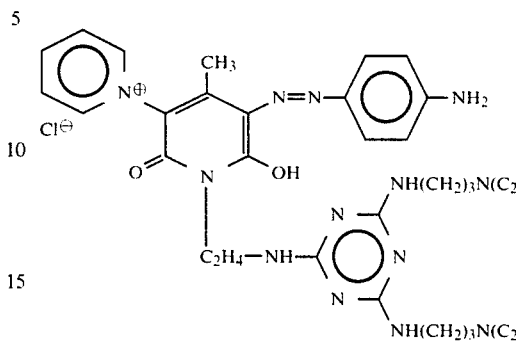

is diazotised and then coupled to 2-amino-1,4-dimethylbenzene. The resulting disazo compound is further diazotised and then coupled to a compound of the formula H—K$_5$

H-K$_5$ to form a compound formula 270b

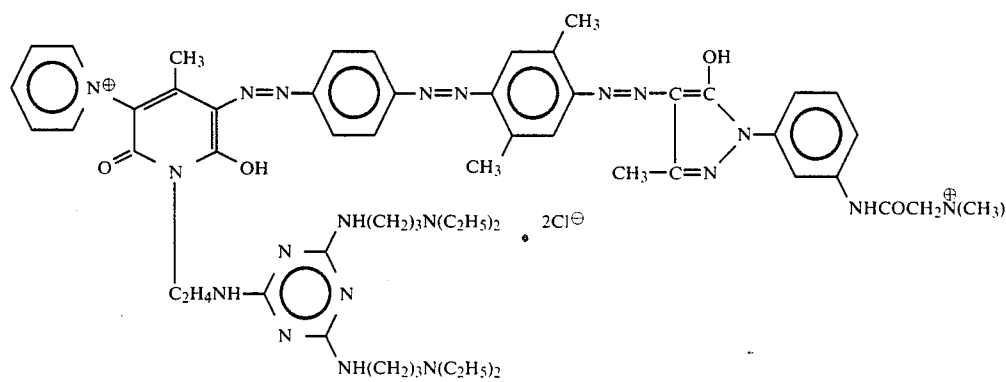

This dyestuff dyes paper a brown tone. Instead of coupling to 2-amino-1,4-dimethylbenzene, an equivalent amount of 2-methoxy-5-methylaniline will produce a compound of formula 270c

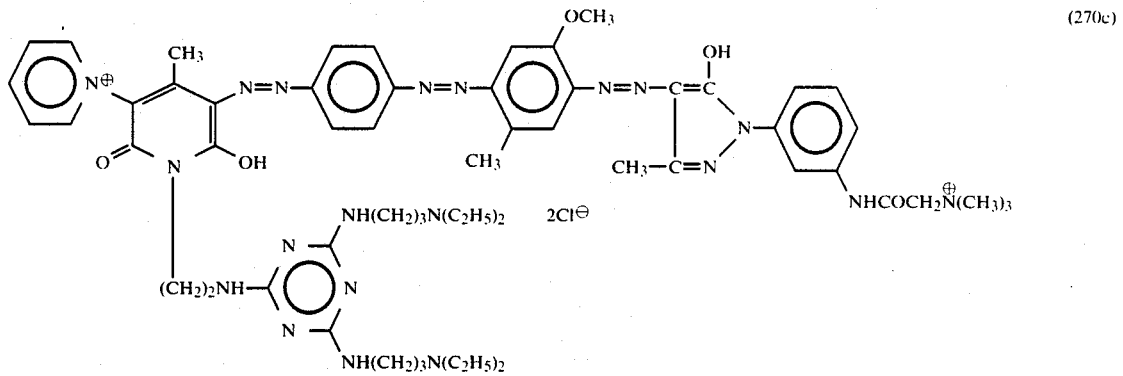

results.

The compound 270c dyes paper a brown tone.

The compound 270c can be metallised by known methods with such metals as copper, to form a compound of formula 270d

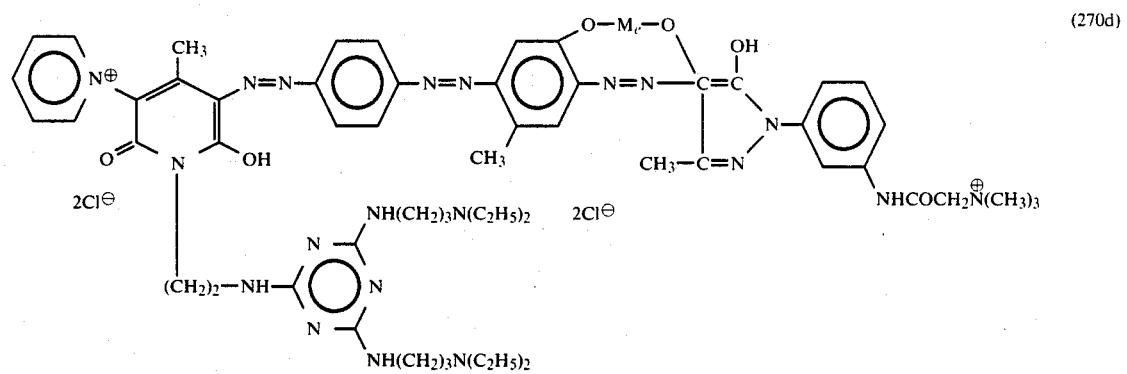

where $M_e$ is copper.

EXAMPLES 271 TO 283

Compounds of the formula

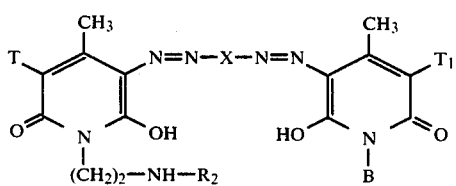

where the symbols are defined in Table 12 below may be made by a method analogous to that of Example 270 and then metallised. Symbols $B_{2-11}$ are given under Examples 47 to 64 and symbols $A_{2-4}$ and $T_{2-7}$ are given under Examples 13 to 44.

The compounds of Examples 271 to 273 and 277 to 281 dye paper a violet tone and compounds of Examples 274 to 276 and 282 to 283 dye paper a blue tone.

TABLE 12

| EX. No. | T | $R_2$ | $T_1$ | B | X |
|---|---|---|---|---|---|
| 271 | $T_5$ | $A_2$ | $T_5$ | $B_8$ | 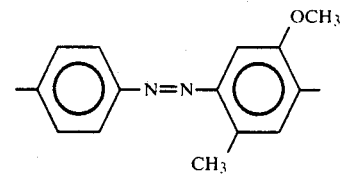 |
| 272 | $T_4$ | $A_4$ | $T_3$ | $B_4$ | 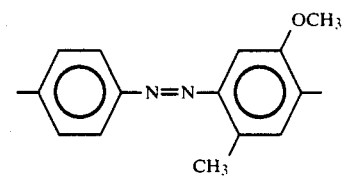 |
| 273 | $T_2$ | $A_2$ | $T_6$ | $B_6$ | 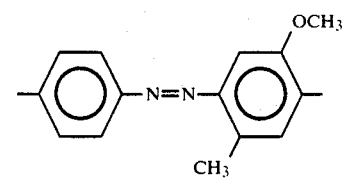 |
| 274 | H | $A_2$ | $T_4$ | $B_8$ | 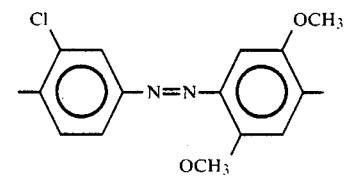 |

TABLE 12-continued

| EX. No. | T | $R_2$ | $T_1$ | B | X |
|---|---|---|---|---|---|
| 275 | H | $A_2$ | $T_5$ | H | (Cl, OCH$_3$, OCH$_3$-substituted azobenzene) |
| 276 | $T_4$ | $A_2$ | $T_7$ | $B_2$ | (Cl, OCH$_3$, OCH$_3$-substituted azobenzene) |
| 277 | $T_4$ | H | $T_4$ | $B_6$ | (CH$_3$, CH$_3$, CH$_3$-substituted azobenzene) |
| 278 | $T_5$ | $A_2$ | $T_4$ | $B_3$ | (CH$_3$, CH$_3$, CH$_3$-substituted azobenzene) |
| 279 | $T_4$ | $A_2$ | $T_4$ | $B_8$ | (CH$_3$, CH$_3$, CH$_3$-substituted azobenzene) |
| 280 | $T_4$ | $A_2$ | $T_4$ | $B_8$ | (OCH$_3$, CH$_3$-substituted azobenzene) |
| 281 | $T_5$ | $A_4$ | $T_7$ | H | (OCH$_3$, CH$_3$-substituted azobenzene) |
| 282 | $T_4$ | $A_2$ | $T_4$ | $B_8$ | (OCH$_3$, OCH$_3$-substituted azobenzene) |
| 283 | $T_5$ | $A_4$ | $T_7$ | H | (OCH$_3$, OCH$_3$-substituted azobenzene) |

EXAMPLES 284 TO 297

In a similar manner to the method of Example 270, compounds of the formula

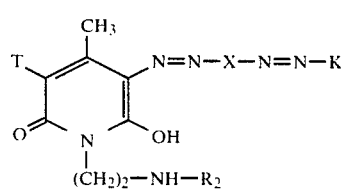

where the symbols are defined in Table 13 below, can be prepared. Symbols $K_{2-17}$ are defined under Examples 163 to 186.

The compounds of Examples 284 to 289 and 292 to 295 dye paper a violet tone and compounds of Examples 290, 291, 296 and 297 dye paper a blue tone.

TABLE 13

| EX. No. | T | $R_2$ | K | X |
|---|---|---|---|---|
| 284 | $T_5$ | $A_2$ | $K_5$ | (Cl, CH$_3$, CH$_3$-substituted azobenzene) |
| 285 | $T_6$ | $A_4$ | $K_9$ | (Cl, CH$_3$, CH$_3$-substituted azobenzene) |
| 286 | H | H | $K_{17}$ | (Cl, CH$_3$, CH$_3$-substituted azobenzene) |
| 287 | $T_4$ | $A_2$ | $K_3$ | (OCH$_3$, CH$_3$-substituted azobenzene) |

TABLE 13-continued

| EX. No. | T | R₂ | K | X |
|---|---|---|---|---|
| 288 | $T_5$ | $A_2$ | $K_{10}$ | 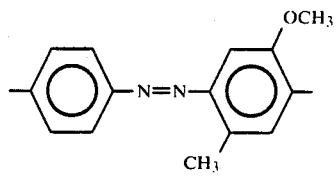 |
| 289 | $T_6$ | $A_2$ | $K_8$ | 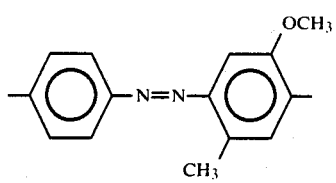 |
| 290 | $T_4$ | $A_2$ | $K_4$ | 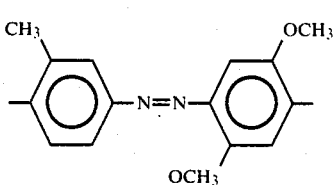 |
| 291 | $T_7$ | $A_4$ | $K_{16}$ | 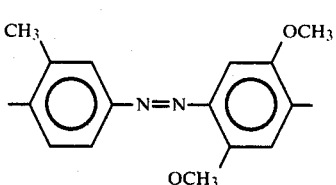 |
| 292 | $T_4$ | $A_2$ | $K_{11}$ | 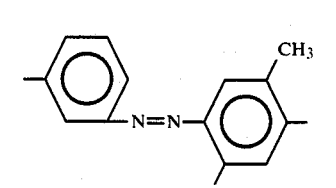 |
| 293 | $T_5$ | $A_4$ | $K_{14}$ | 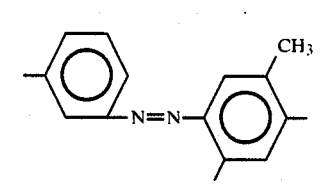 |
| 294 | $T_4$ | $A_2$ | $K_2$ | 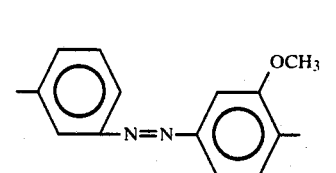 |
| 295 | $T_4$ | $A_2$ | $K_{13}$ | 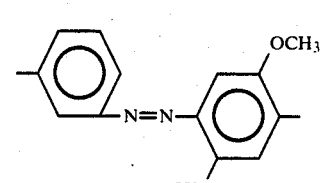 |

TABLE 13-continued

| EX. No. | T | R₂ | K | X |
|---|---|---|---|---|
| 296 | $T_4$ | $A_2$ | $K_{10}$ | 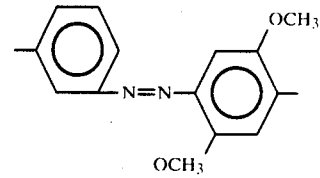 |
| 297 | $T_5$ | $A_2$ | $K_5$ | 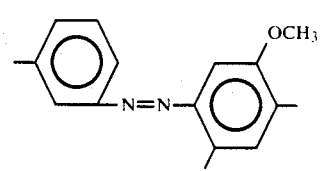 |

EXAMPLES 298 TO 300

Compounds of the formula

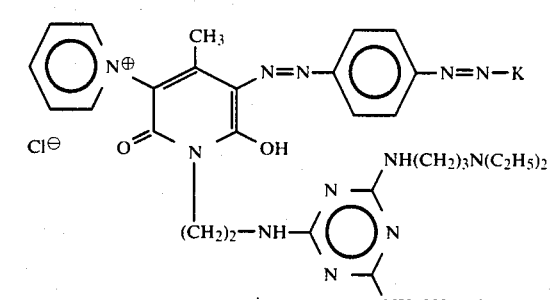

may be formed by diazotising a compound of formula 270a and then coupling with a compound H—K where K is Example 298

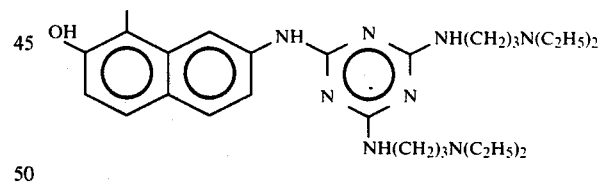

Example 299

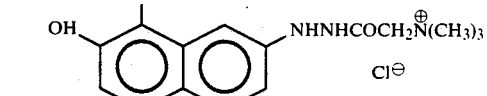

Example 300

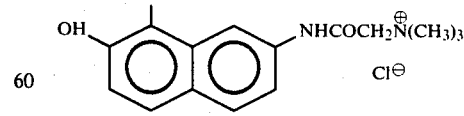

The coupling components H—K can be made from known compounds by known methods.

EXAMPLE 301

(a) Preparation of a coupling component of formula 301a

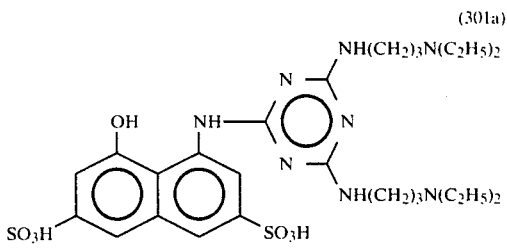
(301a)

91 Parts of cyanuric chloride are suspended in 240 parts of an ice/water mixture. 133 Parts of N,N-diethylamino propylamine is added dropwise at 5° to 10° and the mixture is stirred for 3 hours after which 127 parts of 1-hydroxy-8-aminonaphthalene-3,6-disulphonic acid is added. The temperature is raised to 90° and the pH is held at 2.5 to 3 by the portionwise addition of 54 parts of sodium acetate. After 2 hours condensation is terminated. The solution is allowed to cool whilst stirring to 20° where the desired crystalline product deposits. The product is filtered and 265 parts of a grey product results containing 217 parts of the coupling component 301a.

(b) Preparation of an amino component of formula 301b

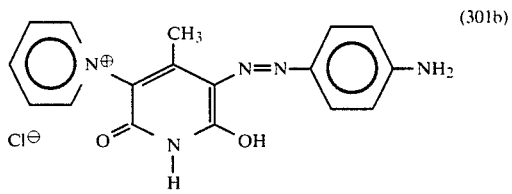
(301b)

30 Parts of 4-aminoacetanilide are reacted in 500 parts of an ice/water mixture at 0° C. with 50 parts of concentrated hydrochloric acid. After this addition, 55 parts of a 4N sodium nitrite solution is added dropwise followed by 42 parts of 6-hydroxy-4-methyl-3-pyridinium pyrid-2-one and this mixture is brought to pH 6 by the addition of sodium carbonate. Coupling occurs immediately and an orange dyestuff results. After coupling is completed the compound is filtered and the resulting press cake is suspended in 300 parts of water and then reacted with 100 parts of concentrated hydrochloric acid and heated to 95° C. The splitting off of the acetyl group is completed after 2 hours. The resulting solution is cooled to room temperature by stirring and the dyestuff of formula 301b falls out as yellow crystals. This is filtered, washed with brine and dried. 170 Parts of a yellow powder results containing 68 parts of the compound of formula 301b.

(c) Preparation of a compound of formula 301c 20.5 Parts of the compound of formula 301a are suspended in 200 parts of water and dissolved therein by the addition of sodium hydroxide.

22.4 Parts of the compound of formula 301b is diazotised by known methods and the resulting diazo solution is added dropwise to the compound of formula 301a, and the pH of the reaction is held at 8 to 9 by the addition of sodium hydroxide. Coupling occurs immediately to give a blue dyestuff. After termination of coupling the pH is reduced to 7.5 by the dropwise addition of concentrated hydrochloric acid and the dyestuff precipitates completely and then is filtered and dried. The dyestuff is blue in colour and in the form of its acid addition salt dyes paper a blue colour. The remaining dyebath is colourless. The wet-fastnesses of the dyeings so produced are good.

EXAMPLE 302

The compound of formula 301c may be prepared by coupling 4-aminoacetanilide to the compound of formula 301a, followed by saponifying in acid medium, diazotising and then coupling to 6-hydroxy-4-methyl-3-pyridinium-pyrid-2-one.

EXAMPLE 303

Instead of using 4-aminoaniline in the method of Example 301, p-nitroaniline is used, followed by reducing the nitro group in an alkali medium of a sulphuric acid salt. The resulting dyestuff is of formula 301c.

EXAMPLES 304 TO 340

Compounds of the formula

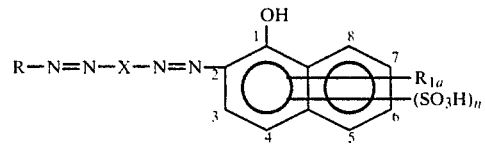

in which the symbols are defined in Table 14 below, can be prepared by methods analogous to Examples 301 to 303.

In these Examples $Y_1$ represents

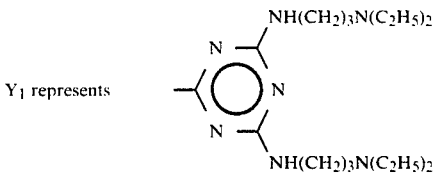

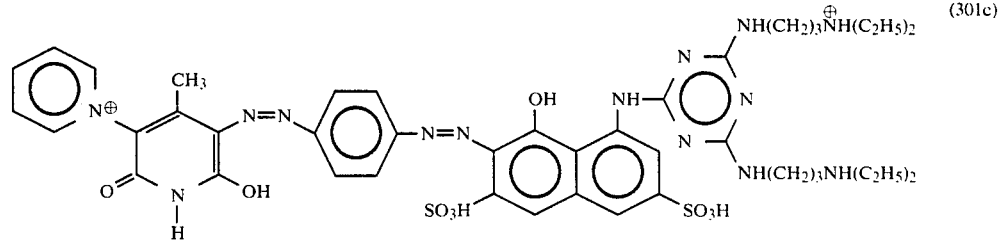
(301c)

-continued

Y₂ represents 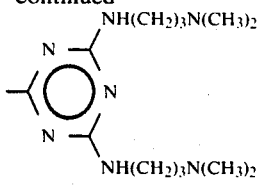

Y₃ represents 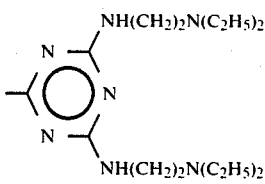

and

-continued

Y₄ represents 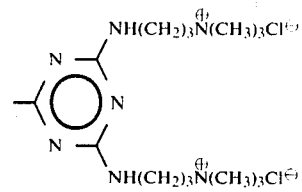

In group X the starred carbon atom is attached to the azo group attached to the pyridone.

In column I the numbers 1 to 9 represent the colour of the compound of the particular Example.

| 1 = orange | 2 = blueish-red | 3 = reddish-blue |
| 4 = blue | 5 = grey-blue | 6 = red-violet |
| 7 = blue-violet | 8 = violet | 9 = brown |

The position of groups is given by a figure in parentheses.

TABLE 14

| EX. No. | R | X | n and pos. of SO₃H group | R₁ₐ and position of R₁ₐ group | I |
|---|---|---|---|---|---|
| 304 | (pyridone structure with pyridinium, CH₃, Cl⁻, OH) | (phenylene) | 1 (3) | —NHC₃H₆N(CH₃)₂ (6) | 8 |
| 305 | " | " | " | —NH—Y₁ (6) | 7 |
| 306 | " | " | " | —NH—Y₂ (6) | 7 |
| 307 | " | " | " | —NH—Y₄ (6) | 7 |
| 308 | " | " | " | —NH—Y₁ (7) | 5 |
| 309 | " | " | " | —NH—Y₃ (7) | 5 |
| 310 | " | " | " | —NHCOCH₂⊕N(pyridinium)Cl⊖ (6) | 6 |
| 311 | " | " | 2 (3:6) | —NH—Y₂ (8) | 4 |
| 312 | " | " | " | —NH—Y₃ (8) | 4 |
| 313 | " | " | " | —NH—Y₄ (8) | 4 |
| 314 | " | (dimethylphenylene) | 1 (3) | —NH—Y₁ (6) | 1 |
| 315 | " | " | " | —NH—Y₂ (6) | 1 |
| 316 | " | " | 2 (3:6) | —NH—Y₁ (8) | 6 |
| 317 | " | " | " | —NH—Y₃ (8) | 6 |
| 318 | " | (methoxyphenylene, *C) | " | —NH—Y₁ (8) | 4 |
| 319 | " | " | " | —NH—Y₂ (8) | 4 |
| 320 | " | (chlorophenylene, *C) | " | —NH—Y₁ (8) | 4 |

TABLE 14-continued
| EX. No. | R | X | n and pos. of SO₃H group | $R_{1a}$ and position of $R_{1a}$ group | l |
|---|---|---|---|---|---|
| 321 | " | 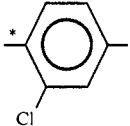 (*-phenyl with Cl) | " | " | 4 |
| 322 | " | 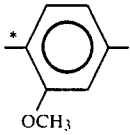 (*-phenyl with OCH₃) | " | " | 4 |
| 323 | " | 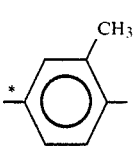 (*-phenyl with CH₃) | " | " | 4 |
| 324 | " | 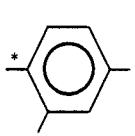 (*-phenyl with 2 CH₃) | " | " | 4 |
| 325 | " | " | " | —NH—Y₂ (8) | 4 |
| 326 | " | 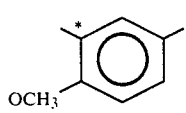 (*-phenyl with OCH₃) | " | —NH—Y₁ (8) | 3 |
| 327 | 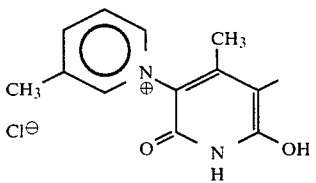 | 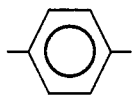 | " | " | 4 |
| 328 | " | " | " | —NH—Y₂ (8) | 4 |
| 329 | 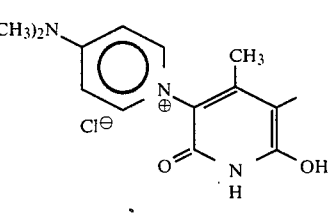 | " | " | —NH—Y₁ (8) | 4 |
| 330 | 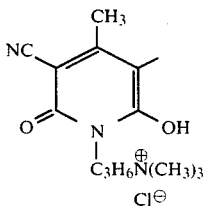 | " | " | " | 3 |

TABLE 14-continued

| EX. No. | R | X | n and pos. of SO₃H group | $R_{1a}$ and position of $R_{1a}$ group | l |
|---|---|---|---|---|---|
| 331 | ![structure: pyridinium-Cl⁻ substituted dihydroxypyridone with C₃H₆N(CH₃)₂] | " | " | " | 4 |
| 332 | " | " | " | —NH—Y₂ (8) | 4 |
| 333 | ![structure: pyridinium-Cl⁻ substituted phenyl dihydroxypyridone, NH] | " | " | —NH—Y₁ (8) | 4 |
| 334 | ![structure: NC, CH₃ dihydroxypyridone with phenyl-NHCOCH₂N⁺(CH₃)₃ Cl⁻] | " | " | " | 4 |
| 335 | ![structure: NC, CH₃ dihydroxypyridone with phenyl-NH—Y₁] | " | " | " | 4 |
| 336 | ![structure: pyridinium-Cl⁻ substituted dihydroxypyridone, NH] | *—C₆H₄—CONH—C₆H₄— | " | " | 9 |
| 337 | " | " | " | —NH—Y₃ (8) | 9 |
| 338 | " | ![dimethoxybiphenyl with OCH₃ groups] | " | —NH—Y₁ (8) | 4 |

TABLE 14-continued

| EX. No. | R | X | n and pos. of SO$_3$H group | R$_{1a}$ and position of R$_{1a}$ group | I |
|---|---|---|---|---|---|
| 339 | 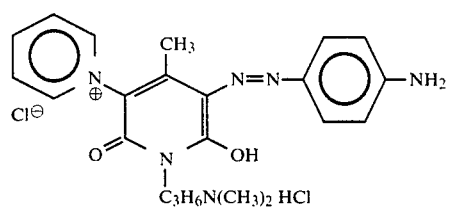 | -⌬- | 1 (4) | H | 2 |
| 340 | (structure with NC, CH$_3$, OH, N-H) | " | 0 | —NH—Y$_1$ (4) | 2 |

EXAMPLE 341

Starting with a compound of formula 341a

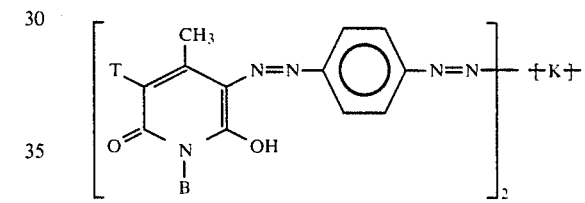
(341a)

a compound of formula 341b

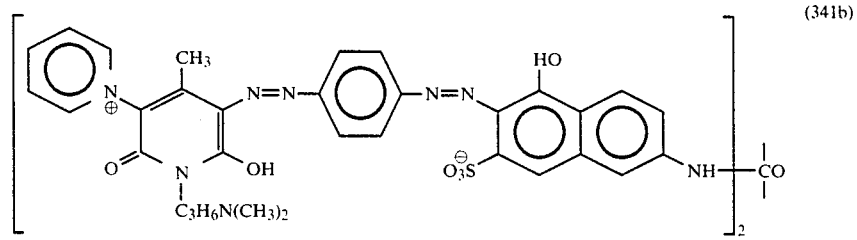
(341b)

can be prepared as follows.

The compound of formula 341a can be made by an analogous method to that of Example 45.

75 Parts of a compound of formula 341a are diazotised with 3 parts of a 4N sodium nitrite solution to which an alkali solution containing 2.5 parts of 5,5'-dihydroxy-7,7'-disulpho-2,2'-dinaphthyl urea is added dropwise. Coupling is fully completed by the addition of 10 parts of NaOH and a compound of formula 341b results having a blue tone.

EXAMPLES 342 TO 348

Compounds of the formula $$\left[ \begin{array}{c} \text{(pyridone structure with CH}_3\text{, T, B, N=N-⌬-N=N-)} \end{array} \right]_2 -\!\!\!+\!\!\!\text{K}\!\!\!+\!\!\!-$$

can be prepared by a method analogous to that of Example 341 using suitable starting materials. The symbols are defined in Table 15 below. In column I the colour numerals in column I are as for Examples 304 to 340 with additionally 10=brownish-red and 11=black.

TABLE 15

| EX. No. | T | B | —K— | I |
|---|---|---|---|---|
| 342 | (pyridinium Cl$^\ominus$) | —(CH$_2$)$_3$N(C$_2$H$_5$)$_2$ | (naphthalene with OH↘, SO$_3$H, NH$_2$↑) | 10 |
| 343 | " | —(CH$_2$)$_3$N(CH$_3$)$_2$ | " | 10 |

TABLE 15-continued

| EX. No. | T | B | —K— | I |
|---|---|---|---|---|
| 344 | " | " | 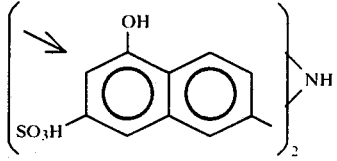 | 8 |
| 345 | " | " | 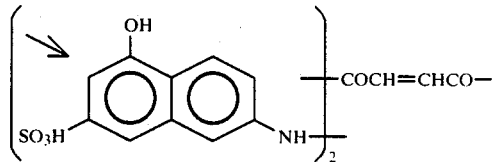 | 4 |
| 346 | 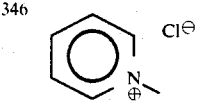 | —(CH$_2$)$_3$N(CH$_3$)$_2$ | 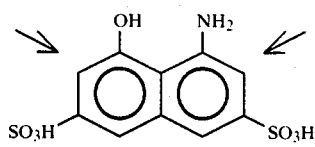 | 11 |
| 347 | CN | 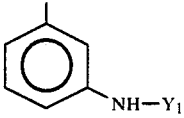 | " | 11 |
| 348 | " | 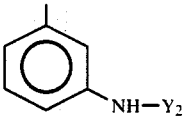 | " | 11 |

EXAMPLE 349

From appropriate starting compounds, a compound of formula 349a

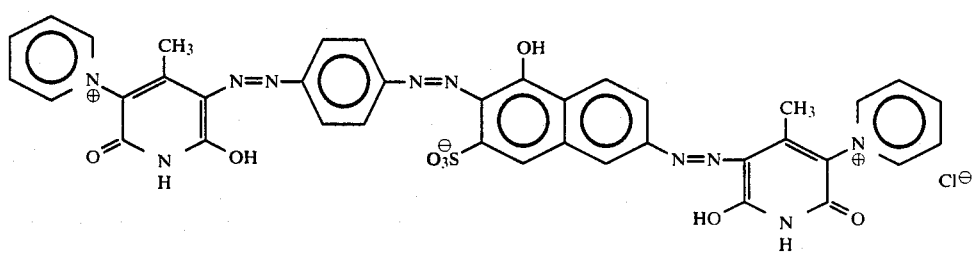

(349a)

can be prepared. The compound 349a dyes paper a grey-violet tone.

EXAMPLE 350

10 Parts of the dyestuff of Example 318 are stirred in 200 parts of water and warmed to 80°. A solution of 3 parts copper sulphate pentahydrate in 20 parts water and 15 parts of concentrated ammonia is poured into the dyestuff solution and the temperature is raised to 90° to 95°. After 4 hours metallisation is terminated, 30 parts of NaCl are added, the mixture is cooled to room temperature and finally 5 parts of sodium hydroxide are added dropwise.

A dyestuff of formula 350a

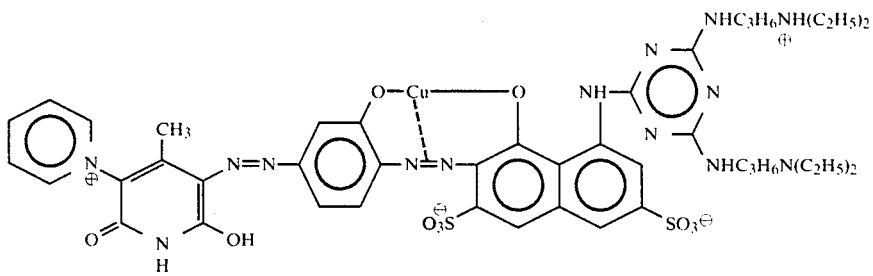

results. In acid addition salt form compound 350a dyes paper a grey brown tone. The spent liquor is practically colourless and the wet fastnesses and light fastnesses are excellent.

EXAMPLE 351

28 Parts of compound 301c powder are dissolved in 90 parts of water and 10 parts of lactic acid whilst stirring at 60°. Then the dyestuff solution is clear-filtered. One obtains 125 parts of a filtrate which is stable to storage for several months and which neither under warm nor cold conditions allows the dyestuff to be deposited. This dyestuff solution may be used directly (or thinned with water) in dyeing paper.

EXAMPLE 352

24 Parts of the compound 301c powder are stirred into 500 parts of water and then the mixture is acidified with 5 parts of glacial acetic acid. The dyestuff dissolves in solution and then the solution is dried. A compound of formula 352a

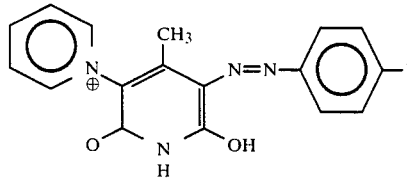 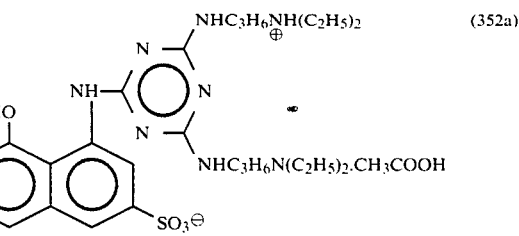

results, having in powder form a high solubility in cold water.

In Examples 351 and 352 instead of the acids used, such acids as hydrochloric, sulphuric, phosphoric and formic acids may be used and instead of the dyestuff 301c any of the compounds of Examples 302 to 350 may be used.

EXAMPLE 353

80 Parts of the dyestuff of 301c powder are stirred into a solution of 20 parts dextrin, 20 parts of glacial acetic acid and 300 parts of water and a homogeneous suspension suspension results. The mixture is atomised and a blue granulate results having good handle properties and little dust. Paper can be dyed a blue tone by adding the granulate to a paper mass.

In a similar fashion a granulate may be made from any one of compounds of Examples 1 to 299 and 302 to 350.

EXAMPLE 354

In 600 parts of water 22.2 parts (0.05 mols) of a compound of the formula 354a

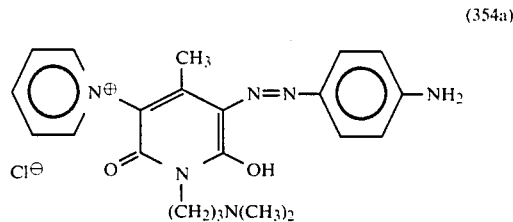

in hydrochloric acid medium are diazotised with 3.45 parts (0.05 mols) of sodium nitrite at 0°–5°. To this solution 15.9 parts (0.05 mols) of 1 amino-8-hydroxynaphthalene-3,6 disulphonic acid are added dropwise, dissolved in 150 parts of water and 3 parts of sodium carbonate. The solution has a pH of 1.5. By the addition of 10 parts of sodium acetate over 12 hours the pH is brought to 2.3. The resulting dyestuff is of formula 354b

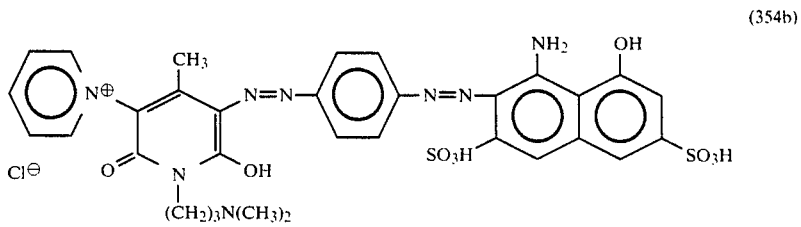

22 Parts (0.05 mols) of 2,4 bis-(diethylaminopropylamino)-6-(3'-aminophenylamino)-s-triazine in hydrochloric acid medium are diazotised in aqueous medium with 3.45 parts (0.05 mols) of sodium nitrite at 0°–5° and are then added to the compound of formula 354b in acid medium.

By the addition of 45 parts of a 30% aqueous NaOH solution the pH is brought to 8.5–9. After coupling has finished a dyestuff of the formula 354c these Examples the symbols $A_{33-42}$ are as defined below.

$A_{33}$ is $-(CH_2)_3N(CH_3)_2$ $A_{34}$ is $-(CH_2)_2NH_2$

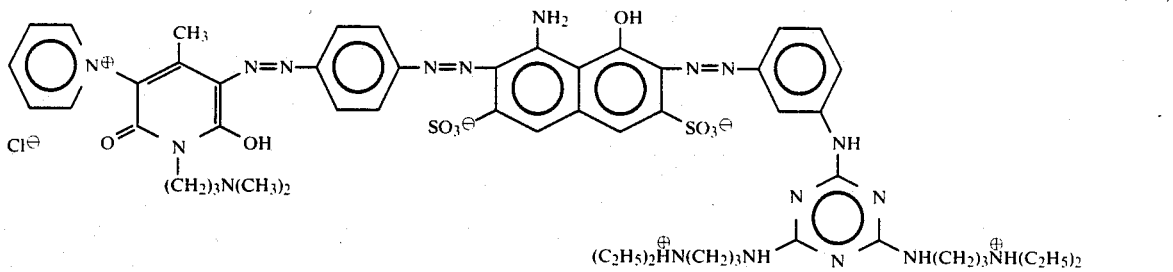

(354c)

is obtained. This compound 354c dyes paper and leather a black tone.

EXAMPLE 355

22 Parts (0.05 mols) of 2,4-bis(diethylaminopropylamino)-6-(3'-aminophenylamino)-3-triazine in hydrochloric acid medium are diazotised in aqueous medium with 3.45 parts (0.05 mols) of sodium nitrite at 0°–5°. This is then added in acid medium to 1-amino-8-hydroxynaphthalene 3,6-disulphonic acid and then 22.2 parts of the compound of formula 354a (from Example 354) are added in alkali medium to produce the compound of formula 355a

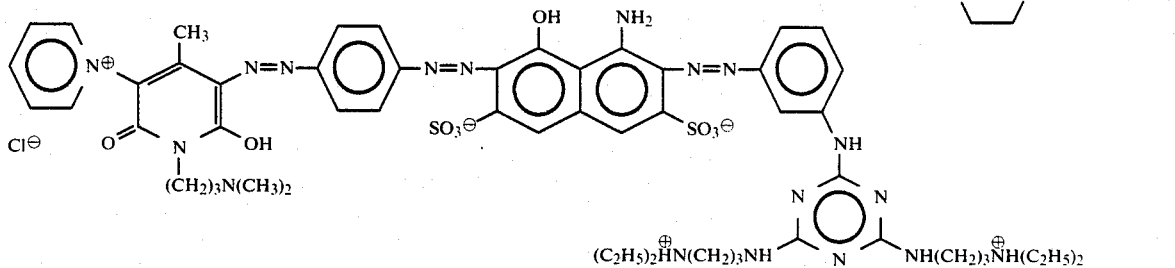

(355a)

This is an isomeric form of the compound 354c and also dyes paper and leather a black tone.

Both dyes 354c and 355a have good fastness properties.

EXAMPLES 356–380

Compounds of the formula $A_{37}$ is $-(CH_2)_2NHCOCH_2-N\underset{\underset{}{\diagdown\!\!\diagup}}{\diagup\!\!\diagdown}N-CH_3$

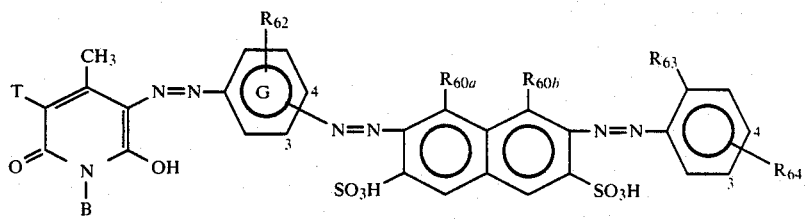

in which the symbols are defined in Table 16 can be formed by a method analogous to that of Example 354 or Example 355 from appropriate starting materials. In -continued

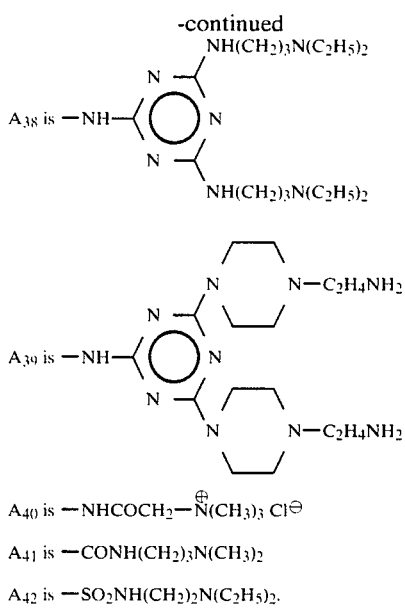

$A_{40}$ is $-NHCOCH_2-\overset{\oplus}{N}(CH_3)_3$ $Cl^{\ominus}$ $A_{41}$ is $-CONH(CH_2)_3N(CH_3)_2$ $A_{42}$ is $-SO_2NH(CH_2)_2N(C_2H_5)_2$.

TABLE 1b

| Ex. No. | T | B | Positions and significance of $R_{62}$ | Position of $-N=N$ on ring G | $R_{60a}$ | $R_{60b}$ | $R_{63}$ | Position and significance of $R_{64}$ |
|---|---|---|---|---|---|---|---|---|
| 356 | $T_4$ | $A_{33}$ | H | 4 | OH | $NH_2$ | H | 4-$A_{38}$ |
| 357 | $T_4$ | " | H | 4 | $NH_2$ | OH | H | 4-$A_{38}$ |
| 358 | $T_4$ | " | H | 3 | OH | $NH_2$ | H | 3-$A_{38}$ |
| 359 | $T_4$ | " | H | 3 | $NH_2$ | OH | H | 3-$A_{38}$ |
| 360 | $T_4$ | " | H | 3 | OH | $NH_2$ | H | 4-$A_{38}$ |
| 361 | $T_4$ | " | H | 3 | $NH_2$ | OH | H | 4-$A_{38}$ |
| 362 | $T_2$ | $A_{35}$ | H | 4 | OH | $NH_2$ | H | 3-$A_{38}$ |
| 363 | $T_5$ | " | H | 4 | OH | $NH_2$ | H | 3-$A_{38}$ |
| 364 | $T_4$ | $A_{34}$ | H | 4 | OH | $NH_2$ | H | 3-$A_{38}$ |
| 365 | $T_4$ | $A_{35}$ | H | 4 | OH | $NH_2$ | H | 3-$A_{38}$ |
| 366 | $T_4$ | $A_{36}$ | H | 4 | OH | $NH_2$ | H | 3-$A_{38}$ |
| 367 | $T_4$ | $A_{37}$ | H | 4 | OH | $NH_2$ | H | 3-$A_{38}$ |
| 368 | $T_4$ | $A_{35}$ | H | 4 | OH | $NH_2$ | H | 3-$A_{39}$ |
| 369 | $T_4$ | " | H | 4 | OH | $NH_2$ | H | 3-$A_{40}$ |
| 370 | $T_4$ | " | H | 4 | OH | $NH_2$ | H | 3-$A_{41}$ |
| 371 | $T_4$ | " | H | 4 | OH | $NH_2$ | H | 3-$A_{42}$ |
| 372 | $T_4$ | $A_{33}$ | OH(4) | 3 | OH | $NH_2$ | H | 3-$A_{38}$ |
| 373 | $T_4$ | " | OH(4) | 3 | OH | $NH_2$ | H | 3-$A_{38}$ |
| 374 | $T_4$ | " | OH(3) | 4 | OH | $NH_2$ | H | 3-$A_{38}$ |
| 375 | $T_4$ | " | OH(3) | 4 | OH | $NH_2$ | H | 3-$A_{38}$ |
| 376 | $T_4$ | $A_{35}$ | H | 4 | $NH_2$ | OH | OH | 3-$A_{42}$ |
| 377 | $T_4$ | " | H | 4 | $NH_2$ | OH | OH | 3-$A_{42}$ |
| 378 | $T_4$ | " | H | 4 | $NH_2$ | OH | $OCH_3$ | 3-$A_{42}$ |

APPLICATION EXAMPLE A

70 Parts of chemically bleached sulphite cellulose obtained from pinewood and 30 parts of chemically bleached sulphite cellulose obtained from birchwood are ground in 2000 parts of water in a Hollander. 0.5 Parts of the dyestuff from Example 301 of formula 301c (as an acid addition salt, e.g. Example 351) are sprinkled into this pulp. Paper is produced from this pulp after mixing for 20 minutes. The absorbent paper which is obtained in this manner is dyed in a blue tone. The waste water is practically colourless.

APPLICATION EXAMPLE B 0.5 Parts of the dyestuff from Example 301 of formula 301c (as an acid addition salt, e.g. Example 351) are added to 100 parts of chemically bleached sulphite cellulose which have been ground in a Hollander with 200 parts of water. Sizing takes place after thorough mixing for 15 minutes. The paper which is produced from this material has a blue tone and good light- and wet-fastnesses.

APPLICATION EXAMPLE C

An absorbent length of unsized paper is drawn at 40 to 50° C. through a dyestuff solution having the following composition:

0.5 parts of the dyestuff from Example 314 (as an acid addition salt)
0.5 parts of starch and
99.0 parts of water.

The excess dyestuff solution is squeezed out through two rollers. The dried length of paper is dyed in an orange tone.

APPLICATION EXAMPLE D

100 Parts freshly tanned and neutralised chrome leather are agitated for 30 minutes in a vessel with a dyebath of 250 parts water at 55° C. and 0.5 parts of the dyestuff of Examples 346 in acid addition salt form, and then treated in the same bath for 30 minutes with 2 parts of an anionic fatty liquor based on sulphonated train oil. The leather is then dried and prepared in the normal way, giving a leather evenly dyed in a black tone.

Other low affinity vegetable-tanned leathers can similarly be dyed by known methods.

APPLICATION EXAMPLE E

2 Parts of the dyestuff of Example 350 in acid addition salt form are dissolved in 4000 parts demineralised water at 40° C. 100 Parts of a pre-wetted cotton textile substrate are added, and the bath is raised to boiling point over 30 minutes and held at the boil for 1 hour. After rinsing and drying, a greyish-blue dyeing is obtained having good light- and wet-fastnesses. The dye exhausts practically totally, and the waste water is almost colourless.

The dyestuffs of any of the other Examples may be used in place of the compound of the particular Example named in any one of Application Examples A to C (if Examples 301 to 353 then in acid addition salt form).

The dyes so used may be in the form of solid or liquid preparations.

What is claimed is:

1. A metal-free compound of the formula

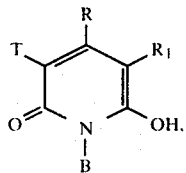
(1)

or a 1:1 or 1:2 metal complex thereof, or an acid addition salt of a metal-free compound of said formula or a 1:1 or 1:2 metal complex thereof, wherein B is hydrogen; $C_{1-4}$alkyl; $C_{1-4}$alkyl monosubstituted by $C_{1-4}$alkoxy; $C_{2-4}$alkyl substituted by hydroxy; $C_{5-6}$cycloalkyl; $C_{5-6}$cycloalkyl substituted by 1 to 3 $C_{1-4}$alkyl groups; phenyl($C_{1-3}$alkyl); phenyl($C_{1-3}$alkyl) the phenyl group of which is substituted by 1 to 3 substituents selected from $C_{1-4}$alkyl, $C_{1-4}$alkoxy and halo; —A—NH—$R_2$; —$A_4'$—N($R_7$)$_2$; —$A_4$—N$^\oplus$($R_8$)$_2R_9A^\ominus$ or —N($R_7$)$_2$, wherein A is linear or branched $C_{2-8}$alkylene; linear or branched $C_{2-8}$alkylene interrupted by 1 or 2 hetero atoms; linear or branched $C_{2-8}$alkenylene; linear or branched $C_{2-8}$alkenylene interrupted by 1 or 2 hetero atoms; phenylene or cyclohexylene, $A_4$ is linear or branched $C_{2-8}$alkylene or linear or branched $C_{2-8}$alkenylene, $A_4'$ is linear or branched $C_{1-8}$alkylene or linear or branched $C_{2-8}$alkenylene, and $R_2$ is

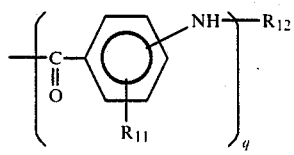

wherein $R_{11}$ is hydrogen, halo, nitro, $C_{1-4}$alkyl or $C_{1-4}$alkoxy, and $R_{12}$ is —CO—(CH$_2$)$_a$—Z or

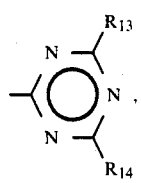

wherein Z is —N($R_7$)$_2$ or —N$^\oplus$($R_8$)$_2R_9A^\ominus$, and a is 1, 2 or 3, R is hydrogen; $C_{1-4}$alkyl; $C_{5-6}$cycloalkyl; $C_{5-6}$cycloalkyl substituted by 1 or 2 $C_{1-4}$alkyl groups; phenyl; phenyl substituted by 1 or 2 substituents selected from methyl, ethyl, methoxy and ethoxy; benzyl; phenylethyl; or benzyl or phenylethyl the phenyl group of which is substituted by 1 or 2 substituents selected from methyl, ethyl, methoxy and ethoxy, $R_1$ is hydrogen or —N=N—D, wherein D is a diazo component radical, with the proviso that $R_1$ must be

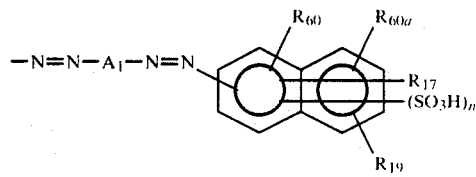

when B is other than —A—NH—$R_2$, wherein $A_1$ is a tetrazo component radical, $R_{17}$ is hydrogen, —N=N—$K_1$, —N=N—$A_1$-o—N=N—$K_1$,

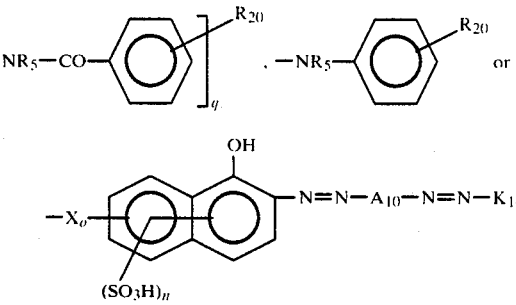

wherein $A_{10}$ is a tetrazo component radical or a coupling-/diazo component radical, $K_1$ is a diazo component radical or a coupling component radical, $R_{20}$ is —(NR$_5$)$_q$—Q$_1$—N($R_7$)$_2$, —(NR$_5$)$_q$—Q$_2$—N$^\oplus$($R_8$)$_2R_9A^\ominus$ or

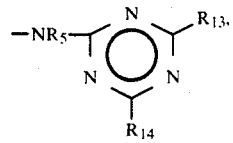

wherein $Q_1$ is linear or branched $C_{2-6}$alkylene, —CH$_2$-C*O— or —CH$_2$—CON*H—, wherein the * denotes the atom attached to the —(NR$_5$-)$_q$— radical, and $Q_2$ is linear or branched $C_{2-6}$alkylene, —CH$_2$-C*O—, —CH$_2$CON*H— or —CH$_2$CONH-C*O—, wherein the * denotes the atom attached to the —(NR$_5$)$_q$— radical, $X_o$ is a bridging radical, $R_{19}$ is hydrogen; hydroxy; amino; ($C_{1-4}$alkyl)carbonylamino; benzoylamino; phenylamino; or benzoylamino or phenylamino the phenyl group of which is substituted by 1 or 2 substituents selected from halo, nitro, amino, $C_{1-4}$alkyl and $C_{1-4}$alkoxy, with the proviso that $R_{19}$ must be hydrogen when $R_{17}$ is other than —N=N—$K_1$ and —N=N—$A_{10}$—N=N—$K_1$, and $R_{60}$ is hydroxy or amino, and $R_{60a}$ is hydrogen, hydroxy or amino, with the proviso that $R_{60a}$ is hydrogen or amino when $R_{60}$ is hydroxy and is hydroxy when $R_{60}$ is amino, and T is hydrogen, cyano, —COOR$_4$, —CO—N(R$_5$)$_2$, —SO$_2$—N(R$_5$)$_2$,

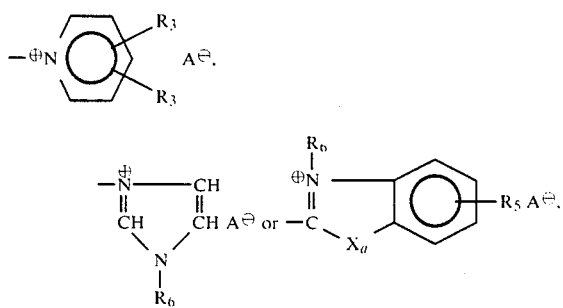

wherein
each R$_3$ is independently hydrogen, C$_{1-4}$alkyl, —N(R$_5$)$_2$ or —CO—N(R$_5$)$_2$,
R$_4$ is C$_{1-6}$alkyl or phenyl(C$_{1-3}$alkyl),
R$_6$ is C$_{1-4}$alkyl, and
X$_a$ is —O—, —NR$_5$— or —S—,
wherein
each R$_5$ is independently hydrogen or C$_{1-4}$alkyl or, when two R$_5$'s are attached to a nitrogen atom, both R$_5$'s taken together and with the nitrogen atom may form a saturated ring containing 1 to 3 hetero atoms,
each R$_7$ is independently hydrogen; C$_{1-6}$alkyl; C$_{2-6}$alkyl monosubstituted by halo, hydroxy or cyano; phenyl(C$_{1-3}$alkyl); phenyl(C$_{1-3}$alkyl) the phenyl group of which is substituted by 1 to 3 substituents selected from halo, C$_{1-4}$alkyl and C$_{1-4}$alkoxy; C$_{5-6}$cycloalkyl or C$_{5-6}$cycloalkyl substituted by 1 or 3 C$_{1-4}$alkyl groups, or both R$_7$'s taken together and with the nitrogen atom to which they are attached form a 5- or 6-membered saturated ring containing 1 to 3 hetero atoms,
each R$_8$ is independently C$_{1-6}$alkyl; C$_{2-6}$alkyl monosubstituted by halo, hydroxy or cyano; phenyl(C$_{1-3}$alkyl); phenyl(C$_{1-3}$alkyl) the phenyl group of which is substituted by 1 to 3 substituents selected from halo, C$_{1-4}$alkyl and C$_{1-4}$alkoxy; C$_{5-6}$cycloalkyl or C$_{5-6}$cycloalkyl substituted by 1 or 3 C$_{1-4}$alkyl groups,
each R$_9$ is independently C$_{1-4}$alkyl or C$_{1-4}$alkyl substituted by phenyl or both R$_8$'s and R$_9$ taken together and with the nitrogen atom to which they are attached are pyridinium; pyridinium substituted by 1 or 2 C$_{1-4}$alkyl groups; or a 5- or 6-membered saturated ring containing 1 to 3 hetero atoms,
each R$_{13}$ is independently amino; an aliphatic, cycloaliphatic, aromatic or heterocyclic amino group the nitrogen atom of which is attached to the 1,3,5-triazine ring; halo; hydroxy; C$_{1-4}$alkoxy; phenyl or

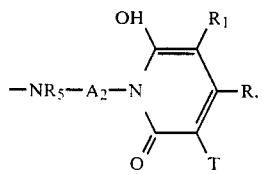

wherein
A$_2$ is linear or branched C$_{2-6}$alkylene or —N*H-COCH$_2$—, wherein the * denotes the atom attached to the —NR$_5$— radical, and R, R$_1$, R$_5$ and T are as defined above,
each R$_{14}$ is independently an aliphatic, cycloaliphatic, aromatic or heterocyclic amino group the nitrogen atom of which is attached to the 1,3,5-triazine ring,
each n is independently 0, 1 or 2,
each q is independently 0 or 1, and
each A$^\ominus$ is independently a non-chromophoric anion, with the provisos that (i) when the compound of Formula I is a monoazo compound free of sulfo groups, it contains at least one water-solubilizing basic or cationic group, (ii) when the compound of Formula I is free of sulfo groups and is other than a monoazo compound, it contains at least two water-solubilizing groups, and (iii) when the compound of Formula I contains one or more sulfo groups, the total number of basic and cationic groups exceeds the number of sulfo groups by at least one.

2. A compound according to claim 1 having the formula

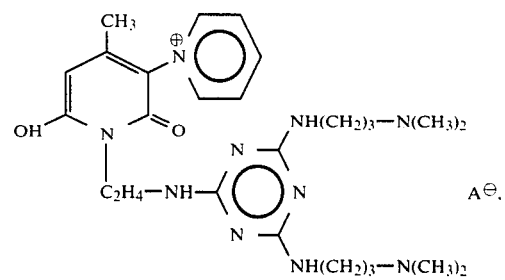

wherein A$^\ominus$ is a non-chromophoric anion.

3. A metal-free compound, 1:1 or 1:2 metal complex or acid addition salt according to claim 1 wherein T is hydrogen, cyano, —CO—N(R$_5'$)$_2$ or

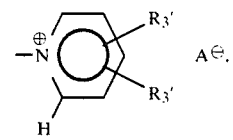

wherein
each R$_3'$ is independently hydrogen, methyl, ethyl, amino or dimethylamino, and
each R$_5'$ is independently hydrogen, methyl or ethyl.

4. A metal-free compound, 1:1 or 1:2 metal complex or acid addition salt according to claim 1 wherein
B is hydrogen, methyl, ethyl, hydroxyethyl, cyclohexyl, benzyl, —(CH$_2$)$_a$—N(R$_7'$)$_2$, —(CH$_2$)$_b$—N$^\oplus$(R$_8'$)$_2$R$_9'$A$^\ominus$ or —A'—NH—R$_2'$,
wherein
A' is linear or branched C$_{2-8}$alkylene or phenylene,
R$_2'$ is

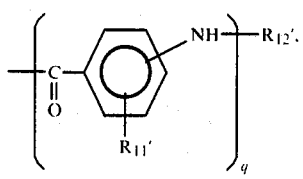

wherein
R₁₁' is hydrogen, chloro, nitro, methyl or methoxy,
R₁₂' is —CO—(CH₂)ₜ—Z' or

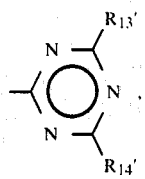

wherein
R₁₃' is chloro, hydroxy, amino, N,N-di-(C₂₋₄hydroxyalkyl)amino, —NR₅'R₂₁,

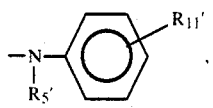

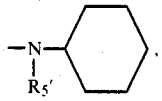

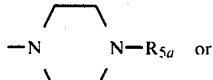

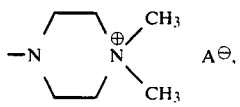

wherein R₁₁' is as defined above,
R₁₄' is —NR₅'R₂₁,

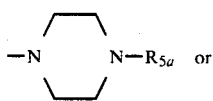

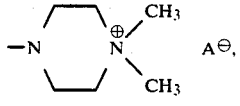

Z' is —N(R₇')₂ or —N⊕(R₈')₂R₉'A⊖, wherein R₇', R₈' and R₉' are as defined below, and
t is 1 or 2, and
q is 0 or 1,
each R₇' is independently hydrogen, C₁₋₆alkyl, n-hydroxy(C₂₋₃alkyl), benzyl or 2-cyanoethyl or
—N(R₇')₂ is pyrrolidino, piperidino, morpholino, piperazino or N'-methylpiperazino, each R₈' is independently C₁₋₆alkyl, n-hydroxy(C₂₋₃alkyl), benzyl or 2-cyanoethyl, and
R₉' is methyl, ethyl, propyl or benzyl or
—N⊕(R₈')₂R₉' is pyridinium, pyridinium substituted by 1 or 2 methyl groups or

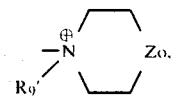

wherein
Z₀ is a direct bond, —CH₂—, —O—, —S—, —SO—, —SO₂—, —NH—, —NR₆— or —N⊕(R₆)₂—A⊖, and
R₉' is as defined above,
a is 1, 2 or 3, and
b is 2 or 3,
wherein
R₅' is hydrogen, methyl or ethyl, and
R₂₁ is C₁₋₁₂alkyl; C₂₋₁₂alkyl substituted by hydroxy; C₃₋₁₂alkyl interrupted by 1 to 3 radicals selected from —NR₇— and —N⊕(R₈)₂—A⊖; —NH-CO—CH₂—Z; —CH₂—CONH—Y₁—Z; —Y₁—Z;

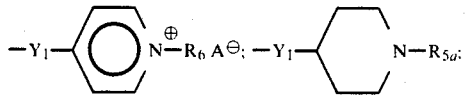

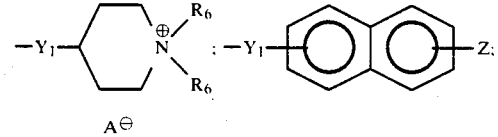

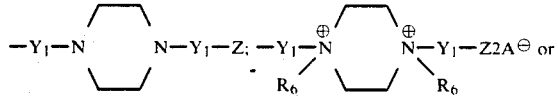

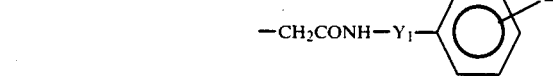

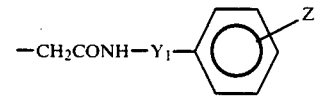

—CH₂CONH—Y₁—⌬—Z wherein
R₂₃ is halo, hydroxy, nitro, C₁₋₄alkyl or C₁₋₄alkoxy,
R₂₄ is —N(R₇')₂, —N⊕(R₈')₂R₉'A⊖, —CO—Y₂—Z', —NHCO—Y₂—Z', —CONH—Y₂—Z'—SO₂NH—Y₂—Z', —Y₂—Z' or —NHNH-CO—CH₂—Z',
wherein
Y₂ is linear or branched C₁₋₈alkylene, and
R₇', R₈', R₉' and Z' are as defined above,
each Y₁ is independently linear or branched C₁₋₈alkylene or linear or branched C₃₋₈alkenylene,
Z' is as defined above, and
R₇, R₈ and Z are as defined in claim 1, wherein
each $R_{5a}$ is independently hydrogen or $C_{1-4}$alkyl,
each $R_6$ is independently $C_{1-4}$alkyl, and
each $A^\ominus$ is independently a non-chromophoric anion.

5. A metal-free compound, 1:1 or 1:2 metal complex or acid addition salt according to claim 1 wherein R is methyl, ethyl, phenyl, benzyl or cyclohexyl.

6. A metal-free compound according to claim 1 having the formula

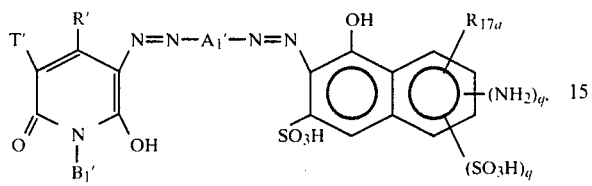

or a 1:1 or 1:2 metal complex thereof,
or an acid addition salt of a metal-free compound of said formula
or a 1:1 or 1:2 metal complex thereof,
wherein $A_1'$ is

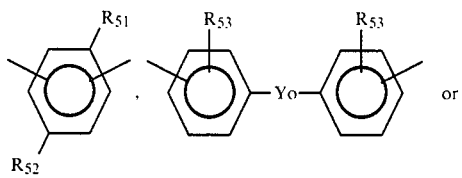

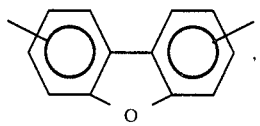

wherein
$R_{51}$ is hydrogen, halo, $C_{1-4}$alkyl or $C_{1-4}$alkoxy,
$R_{52}$ is hydrogen, hydroxy, halo, cyano, —CONH$_2$, ($C_{1-4}$alkyl)carbonylamino, —NHCONH$_2$, carboxy, sulfo, $C_{1-4}$alkyl or $C_{1-4}$alkoxy,
each $R_{53}$ is independently hydrogen, halo, cyano, $C_{1-4}$alkyl, $C_{1-4}$alkoxy, carboxy, sulfo or hydroxy, and
$Y_o$ is a direct bond, —(CH$_2$)$_a$—, —O—, —S—, —SO$_2$—, —NHCO—, —NHCONH—, —NH-CO—(CH$_2$)$_b$—CONH—, —CONH—(CH$_2$)$_b$—NHCO—, —O—(CH$_2$)$_b$—O—, —N=N— or —CH=CH—CO—CH=CH—,
$B_1'$ is hydrogen, methyl, ethyl, hydroxyethyl, cyclohexyl, benzyl, —(CH$_2$)$_b$—N(R$_7''$)$_2$ or —(CH$_2$)$_b$—N$^\oplus$(R$_8''$)$_2$R$_9''$A$^\ominus$,
wherein
each $R_7''$ is independently hydrogen, methyl, ethyl or 2-hydroxyethyl or
—N(R$_7''$)$_2$ is morpholino, piperidino, piperazino or N'-methylpiperazino,
each $R_8''$ is independently methyl, ethyl or 2-hydroxyethyl, and $R_9''$ is methyl, ethyl or benzyl or
—N$^\oplus$(R$_8''$)$_2$R$_9''$ is pyridinium, pyridinium substituted by 1 or 2 methyl groups or

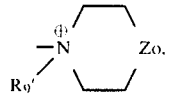

wherein $R_9'$ and $Z_o$ are as defined below,
R' is methyl, ethyl, phenyl, benzyl or cyclohexyl,
$R_{17a}$ is —N=N—K$_1'$, —N=N—A$_1'$—N=N—K$_1'$ or

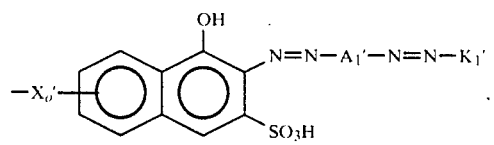

wherein K$_1'$ is

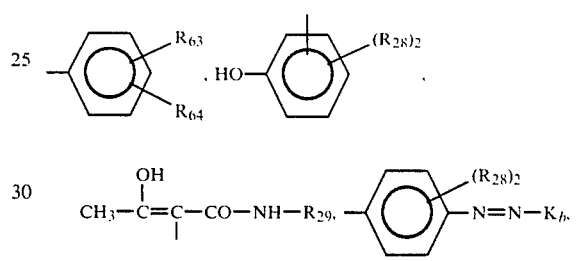

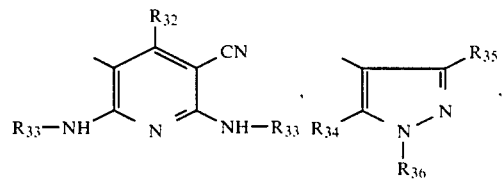

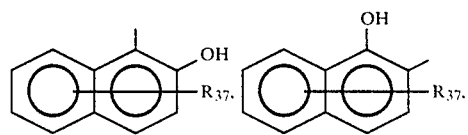

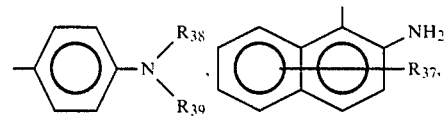

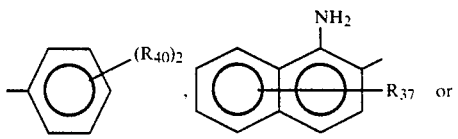

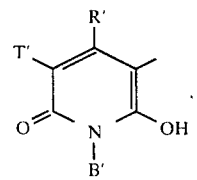

wherein K$_b$ is

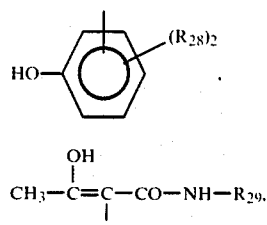

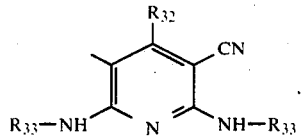

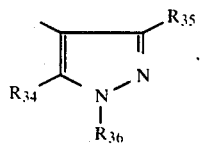

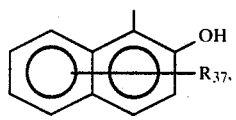

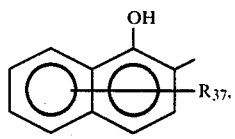

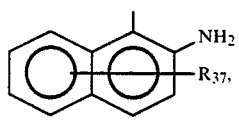

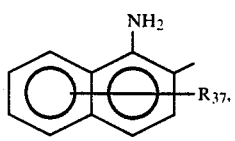

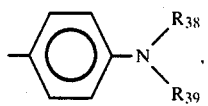

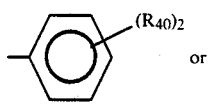

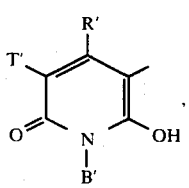

wherein
each $R_{28}$ is independently hydrogen, halo, $C_{1-4}$alkyl or $C_{1-4}$alkoxy,
$R_{29}$ is —(CH$_2$)$_m$—Z,

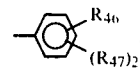

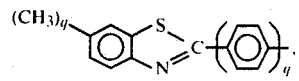

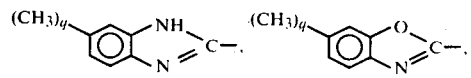

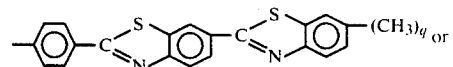

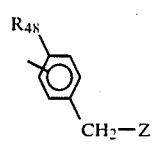

wherein
$R_{46}$ is hydrogen, —NHCO—(CH$_2$)$_b$—Z, —SO$_2$NH—(CH$_2$)$_b$—Z, —CO—Y$_1$—Z or

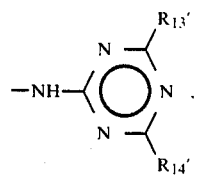

each $R_{47}$ is independently hydrogen, halo, $C_{1-4}$alkyl, $C_{1-4}$alkoxy, nitro or cyano, and
$R_{48}$ is $C_{1-4}$alkoxy,
$R_{32}$ is $C_{1-4}$alkyl or phenyl,
each $R_{33}$ is independently hydrogen, $C_{1-4}$alkyl, —(CH$_2$)$_b$—OCH$_3$, 2-hydroxyethyl, —(CH$_2$)$_b$—N(CH$_3$)$_2$ or —(CH$_2$)$_b$—N$^\oplus$(CH$_3$)$_3$A$^\ominus$,
$R_{34}$ is amino or hydroxy,
$R_{35}$ is $C_{1-4}$alkyl, —COOR$_6$, —CO—N(R$_{5a}$)$_2$ or —CONH—Y$_1$—Z,
$R_{36}$ is hydrogen,

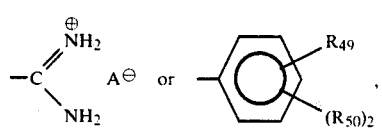

wherein
$R_{49}$ is hydrogen, —CONH—Y$_1$—Z, —SO$_2$NH—Y$_1$—Z, —NHCO—(CH$_2$)$_b$—Z or

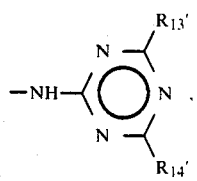

and
each $R_{50}$ is independently hydrogen, halo, $C_{1-4}$alkoxy, $C_{1-4}$alkyl, nitro or amino, $R_{37}$ is hydrogen, —NHCO—$(CH_2)_a$—Z, —$SO_2NH$—$Y_1$—Z, —CONH—$Y_1$—Z, —CONHNH$_2$, —NH—$Y_1$—Z, —$CH_2$—Z, —NHNHCO—$CH_2$—Z, nitrophenylcarbamoyl or

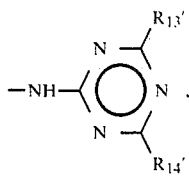

$R_{38}$ is $C_{1-4}$alkyl, benzyl or 2-cyanoethyl,
$R_{39}$ is $C_{1-4}$alkyl or —$(CH_2)_m$—Z,
each $R_{40}$ is independently hydrogen, $C_{1-4}$alkyl or $C_{1-4}$alkoxy,
$R_{63}$ is hydrogen, chloro, nitro, $C_{1-4}$alkyl, $C_{1-4}$alkoxy or hydroxy,
$R_{64}$ is hydrogen, dimethylamino, trimethylammonium A$^\ominus$, diethylamino, triethylammonium A$^\ominus$, —CO—$Y_2$—Z, —CONH—$Y_2$—Z, —$Y_2$—Z, —NHCO—$Y_2$—Z, —$SO_2NH$—$Y_2$—Z, —NHNHCO—$CH_2$—Z or

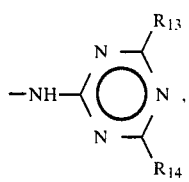

R' is as defined above, and
B' and T' are as defined below,
$X_o'$ is —NH—, —NHCONH—, —NH-CO—CH=CH—CONH—, —NH-CO—$(CH_2)_b$—CONH—,

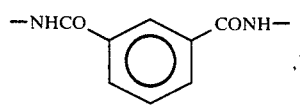

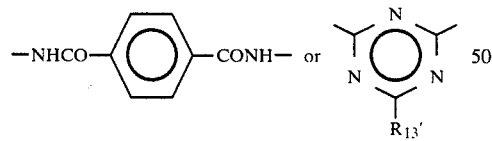

and
$A_1'$ is as defined above, and
T' is hydrogen, cyano, —CO—N$(R_5')_2$ or

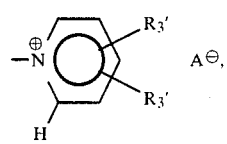

wherein
each $R_3'$ is independently hydrogen, methyl, ethyl, amino or dimethylamino, and each $R_5'$ is independently hydrogen, methyl or ethyl,
wherein
B' is hydrogen, methyl, ethyl, hydroxyethyl, cyclohexyl, benzyl, —$(CH_2)_a$—N$(R_7')_2$, —$(CH_2)_b$—N$^\oplus(R_8')_2R_9'$A$^\ominus$ or —A'—NH—$R_2'$,
wherein
A' is linear or branched $C_{2-8}$alkylene or phenylene,
$R_2'$ is

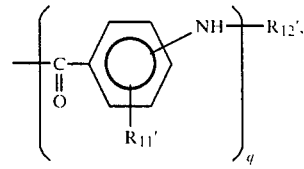

wherein
$R_{11}'$ is hydrogen, chloro, nitro, methyl or methoxy,
$R_{12}'$ is —CO—$(CH_2)_r$—Z' or

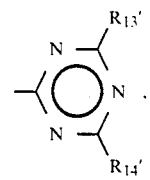

wherein
is chloro, hydroxy, amino, N,N-di-($C_{2-4}$-hydroxyalkyl)amino, —$NR_5'R_{21}$,

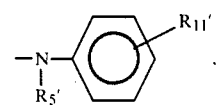

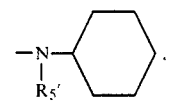

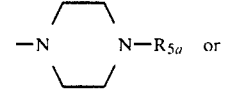

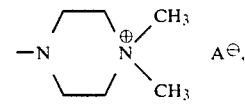

wherein $R_{11}'$ is as defined above,
$R_{14}'$ is —$NR_5'R_{21}$,

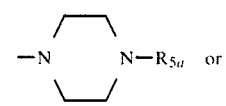

-continued

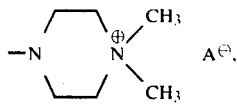

Z' is —N(R$_7$')$_2$ or —N$^⊕$(R$_8$')$_2$R$_9$'A$^⊖$, wherein R$_7$', R$_8$' and R$_9$' are as defined below, and t is 1 or 2, each R$_7$' is independently hydrogen, C$_{1-6}$alkyl, n-hydroxy(C$_{2-3}$alkyl), benzyl or 2-cyanoethyl or —N(R$_7$')$_2$ is pyrrolidino, piperidino, morpholino, piperazino or N'-methylpiperazino, each R$_8$' is independently C$_{1-6}$alkyl, n-hydroxy(C$_{2-3}$alkyl), benzyl or 2-cyanoethyl, and R$_9$' is methyl, ethyl, propyl or benzyl or —N$^⊕$(R$_8$')$_2$R$_9$' is pyridinium, pyridinium substituted by 1 or 2 methyl groups or

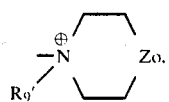

wherein
Z$_o$ is a direct bond, —CH$_2$—, —O—, —S—, —SO—, —SO$_2$—, —NH—, —NR$_6$— or —N$^⊕$(R$_6$)$_2$—A$^⊖$, and
R$_9$' is as defined above,
wherein
R$_5$' is hydrogen, methyl or ethyl, and
R$_{21}$ is C$_{1-12}$alkyl; C$_{2-12}$alkyl substituted by hydroxy; C$_{3-12}$alkyl interrupted by 1 to 3 radicals selected from —NR$_7$— and —N$^⊕$(R$_8$)$_2$—A$^⊖$; —NH—CO—CH$_2$—Z; —CH$_2$—CONH—Y$_1$—Z; —Y$_1$—Z;

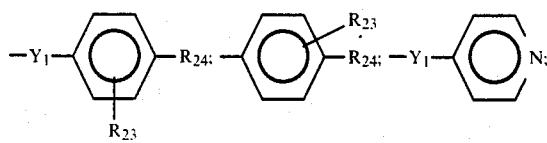

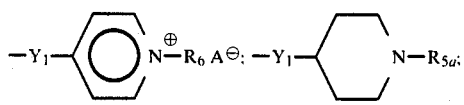

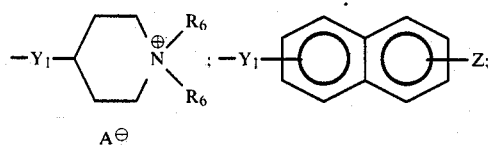

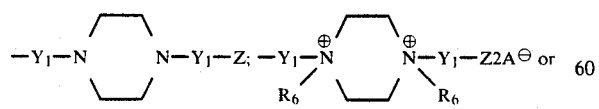

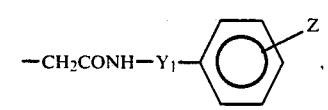

wherein

R$_{23}$ is halo, hydroxy, nitro, C$_{1-4}$alkyl or C$_{1-4}$alkoxy,

R$_{24}$ is —N(R$_7$')$_2$, —N$^⊕$(R$_8$')$_2$R$_9$'A$^⊖$, —CO—Y$_2$—Z', —NHCO—Y$_2$—Z', —CONH—Y$_2$—Z' —SO$_2$NH—Y$_2$—Z', —Y$_2$—Z' or —NHNH-CO—CH$_2$—Z', wherein R$_7$', R$_8$' and R$_9$' are as defined above,
wherein
each R$_{5a}$ is independently hydrogen or C$_{1-4}$alkyl,
each R$_6$ is independently C$_{1-4}$alkyl,
each R$_7$, R$_8$, R$_{13}$, R$_{14}$ and Z is independently as defined in claim 1,
each R$_{13}$', R$_{14}$' and Z' is independently as defined above,
each Y$_1$ is independently linear or branched C$_{1-8}$alkylene or linear or branched C$_{3-8}$alkenylene,
each Y$_2$ is independently linear or branched C$_{1-8}$alkylene,
each a is independently 1, 2 or 3,
each b is independently 2 or 3,
each m is independently 1, 2, 3, 4, 5 or 6,
each q is independently 0 or 1, and
each A$^⊖$ is independently a non-chromophoric anion.

7. A metal-free compound according to claim 1 having the formula

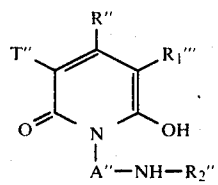

or a 1:1 or 1:2 metal complex thereof, or an acid addition salt of a metal-free compound of said formula or a 1:1 or 1:2 metal complex thereof,
wherein
A" is 1,2-ethylene, 1,3-propylene, 1,3-phenylene or 1,4-phenylene,
R" is methyl or phenyl,
R$_1$'" is hydrogen or —N=N—D",
wherein
D" is

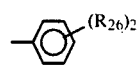

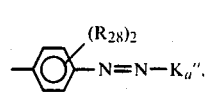

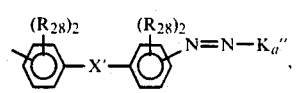

wherein
K$_a$" is

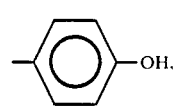

-continued
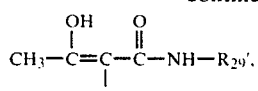
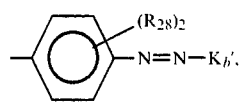
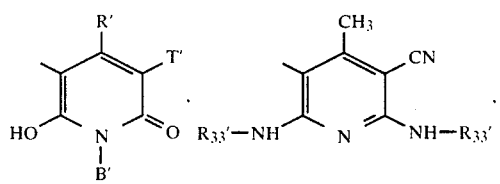
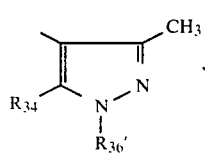
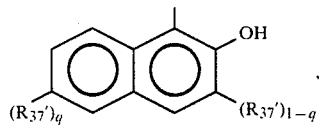
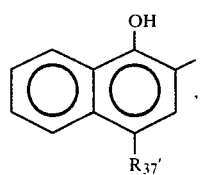
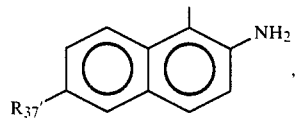
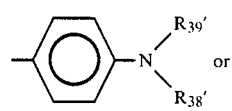
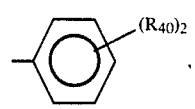
$R_{17}'$ is hydrogen,
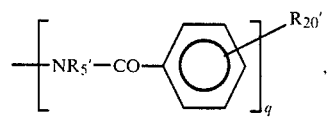
$-N=N-K_1'$, $-N=N-A_1'-N=N-K_1'$ or
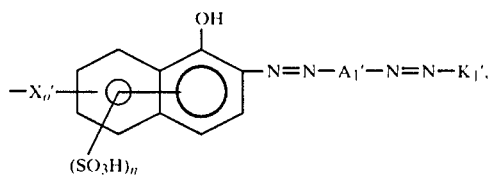
wherein
$R_{20}'$ is $-NR_5'-Q_1-N(R_7')_2$, $-NR_5'-Q_2-N^{\oplus}(R_8')_2R_9'A^{\ominus}$ or
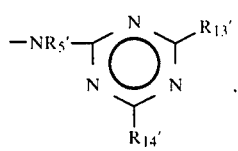
$R_2''$ is
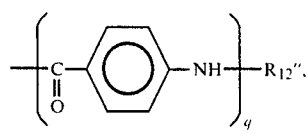
wherein
$R_{12}''$ is $-CO-CH_2-Z''$ or
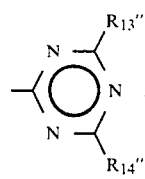
wherein
$R_{13}''$ is $-NR_5''R_{21}''$,
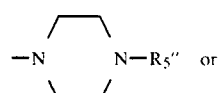
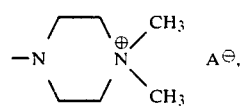
$R_{14}''$ is $-NR_5''R_{21}'$,
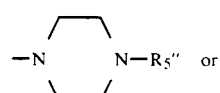
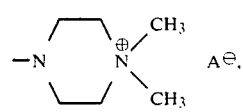
and
$Z''$ is $-N(R_7'')_2$ or $-N^{\oplus}(R_8'')_2R_9''A^{\ominus}$, and
$R''$ is cyano or

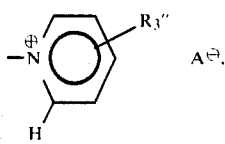

wherein
R$_3''$ is hydrogen or methyl,
wherein
each A$_1'$ is independently

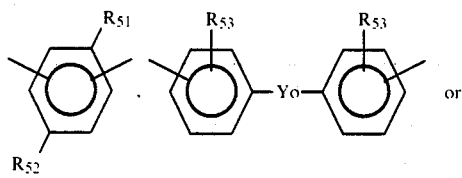

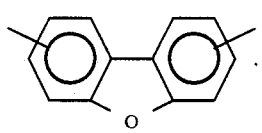

wherein
R$_{51}$ is hydrogen, halo, C$_{1-4}$alkyl or C$_{1-4}$alkoxy,
R$_{52}$ is hydrogen, hydroxy, halo, cyano, —CONH$_2$, (C$_{1-4}$alkyl)carbonylamino, —NHCONH$_2$, carboxy, sulfo, C$_{1-4}$alkyl or C$_{1-4}$alkoxy,
each R$_{53}$ is independently hydrogen, halo, cyano, C$_{1-4}$alkyl, C$_{1-4}$alkoxy, carboxy, sulfo or hydroxy, and
Y$_0$ is a direct bond, —(CH$_2$)$_a$—, —O—, —S—, —SO$_2$—, —NHCO—, —NHCONH—, —NHCO—(CH$_2$)$_b$—CONH—, —CONH—(CH$_2$)$_b$—NHCO—, —O—(CH$_2$)$_b$—O—, —N=N— or —CH=CH—CO—CH=CH—,
wherein
B' is hydrogen, methyl, ethyl, hydroxyethyl, cyclohexyl, benzyl, —(CH$_2$)$_a$—N(R$_7'$)$_2$, —(CH$_2$)$_b$—N$^\oplus$(R$_8'$)$_2$R$_9'$A$^\ominus$ or —A'—NH—R$_2'$,
wherein A' is linear or branched C$_{2-8}$alkylene or phenylene,
R$_2'$ is

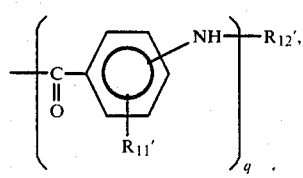

wherein
R$_{11}'$ is hydrogen, chloro, nitro, methyl or methoxy,
R$_{12}'$ is —CO—(CH$_2$)$_r$—Z' or

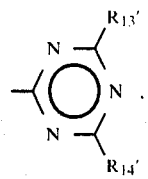

wherein
R$_{13}'$ is chloro, hydroxy, amino, N,N-di-(C$_{2-4}$-hydroxyalkyl)amino, —NR$_5'$R$_{21}$,

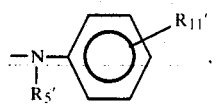

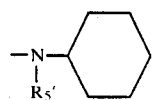

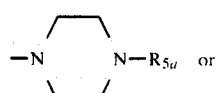

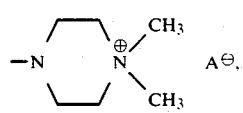

wherein R$_{11}'$ is as defined above,
R$_{14}'$ is —NR$_5'$R$_{21}$,

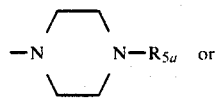

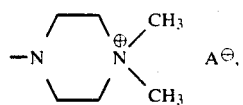

Z' is —N(R$_7'$)$_2$ or —N$^\oplus$(R$_8'$)$_2$R$_9'$A$^\ominus$, wherein R$_7'$, R$_8'$ and R$_9'$ are as defined below, and
t is 1 or 2,
wherein K$_1'$ is

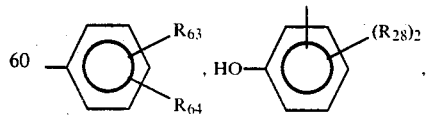

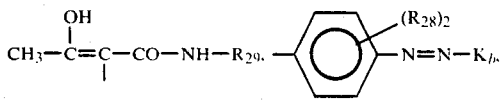

-continued
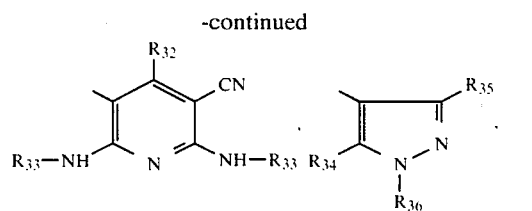
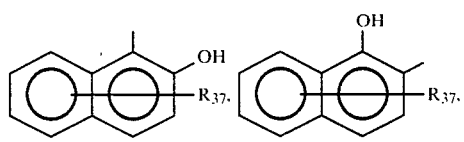
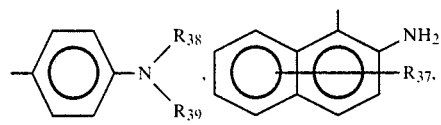
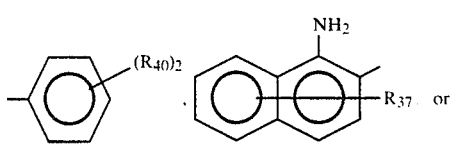
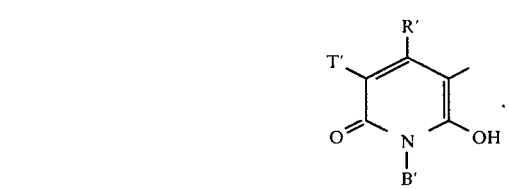 or
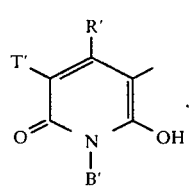
wherein $K_b$ is
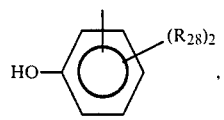
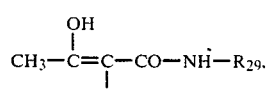
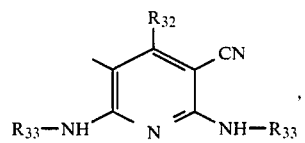
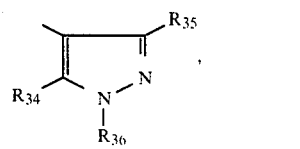
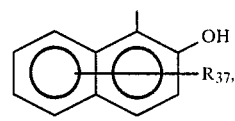
-continued
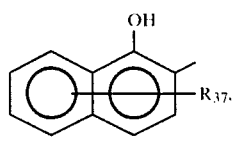
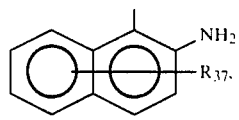
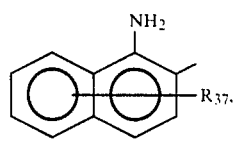
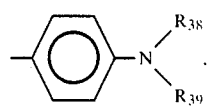
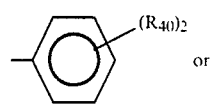 or
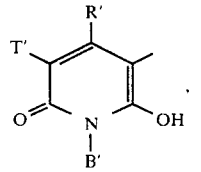
wherein $R_{29}$ is —(CH$_2$)$_m$—Z,
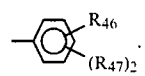
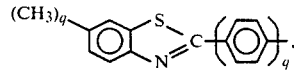
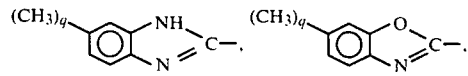
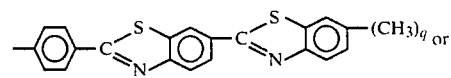 or
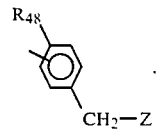
wherein
$R_{46}$ is hydrogen, —NHCO—(CH$_2$)$_b$—Z, —SO$_2$NH—(CH$_2$)$_b$—Z, —CO—Y$_1$—Z or

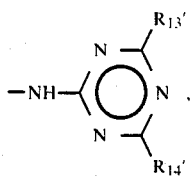

each $R_{47}$ is independently hydrogen, halo, $C_{1-4}$alkyl, $C_{1-4}$alkoxy, nitro or cyano, and
$R_{48}$ is $C_{1-4}$alkoxy,
$R_{32}$ is $C_{1-4}$alkyl or phenyl,
each $R_{33}$ is independently hydrogen, $C_{1-4}$alkyl, —(CH$_2$)$_b$—OCH$_3$, 2-hydroxyethyl, —(CH$_2$)$_b$—N(CH$_3$)$_2$ or —(CH$_2$)$_b$—N$^\oplus$(CH$_3$)$_3$A$^\ominus$,
$R_{34}$ is amino or hydroxy,
$R_{35}$ is $C_{1-4}$alkyl, —COOR$_6$, —CO—N(R$_{5a}$)$_2$ or —CONH—Y$_1$—Z,
$R_{36}$ is hydrogen,

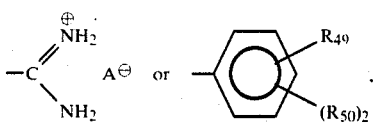

wherein
$R_{49}$ is hydrogen, —CONH—Y$_1$—Z, —SO$_2$NH—Y$_1$—Z, —NHCO—(CH$_2$)$_b$—Z or

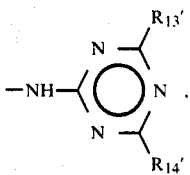

and
each $R_{50}$ is independently hydrogen, halo, $C_{1-4}$alkoxy, $C_{1-4}$alkyl, nitro or amino,
$R_{37}$ is hydrogen, —NHCO—(CH$_2$)$_a$—Z, —SO$_2$NH—Y$_1$—Z, —CONH—Y$_1$—Z, —CONHNH$_2$, —NH—Y$_1$—Z, —CH$_2$—Z, —NHNHCO—CH$_2$—Z, nitrophenylcarbamoyl or

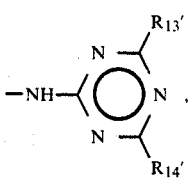

$R_{38}$ is $C_{1-4}$alkyl, benzyl or 2-cyanoethyl,
$R_{39}$ is $C_{1-4}$alkyl or —(CH$_2$)$_m$—Z,
each $R_{40}$ is independently hydrogen, $C_{1-4}$alkyl or $C_{1-4}$alkoxy,
$R_{63}$ is hydrogen, chloro, nitro, $C_{1-4}$alkyl, $C_{1-4}$alkoxy or hydroxy,
$R_{64}$ is hydrogen, dimethylamino, trimethylammonium A$^\ominus$, diethylamino, triethylammonium A$^\ominus$, —CO—Y$_2$—Z, —CONH—Y$_2$—Z, —Y$_2$—Z, —NHCO—Y$_2$—Z, —SO$_2$NH—Y$_2$—Z, —NHNHCO—CH$_2$—Z or

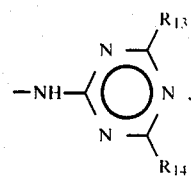

and
B' is as defined above,
$K_b'$ is

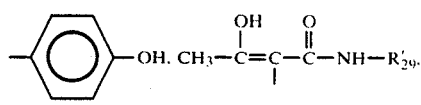

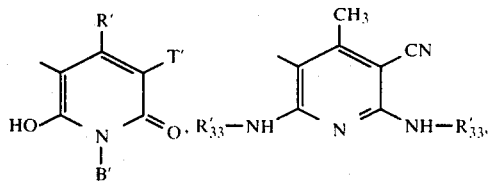

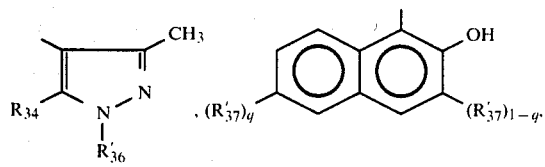

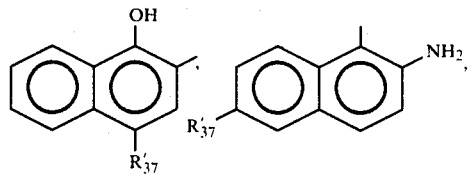

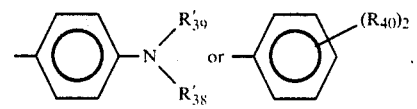

wherein B' is as defined above,
each R' is independently methyl, ethyl, phenyl, benzyl or cyclohexyl,
each $R_{5a}$ is independently hydrogen or $C_{1-4}$alkyl,
each $R_5'$ is independently hydrogen, methyl or ethyl,
each $R_5''$ is independently hydrogen or methyl,
each $R_6$ is independently $C_{1-4}$alkyl,
each $R_7'$ is independently hydrogen, $C_{1-6}$alkyl, n-hydroxy($C_{2-3}$alkyl), benzyl or 2-cyanoethyl or
—N($R_7'$)$_2$ is pyrrolidino, piperidino, morpholino, piperazino or N'-methylpiperazino,
each $R_7''$ is independently hydrogen, methyl, ethyl or 2-hydroxyethyl or
—N($R_7''$)$_2$ is morpholino, piperidino, piperazino or N'-methylpiperazino,
each $R_8'$ is independently $C_{1-6}$alkyl, n-hydroxy($C_{2-3}$alkyl), benzyl or 2-cyanoethyl, and
each $R_9'$ is independently methyl, ethyl, propyl or benzyl or —N$^\oplus$(R$_8'$)$_2$R$_9'$ is pyridinium, pyridinium substituted by 1 or 2 methyl groups or

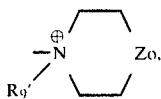

wherein

Zo is a direct bond, —CH$_2$—, —O—, —S—, —SO—, —SO$_2$—, —NH—, —NR$_6$— or —N$^⊕$(R$_6$)$_2$—A$^⊖$, wherein R$_6$ is as defined above, and R$'_9$ is as defined above, each R$_8''$ is independently methyl, ethyl or 2-hydroxyethyl, and each R$_9''$ is independently methyl, ethyl or benzyl or —N$^⊕$(R$_8''$)$_2$R$_9''$ is pyridinium, pyridinium substituted by 1 or 2 methyl groups or

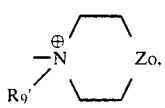

wherein R$_9'$ and Zo are as defined above,
each R$_{13}'$ and R$_{14}'$ is independently as defined above,
R$_{21}$ is C$_{1-12}$alkyl; C$_{2-12}$alkyl substituted by hydroxy; C$_{3-12}$alkyl interrupted by 1 to 3 radicals selected from —NR$_7$— and —N$^⊕$(R$_8$)$_2$—A$^⊖$; —NH-CO—CH$_2$—Z; —CH$_2$—CONH—Y$_1$—Z; —Y$_1$—Z;

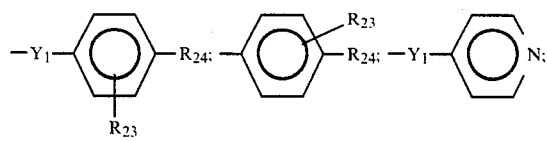

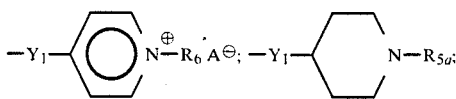

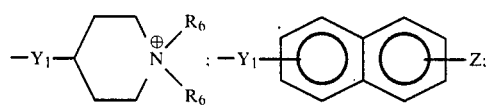

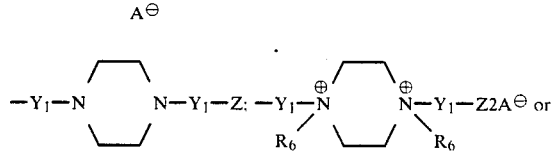

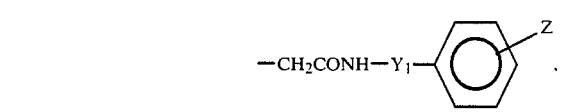

wherein

R$_{23}$ is halo, hydroxy, nitro, C$_{1-4}$alkyl or C$_{1-4}$alkoxy,

R$_{24}$ is —N(R$_7'$)$_2$, —N$^⊕$(R$_8'$)$_2$R$_9'$A$^⊖$, —CO—Y$_2$—Z', —NHCO—Y$_2$—Z', —CONH—Y$_2$—Z'—SO$_2$NH—Y$_2$—Z', —Y$_2$—Z' or —NHNH-CO—CH$_2$—Z', wherein R$_7'$, R$_8'$ and R$_9'$ are as defined above, and R$_{5a}$ and R$_6$ are as defined above, R$_{21}'$ is —(CH$_2$)$_b$—N(R$_7''$)—(CH$_2$)$_b$—NR$_7''$R$_6'$, —(CH$_2$)$_b$—N$^⊕$(R$_8''$)$_2$—(CH$_2$)$_b$13 N$^⊕$(R$_8''$)$_2$R$_6'$2A$^⊖$, —(CH$_2$)$_b$—N(R$_7''$)—C$_2$H$_5$, —(CH$_2$)$_b$—N$^⊖$(R$_8''$)$_2$—C$_2$H$_5$A$^⊖$, —NH-CO—CH$_2$—Z'', —CH$_2$—CONH—Y$_2''$Z'',

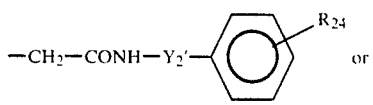

or

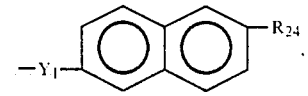

wherein

R$_6'$ is methyl or ethyl,

Y$_2'$ is linear or branched C$_{1-4}$alkylene, and

R$_7''$, R$_8''$, R$_{24}$ and Z'' are as defined above, each R$_{26}$ is independently hydrogen, halo, nitro, amino, C$_{1-4}$alkyl, C$_{1-4}$alkoxy, cyano, trifluoromethyl, phenyl, anilino, benzoyl, carbamoyl, phenoxy, halophenoxy, dihalophenoxy, C$_{1-4}$alkylsulfonyl, phenylsulfonyl, C$_{1-4}$alkylsulfonylamino or N,N-di(C$_{1-4}$alkyl)sulfamoyl, each R$_{28}$ is independently hydrogen, halo, C$_{1-4}$alkyl or C$_{1-4}$alkoxy, R$_{29}'$ is —(CH$_2$)$_{m'}$Z',

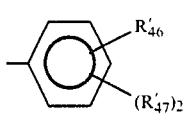

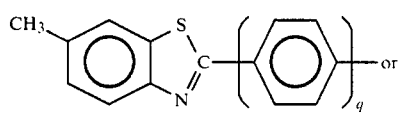

wherein

R$_{46}'$ is hydrogen, —NHCO—(CH$_2$)$_b$—Z', —SO$_2$NH—(CH$_2$)$_b$—Z' or

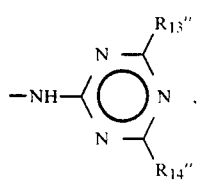

wherein R$_{13}''$ and R$_{14}''$ are as defined above, each R$_{47}'$ is independently hydrogen, chloro, bromo, methyl, ethyl, methoxy, ethoxy, nitro or cyano, and $R_{48'}$ is methoxy or ethoxy, and
each $R_{33'}$ is independently hydrogen, 2-hydroxyethyl, 3-methoxypropyl, —(CH$_2$)$_b$—N(CH$_3$)$_2$ or —(CH$_2$)$_b$—N$^{\oplus}$(CH$_3$)$_3$A$^{\ominus}$,
$R_{34}$ is hydroxy or amino,
$R_{36'}$ is hydrogen,

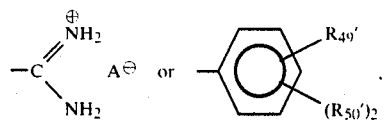

wherein $R_{49'}$ is hydrogen, —CONH—(CH$_2$)$_{m'}$—Z', —NHCO—(CH$_2$)$_b$—Z' or

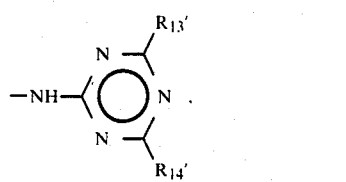

wherein $R_{13'}$ and $R_{14'}$ are as defined above, and each $R_{50'}$ is independently hydrogen, chloro, methyl or methoxy,
$R_{37'}$ is

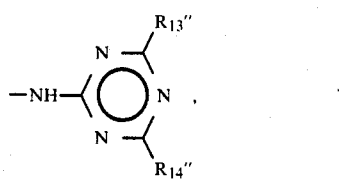

wherein $R_{13''}$ and $R_{14''}$ are as defined above,
$R_{38'}$ is methyl, ethyl, 2-cyanoethyl or benzyl,
$R_{39'}$ is methyl, ethyl or —(CH$_2$)$_{m'}$—Z,
$R_{40}$ is independently hydrogen, C$_{1-4}$alkyl or C$_{1-4}$alkoxy,
each T' is independently hydrogen, cyano, —CO—N(R$_5'$)$_2$ or

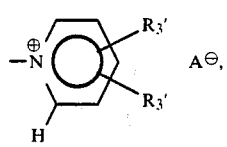

wherein
each $R_3'$ is independently hydrogen, methyl, ethyl, amino or dimethylamino, and
$R_5'$ is as defined above,
X' is —NH—CO—NH—,

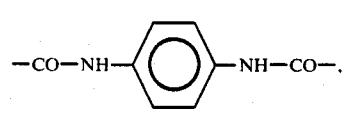

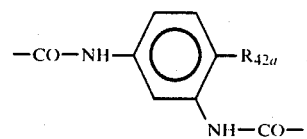

—NH—CO—CH$_2$—CH$_2$—CO—NH—,
—NH—CO—CH=CH—CO—NH—,
—NH—CO—(CH$_2$)$_4$—CO—NH—,

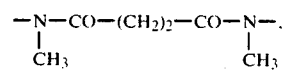

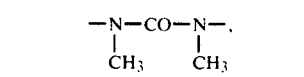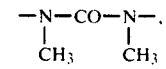

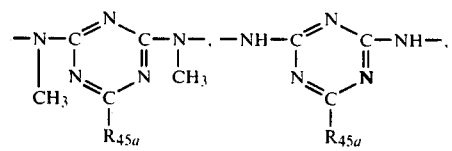

—CH$_2$—, —(CH$_2$)$_2$—, —(CH$_2$)$_3$—, —(CH$_2$)$_4$—,
—CO—NH—(CH$_2$)$_2$—NH—CO—,
—CO—NH—(CH$_2$)$_3$—NH—CO—,
—CO—NH—(CH$_2$)$_4$—NH—CO—,

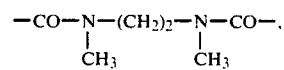

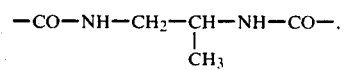

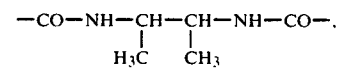

—CO—NH—R$_{43}$—CO—NH—R$_{43}$—NH—CO—,
—CO—NH—R$_{43}$NH—CO—CH$_2$—CH$_2$—CO—NH—R$_{43}$NH—CO—,
—CO—NH—R$_{43}$NH—CO—CH=CH—CO—NH—R$_{43}$NH—CO—,

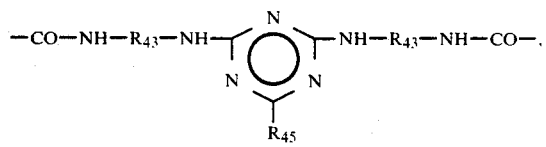

—SO$_2$—NR$_{44}$—(CH$_2$)$_g$—NH$_{44}$—SO$_2$—,
—CO—NR$_{44}$—R$_{43}$—O—CO—,

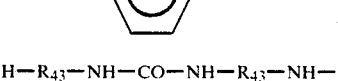 or

—CONH—R$_{43}$—NH—CO—NH—R$_{43}$—NH—CO—, wherein
$R_{42a}$ is hydrogen, chloro, methyl or methoxy, each $R_{43}$ is independently linear or branched $C_{1-4}$alkylene, each $R_{44}$ is independently hydrogen or $C_{1-4}$alkyl, $R_{45}$ is halo, 2-hydroxyethylamino, N,N-di-(2-hydroxyethyl)amino, amino, hydroxy, —NH—$(CH_2)_b$—$N(C_2H_5)_2$, N-methyl-N-phenylamino, N-cyclohexyl-N-methylamino, piperidino, methoxy or ethoxy, $R_{45a}$ is chloro, 2-hydroxyethylamino, methoxy, ethoxy, hydroxy, amino, N,N-di-(2-hydroxyethyl)amino, 3-diethylaminopropylamino, N-methyl-N-phenylamino, N-cyclohexyl-N-methylamino or piperidino, and g is 1, 2, 3 or 4, $X_o'$ is —NH—, —NHCONH—, —NHCO—CH=CH—CONH—, —NHCO—$(CH_2)_b$—CONH—,

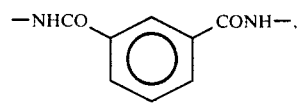

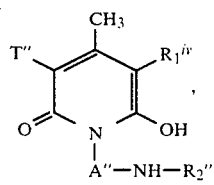

wherein $R_{13}'$ is as defined above, each $Y_1$ is independently linear or branched $C_{1-8}$alkylene or linear or branched $C_{3-8}$alkenylene, each $Y_2$ is independently linear or branched $C_{1-8}$alkylene, each $Z'$ is independently as defined above, each $Q_1$, $Q_2$, $R_7$, $R_8$, $R_{13}$, $R_{14}$ and Z is independently as defined in claim 1, each a is independently 1, 2 or 3, each b is independently 2 or 3, each m is independently 1, 2, 3, 4, 5 or 6, each m' is independently 2, 3 or 4, each n is independently 0, 1 or 2, each q is independently 0 or 1, and each $A^\ominus$ is independently a non-chromophoric anion, with the proviso that when $R_1'''$ is hydrogen, the compound is in metal-free form.

8. A metal-free compound according to claim 1 having the formula

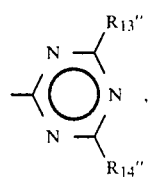

or a 1:1 or 1:2 metal complex thereof, or an acid addition salt of a metal-free compound of said formula or an acid addition salt thereof, wherein A'' is 1,2-ethylene, 1,3-propylene, 1,3-phenylene or 1,4-phenylene, $R_1^{iv}$ is hydrogen or —N=N—D''', wherein D''' is

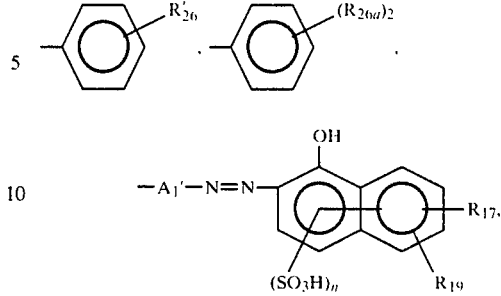

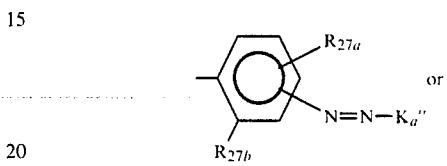

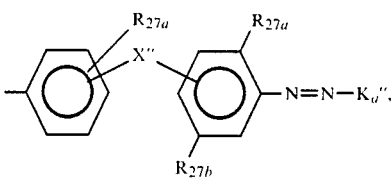

wherein $R_{26}'$ is hydrogen, nitro, chloro, methyl, methoxy or chlorophenoxy, each $R_{26a}$ is independently nitro, chloro, methyl or methoxy, each $R_{27a}$ is independently hydrogen, chloro, methyl or methoxy, and $R_{27b}$ is hydrogen, methyl or methoxy, $R_2''$ is

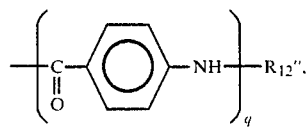

wherein $R_{12}''$ is —CO—$CH_2$—Z'' or

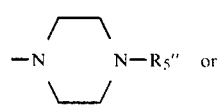

wherein $R_{13}''$ is —$NR_5''R_{21}'$,

—N⟨ ⟩N—$R_5''$ or

-continued

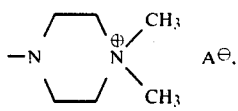

$R_{14}''$ is $-NR_5''R_{21}'$,

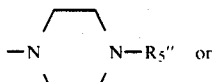

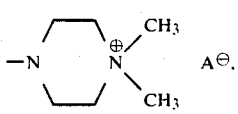

and
$Z''$ is $-N(R_7'')_2$ or $-N^\oplus(R_8'')_2R_9''A^\ominus$, and
$T''$ is cyano or

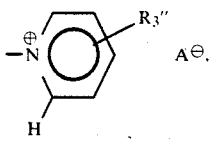

wherein $R_3''$ is hydrogen or methyl,
wherein
$A_1'$ is

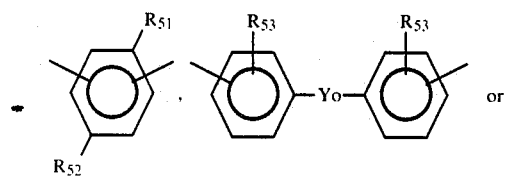

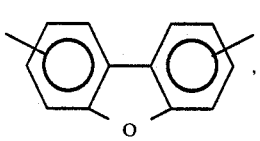

wherein
$R_{51}$ is hydrogen, halo, $C_{1-4}$alkyl or $C_{1-4}$alkoxy,
$R_{52}$ is hydrogen, hydroxy, halo, cyano, $-CONH_2$, ($C_{1-4}$alkyl)carbonylamino, $-NHCONH_2$, carboxy, sulfo, $C_{1-4}$alkyl or $C_{1-4}$alkoxy,
each $R_{53}$ is independently hydrogen, halo, cyano, $C_{1-4}$alkyl, $C_{1-4}$alkoxy, carboxy, sulfo or hydroxy, and
$Y_o$ is a direct bond, $-(CH_2)_a-$, $-O-$, $-S-$, $-SO_2-$, $-NHCO-$, $-NHCONH-$, $-NHCO-(CH_2)_b-CONH-$, $-CONH-(CH_2)_b-NHCO-$, $-O-(CH_2)_b-O-$, $-N=N-$ or $-CH=CH-CO-CH=CH-$,
$K_a''$ is

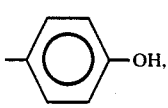

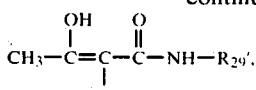

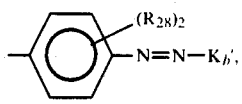

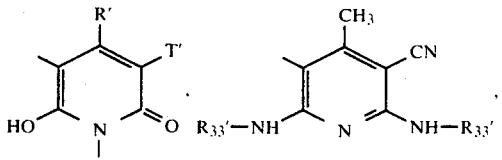

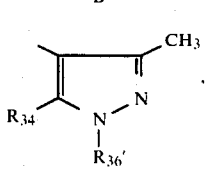

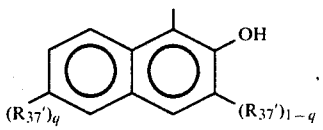

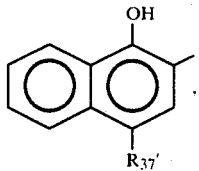

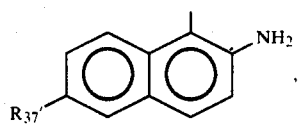

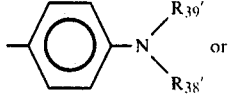

wherein $K_b'$ is

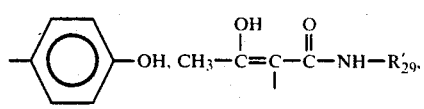

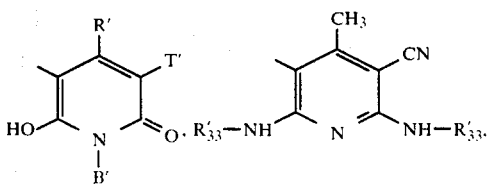

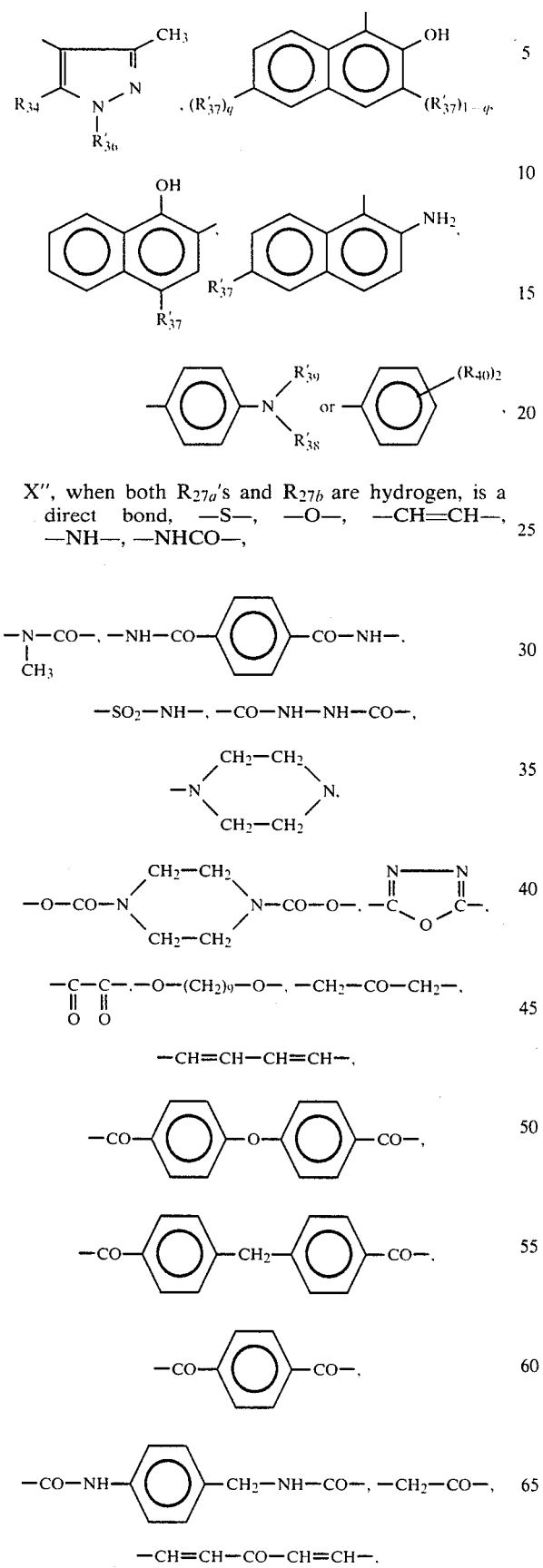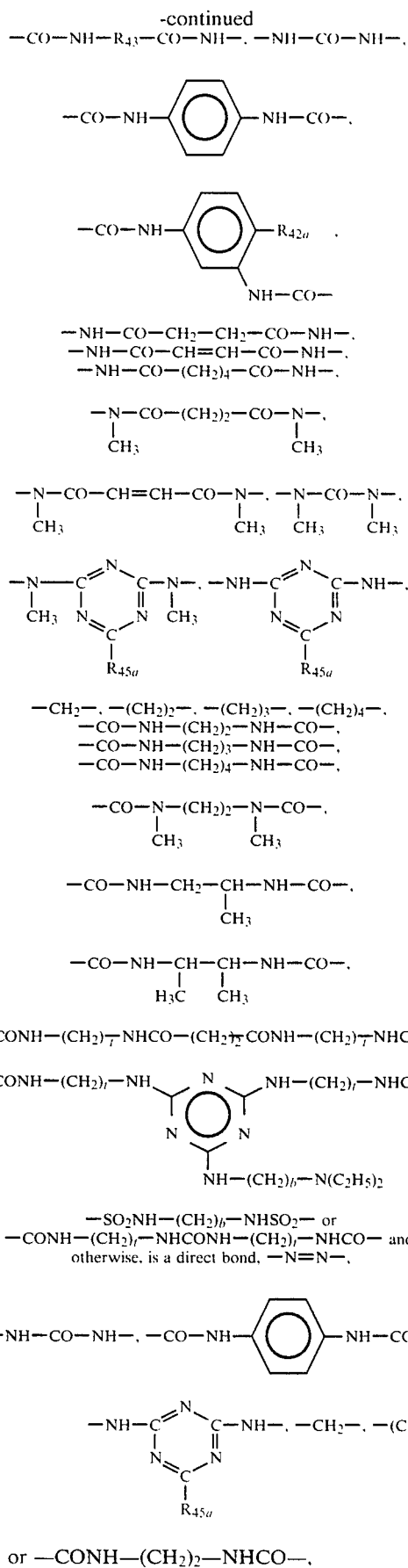

wherein $R_{42a}$ is hydrogen, chloro, methyl or methoxy, $R_{43}$ is linear or branched $C_{1-4}$alkylene, $R_{45a}$ is chloro, 2-hydroxyethylamino, methoxy, ethoxy, hydroxy, amino, N,N-di-(2-hydroxyethyl)amino, 3-diethylaminopropylamino, N-methyl-N-phenylamino, N-cyclohexyl-N-methylamino or piperidino, and g is 1, 2, 3 or 4, and wherein B' is hydrogen, methyl, ethyl, hydroxyethyl, cyclohexyl, benzyl, —$(CH_2)_a$—$N(R_7')_2$, —$(CH_2)_b$—$N^{\oplus}(R_8')_2R_9'A^{\ominus}$ or —A'—NH—$R_2'$, wherein A' is linear or branched $C_{2-8}$alkylene or phenylene, $R_2'$ is

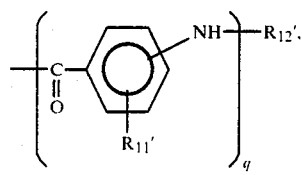

wherein $R_{11}'$ is hydrogen, chloro, nitro, methyl or methoxy, and $R_{12}'$ is —CO—$(CH_2)_t$—Z' or

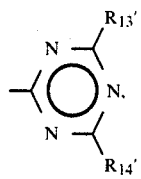

wherein $R_{13}'$ is chloro, hydroxy, amino, N,N-di-($C_{2-4}$-hydroxyalkyl)amino, —$NR_5'R_{21}$,

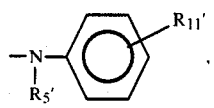

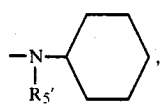

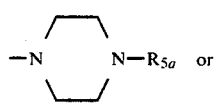

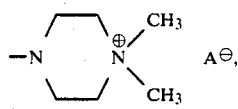

wherein $R_{11}'$ is as defined above, $R_{14}'$ is —$NR_5'R_{21}$,

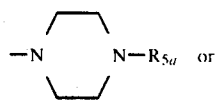

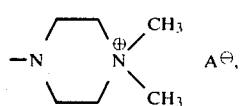

and

Z' is —$N(R_7')_2$ or —$N^{\oplus}(R_8')_2R_9'A^{\ominus}$,

R' is methyl, ethyl, phenyl, benzyl or cyclohexyl, $R_{21}'$ is —$(CH_2)_b$—$N(R_7'')$—$(CH_2)_b$—$NR_7''R_6'$, —$(CH_2)_b$—$N^{\oplus}(R_8'')_2$—$(CH_2)_b$—$N(R_8'')_2R_6'$-$2A^{\ominus}$, —$(CH_2)_b$—$N(R_7'')$—$C_2H_5$, —$(CH_2)_b$—$N^{\oplus}(R_8'')_2$—$C_2H_5A^{\ominus}$, —NHCO—$CH_2$—Z'', —$CH_2$—CONH—$Y_2'$—Z'',

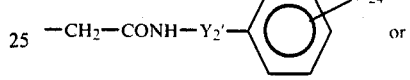

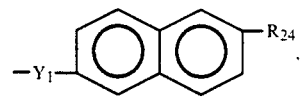

wherein $R_6'$ is methyl or ethyl, $R_{24}$ is —$N(R_7')_2$, —$N^{\oplus}(R_8')_2R_9'A^{\ominus}$, —CO—$Y_2$—Z', —NHCO—$Y_2$—Z', —CONH—$Y_2$—Z'—$SO_2NH$—$Y_2$—Z', —$Y_2$—Z' or —NHNH—CO—$CH_2$—Z', wherein Z' is as defined above, $Y_2'$ is linear or branched $C_{1-4}$alkylene, and Z'' is as defined above, each $R_{28}$ is independently hydrogen, halo, $C_{1-4}$alkyl or $C_{1-4}$alkoxy, $R_{29}'$ is —$(CH_2)_{m'}$—Z',

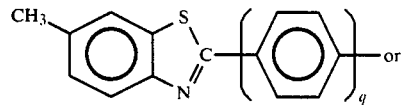

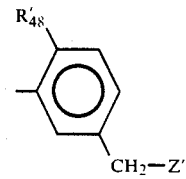

wherein $R_{46}'$ is hydrogen, —NHCO—$(CH_2)_b$—Z', —$SO_2NH$—$(CH_2)_b$—Z' or

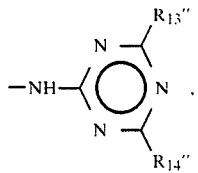

wherein $R_{13}''$, $R_{14}''$ and $Z'$ are as defined above, each $R_{47}'$ is independently hydrogen, chloro, bromo, methyl, ethyl, methoxy, ethoxy, nitro or cyano, and $R_{48}'$ is methoxy or ethoxy, and each $R_{33}'$ is independently hydrogen, 2-hydroxyethyl, 3-methoxypropyl, —(CH$_2$)$_b$—N(CH$_3$)$_2$ or —(CH$_2$)$_b$—N$^\oplus$(CH$_3$)$_3$A$^\ominus$, $R_{34}$ is hydroxy or amino, $R_{36}'$ is hydrogen,

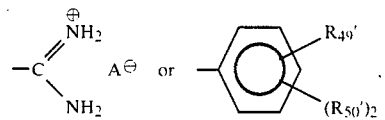

wherein $R_{49}'$ is hydrogen, —CONH—(CH$_2$)$_{m'}$—Z', —NH-CO—(CH$_2$)$_b$—Z' or

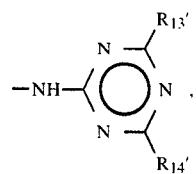

wherein $R_{13}'$, $R_{14}'$ and $Z'$ are as defined above, and each $R_{50}'$ is independently hydrogen, chloro, methyl or methoxy, $R_{37}'$ is

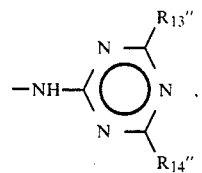

wherein $R_{13}''$ and $R_{14}''$ are as defined above, $R_{38}'$ is methyl, ethyl, 2-cyanoethyl or benzyl, $R_{39}'$ is methyl, ethyl or —(CH$_2$)$_{m'}$—Z, $R_{40}$ is independently hydrogen, C$_{1-4}$alkyl or C$_{1-4}$alkoxy, and each T' is independently hydrogen, cyano, —CO—N(R$_5'$)$_2$ or

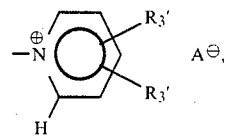

wherein each $R_3'$ is independently hydrogen, methyl, ethyl, amino or dimethylamino, wherein each $R_7'$ is independently hydrogen, C$_{1-6}$alkyl, n-hydroxy(C$_{2-3}$alkyl), benzyl or 2-cyanoethyl or —N(R$_7'$)$_2$ is pyrrolidino, piperidino, morpholino, piperazino or N'-methylpiperazino, each $R_7''$ is independently hydrogen, methyl, ethyl or 2-hydroxyethyl or —N(R$_7''$)$_2$ is morpholino, piperidino, piperazino or N'-methylpiperazino, each $R_8'$ is independently C$_{1-6}$alkyl, n-hydroxy(C$_{2-3}$alkyl), benzyl or 2-cyanoethyl, and each $R_9'$ is independently methyl, ethyl, propyl or benzyl or —N$^\oplus$(R$_8'$)$_2$R$_9'$ is pyridinium, pyridinium substituted by 1 or 2 methyl groups or

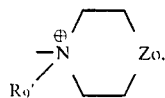

wherein

Zo is a direct bond, —CH$_2$—, —O—, —S—, —SO—, —SO$_2$—, —NH—, —NR$_6$— or —N$^\oplus$(R$_6$)$_2$—A$^\ominus$, and $R_9'$ is as defined above, each $R_8''$ is independently methyl, ethyl or 2-hydroxyethyl, and each $R_9''$ is independently methyl, ethyl or benzyl or —N$^\oplus$(R$_8''$)$_2$R$_9''$ is pyridinium, pyridinium substituted by 1 or 2 methyl groups or

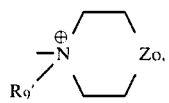

wherein $R_9'$ and Zo are as defined above, each $R_{13}'$ and $R_{14}'$ is independently as defined above, $R_{21}$ is C$_{1-12}$alkyl; C$_{2-12}$alkyl substituted by hydroxy; C$_{3-12}$alkyl interrupted by 1 to 3 radicals selected from —NR$_7$— and —N$^\oplus$(R$_8$)$_2$—A$^\ominus$; —NH-CO—CH$_2$—Z; —CH$_2$—CONH—Y$_1$—Z; —Y$_1$—Z;

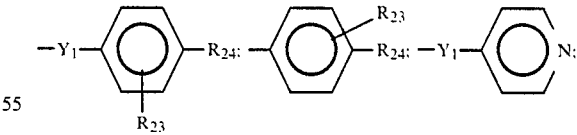

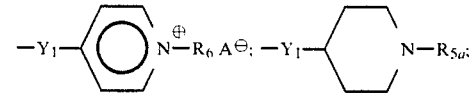

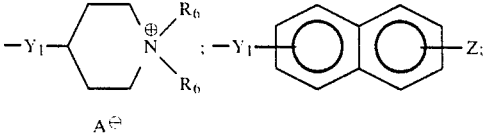

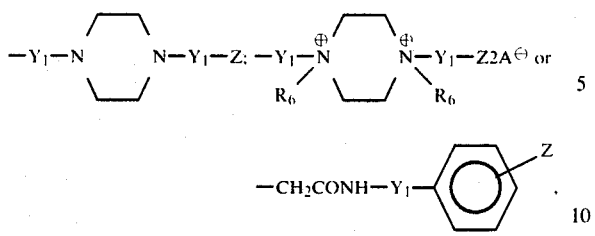
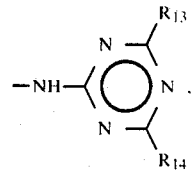

wherein
$R_{23}$ is halo, hydroxy, nitro, $C_{1-4}$alkyl or $C_{1-4}$alkoxy, and
$R_{24}$ and $Z'$ are as defined above, wherein
each $R_5'$ is independently hydrogen, methyl or ethyl,
each $R_5''$ is independently hydrogen or methyl,
each $R_{5a}$ is independently hydrogen or $C_{1-4}$alkyl,
each $R_6$ is independently $C_{1-4}$alkyl,
each $Y_1$ is independently linear or branched $C_{1-8}$alkylene or linear or branched $C_{3-8}$alkenylene,
each $Y_2$ is independently linear or branched $C_{1-8}$alkylene,
$R_7$, $R_8$, $R_{17}$, $R_{19}$ and Z as defined in claim 18,
each a is independently 1, 2 or 3,
each b is independently 2 or 3,
each m' is independently 2, 3 or 4,
each n is independently 0, 1 or 2,
each q is independently 0 or 1,
each t is independently 1 or 2, and
each $A^\ominus$ is independently a non-chromophoric anion, with the proviso that when $R_1^{iv}$ is hydrogen, the compound is in metal-free form.

9. A metal-free compound according to claim 1 having the formula

—NHCO—$Y_2$—Z, —SO$_2$NH—$Y_2$—Z, —NHNH-CO—CH$_2$—Z or

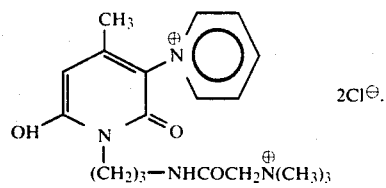

wherein $Y_2$ is linear or branched $C_{1-8}$alkylene,
each M is independently hydrogen or a non-chromophoric cation, and
B, R, $R_{13}$, $R_{14}$, T, Z and $A^\ominus$ are as defined in claim 1, with the provisos tht (i) the total number of cationic and protonatable basic groups exceeds the number of sulfo groups by at least one, and (ii) $R_{64}$ is in the 3- or 4-position of the ring to which it is attached.

10. The compound according to claim 1 having the formula

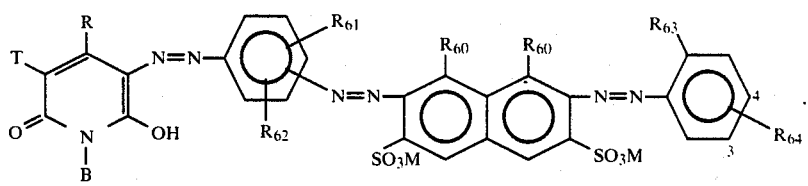

11. The compound according to claim 1 having the formula or a 1:1 or 1:2 metal complex thereof, or an acid addition salt of a metal-free compound of said formula or a 1:1 or 1:2 metal complex thereof,
wherein
one $R_{60}$ is hydroxy and the other is amino,
$R_{61}$ is hydrogen, $C_{1-4}$alkoxy or hydroxy,
$R_{62}$ is hydrogen, chloro, nitro, $C_{1-4}$alkyl, $C_{1-4}$alkoxy or hydroxy,
$R_{63}$ is hydrogen, chloro, nitro, $C_{1-4}$alkyl, $C_{1-4}$alkoxy or hydroxy,
$R_{64}$ is hydrogen, dimethylamino, trimethylammonium $A^\ominus$, diethylamino, triethylammonium $A^\ominus$, —CO—$Y_2$—Z, —CONH—$Y_2$—Z, —$Y_2$—Z,

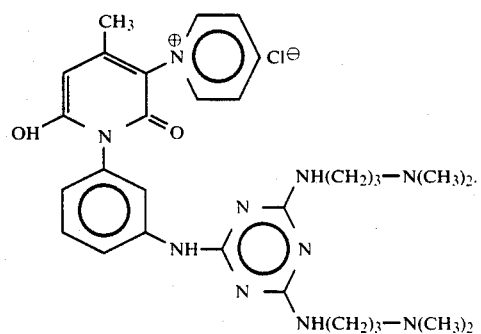

12. The compound according to claim 1 having the formula

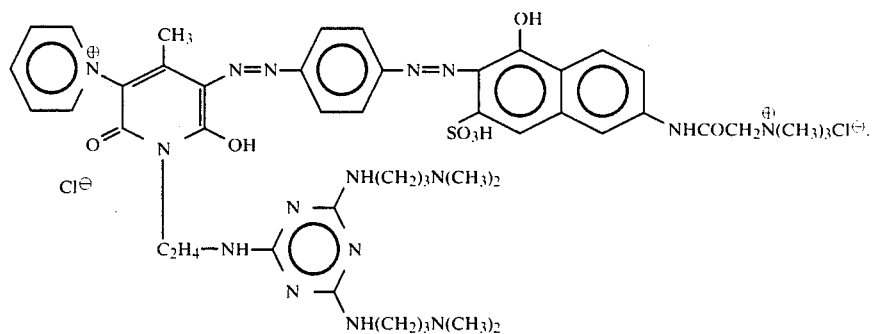
13. The compound according to claim 1 having the formula
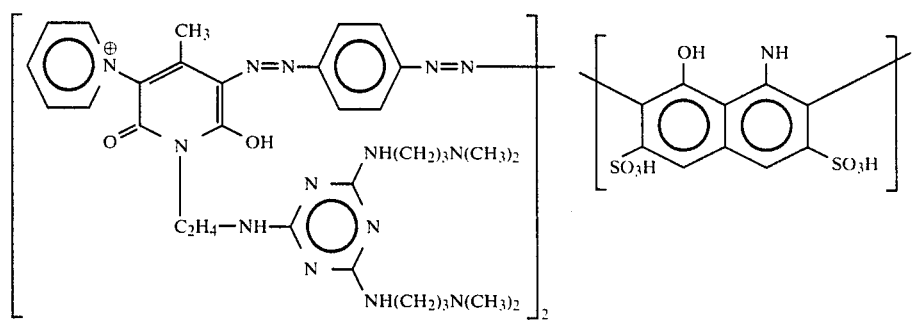
* * * * *